US007595432B2

(12) United States Patent
Sebastian et al.

(10) Patent No.: US 7,595,432 B2
(45) Date of Patent: Sep. 29, 2009

(54) **GENETIC LOCI ASSOCIATED WITH *SCLEROTINIA* TOLERANCE IN SOYBEAN**

(75) Inventors: Scott Sebastian, Polk City, IA (US); Hong Lu, Johnston, IA (US); Feng Han, Johnston, IA (US); Donald Kyle, Princeton, IL (US); Bradley Hedges, Kingsville (CA); Michael Roach, Redwood Falls, MN (US); Paul Stephens, Princeton, IL (US); Jean Liu, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 275 days.

(21) Appl. No.: 11/282,969

(22) Filed: Nov. 17, 2005

(65) Prior Publication Data

US 2006/0137039 A1 Jun. 22, 2006

Related U.S. Application Data

(60) Provisional application No. 60/629,028, filed on Nov. 17, 2004, provisional application No. 60/629,029, filed on Nov. 17, 2004.

(51) Int. Cl.
*A01H 1/00* (2006.01)
*A01H 1/02* (2006.01)
*C12N 5/04* (2006.01)

(52) U.S. Cl. .................. 800/267; 800/260; 800/265; 800/266; 800/312

(58) Field of Classification Search ............... None
See application file for complete search history.

(56) References Cited

U.S. PATENT DOCUMENTS

| | | | |
|---|---|---|---|
| 5,523,520 A | 6/1996 | Hunsperger et al. | |
| 6,399,855 B1 | 6/2002 | Beavis | |
| 2003/0150016 A1 | 8/2003 | Han | |

FOREIGN PATENT DOCUMENTS

| | | |
|---|---|---|
| CA | 2449782 | 12/2002 |
| WO | WO 98/13478 A2 | 4/1998 |
| WO | 98/41655 A | 9/1998 |
| WO | WO 01/49104 A2 | 7/2001 |
| WO | 02/099385 A | 12/2002 |

OTHER PUBLICATIONS

Pioneer Hi-Bred International, Inc., 05826622.2, European Search Report, Feb. 15, 2008, 4 pages.
MacGuire, Tina L. et al., "Tissue-specific gene expression in soybean (*Glycine max*) detected by cDNA microarray analysis", J. Plant Physiol. 159. (2002), pp. 1361-1374.
Vodkin, Lila O. et al., "Microarrays for global expression constructed with a low redundancy set of 27,500 sequenced cDNAs representing an array of developmental stages and physiological conditions of the soybean plant", BMC Genomics, BNSDOCID:XP 21002158A, , Sep. 29, 2004, pp. 1-18.
Alexander et al. (1993) "Increased tolerance to two oomysete pathogens in transgenic tobacco expressing pathogenesis-related protein 1a." Proc. Natl. Acad. Sci. USA 90:7327-7331.
Arahana, Venancio et al. "Identification of QTLs for Resistance to *Sclerotinia sclerotiorum* in Soybean" Crop Sci. 41:180-188 (2001).
Blechert, Siegfried et al. "The octadecanoic pathway: Signal molecules for the regulation of secondary pathways" Proc. Natl. Acad. Sci. vol. 92, pp. 4099-4105, May 1995.
Chou, Wing-Ming et al. "Enzymatic Oxidations in the biosynthesis of complex alkaloids" The Plant Journal (1998) 15 (3), pp. 289-300.
Cline, Steven D., et al. "Stimulation of Sanguinarine Production by Combined Fungal Elicitation and Hormonal Deprivation in Cell Suspension Cultures of *Papaver bracteatum*" Plant Physiol. (1988)86, pp. 0161-0165.
Concibido, Vergel C., et al. "Genome Mapping of Soybean Cyst Nematode Resistance Genes in 'Peking', PI 90763, and PI 88788 Using DNA Markers" Crop Sci. 37:258-264 (1997).
Concibido, V.C. et al. "Introgression of a quantitative trait locus for yield from *Glycine soja* into commercial soybean cultivars", Theor. Appl. Genet (2003) 106:575-582.
Cregan, Perry B., et al. "Microsatellite Fingerprinting and Mapping of Soybean" Methods in Molecular and Cellular Biology 5:49-61 (1994).
Cregan, P. B. "An Integrated Genetic Linkage Map of the Soybean Genome" Crop Sci. 39:1464-1490 (1999).
Dittrich, Heinz et al. "Molecular cloning, expression, and induction of berberine bridge enzyme, an enzyme essential to the formation of benzophenanthridine alkaloids in the response of plants to pathogenic attack" Proc. Natl. Acad. Sci., vol. 88, pp. 9969-9973, 1991.
Eilert, U., et al. "Stimulation of Sanguinarine Accumulation in *Papaver somniferum* Cell Cultures by Fungal Elicitors", J. Plant Physiol. vol. 119, pp. 55-64 (1985).
Eshed, Yuval et al. "Less-Than-Additive Interactions of Quantitative Trait Loci in Tomato" Genetics 143: 1807-1817 (Aug. 1996).
Faccini, Peter J., et al. "Uncoupled Defense Gene Expression and Antimicrobial Alkaloid Accumulation in Elicited Opium Poppy Cell Cultures" Plant Physiol. (1996) 111:687-697.
Haley, C. S. , et al. "A simple regression method for mapping quantitative trait loci in line crosses using flanking markers" Heredity 69 (1992) pp. 315-324.
Haussmann, B.I.G., et al. "Plant genetic resources in crop improvement" Plant Genetic Resources 2(1); pp. 3-21(2004).

(Continued)

*Primary Examiner*—Medina A Ibrahim
(74) *Attorney, Agent, or Firm*—McKee, Voorhees & Sease, P.L.C.

(57) ABSTRACT

The invention relates to methods and compositions for identifying soybean plants that are tolerant, have improved tolerance or are susceptible to *Sclerotinia* sp. infection (the causative agent of white mold). The methods use molecular genetic markers to identify, select and/or construct disease-tolerant plants or identify and counterselect disease-susceptible plants. Soybean plants that display tolerance or improved tolerance to *Sclerotinia* sp. infection that are generated by the methods of the invention are also a feature of the invention.

22 Claims, 19 Drawing Sheets

OTHER PUBLICATIONS

Jansen, Ritsert C. "Controlling the Type I and Type II Errors in Mapping Quantitative Trait Loci" Genetics 138: 871-881 (Nov. 1994).

Keim and Shoemaker "Construction of a random DNA library that is primarily single copy sequences." Soybean Genet Newsletter 15:147-148 (1998).

Kim, H. S. et al. "Evaluation of Soybean Cultivars for Resistance to *Sclerotinia* Stem Rot in Field Environments" Crop Sci. 39:64-68 (1999).

Kim, H. S. et al. "Inheritance of Partial Resistance to *Sclerotinia* Stem Rot in Soybean" Crop Sci. 40:55-61 (2000).

Kim, H.S. et al. "Reaction of Soybean Cultivars to *Sclerotinia* Stem Rot in Field, Greenhouse, and Laboratory Evaluations" Crop Sci. 40:665-669 (2000).

Kraft, T., et al. "Linkage disequilibrium and fingerprinting in sugar beet" Theor Appl. Genet (2000) 101:323-326.

Kutchan, Toni M. "12-Oxo-Phytodienoic Acid Induces Accumulation of Berberine Bridge Enzyme Transcript in a Manner Analogous to Methyl Jasmonate" J. Plant Physiol. vol. 142, pp. 502-505 (1993).

Kutchan, Toni M. et al. "Characterization and Mechanism of the Berberine Bridge Enzyme, a Covalently Flavinylated Oxidase of Benzophenanthridine Alkaloid Biosynthesis in Plants" The Journal of Biological Chemistry, vol. 270, No. 41, Oct. 1995, pp. 24475-24461.

Lander, Eric S., et al. "Mapping Mendelian Factors Underlying Quantitative Traits Using RFLP Linkage Maps" Genetics 121:185-199 Jan. 1989.

Lee, S. H., et al. "Identification of quantitative trait loci for plant height, lodging, and maturity in a soybean population segregating for growth habit" Theor. Appl. Genet (1996) 92:516-523.

Manly, Kenneth F., et al. "RI Manager, a microcomputer program for analysis of data from recombinant inbred strains" Mammalian Genome (1991) 1:123-126.

Manly, Kenneth F., et al. "Overview of QTL mapping software and introduction to Map Manager QT" Mamalian Genome 10, 327-334 (1999).

Michelmore, R. W., et al. "Identification of markers linked to disease-resistance genes by bulked segregant analysis: A rapid method to detect markers in specific genomic regions by using segregating populations" Proc. Natl. Acad. Sci., vol. 88, pp. 9828-9832, Nov. 1991 Genetics.

Niderman, Thierry et al. "Pathogenesis-Related PR-1 Proteins ARe Antifungal" Plant Physiol. (1995) 108:17-27.

Schumacher, H.M. et al. "Elicitation of benzophenanthridine alkaloid synthesis in *Eschscholtzia* cell cultures" Plant Cell Reports (1987) 6: 410-413.

Schoemaker, Randy C., et al. "RFLP map of soybean" DNA-based Makers in Plants, Chapter 21, pp. 357-358 (2001).

Stuber, Charles W., et al. "Synergy of Empirical Breeding, Marker-Assisted Selection, and Genomics to Increase Crop Yield Potential" Crop Sci. 39:1571-1583 (1999).

vanOoijen, J. W., et al. "An RFLP linkage map of *Lycopersicon peruvianum*" Theor. Appl. Genet (1994) 89:1007-1013.

Westman, A. L., et al. "The potential for cross-taxa simple-sequence repeat (SSR) amplification between *Arabidopsis thaliana* L. and crop brasicas" Theor. Appl. Genet (1998) 96: 272-281.

Willmot, David B., et al. "Genetic Analysis of Brown Stem Rot Resistance in Soybean" Crop Sci. 29:672-674 (1989).

Young, N.D. "QTL Mapping and Quantitative Disease Resistance in Plants" Ammu. Rev. Pytopathol. 1996, 34:479-501.

Pioneer Hi-Bred International U.S. Appl. No. 10/165,617, pp. 146-149; filed Jun. 7, 2002.

PCT/US02/18173 Pioneer Hi-Bred International, Inc. Search Report dated Jun. 7, 2002.

Yuan et al., "Quantitative trait loci in Two Soybean Recombinant Inbred Line Populations Segregating for Yield and Disease Resistance", Crop Sci. 42:271-277 (2002).

Kim et al., "Isolation and Differential Expression of an Acidic PR-1 cDNA Gene from Soybean Hypocotyis infected with *Phytophthora sojae* f. sp. *glycines*", Plant Pathol. J. 16(1):9-18 (2000).

Quotob et al., "Comparative Analysis of Expressed Sequences in *Phytophthora sojae*", Plant Phys. 123:243-253 (2000).

Shoemaker et al., "Public Soybean EST Project: BE 803700", GenBank Acc. No. BE803700 (2000).

National Center for Genome Resources, "SoyBase", http://soybase.ncgr.org/cgi-bin/ace/generic/search/soybase (2007).

Coryell et. al "Allele-specific hybridization markers for soybean" Theor Appl Genet (1999) 98: 690-696.

Wu et. al, "A BAC and BIBAC-based Physical Map of the Soybean Genome" Genome Res. Feb. 2004 14(2):319-326.

Bolton, Melvin D., et al., "*Sclerotinia sclerotiorum* (Lib.) de Bary: biology and molecular traits of a cosmopolitan pathogen", Molecular Plant Pathology, 7(1):1-16 (Jan. 2006).

PCT/US2005/042012 International Search Report.

Arahana et al., "Identification of QTLs for Resistance to *Sclerotinia sclerotiorum* in Soybean", Crop Sci. 41:180-188 (2001).

Cregan et al., "An Integrated Genetic Linkage Map of the Soybean Genome", Crop. Sci. 39:1464-1490 (1999).

Kim et al., "Inheritance of Partial Resistance to *Sclerotinia* Stem Rot in Soybean", Crop Sci. 40:55-61 (2000).

| Marker | Marker Type | Chrom | Relative Map Position (cM) | Method of Identification | Gene Pool Analyzed/ Mapping Population | Adjusted Probability | Notes |
|---|---|---|---|---|---|---|---|
| SAG1032 | genomic SSR | B1 | 65.6 | Association Mapping | Multiple lines representative of US elite soybean germplasm. | 0.0002 | This marker region was identified twice by association mapping in two independent years of data analysis. |
| SATT597 | genomic SSR | B1 | 68.1 | Association Mapping | Multiple lines representative of US elite soybean germplasm. | 0.0417 | |
| SCT_026 | SSR | B1 | 71.6 | Association Mapping | Multiple lines representative of US elite soybean germplasm. | 0.0038 | This marker region was identified twice by association mapping in two independent years of data analysis. |
| SATT391 | genomic SSR | C1 | 50.0 | Marker Regression | 9163(TOL) x 92B05(SUS) | 0.0270 | |
| | | | | | | 0.0481 | Result derived from field data. |
| S60817-TB | EST-SSR | F | 30.0 | Intergroup Analysis | Multiple lines representative of US elite soybean germplasm. | 0.0 | Marker also correlates with purple/white flower color. Allele 2 prevalent in tolerant plants. Alleles 3 and 4 prevalent in susceptible plants. |
| S60239-TB | EST-SSR | G | 0.0 | Association Mapping | Multiple lines representative of US elite soybean germplasm. | 0.0000 | This marker region was identified twice by association mapping in two independent years of data analysis. |
| P10646A-1 | SNP | G | 2.0 | Association Mapping | Multiple lines representative of US elite soybean germplasm. | 0.0158 | |
| P7659A-2 | SNP | G | 4.0 | Association Mapping | Multiple lines representative of US elite soybean germplasm. | 0.0478 | |
| SATT570 | genomic SSR | G | 7.7 | Association Mapping | Multiple lines representative of US elite soybean germplasm. | 0.0092 | |
| SATT356 | genomic SSR | G | 8.5 | Association Mapping | Multiple lines representative of US elite soybean germplasm. | 0.0381 | |

Fig. 1

| Marker | Marker Type | Chrom | Relative Map Position (cM) | Method of Identification | Gene Pool Analyzed/ Mapping Population | Adjusted Probability | Notes |
|---|---|---|---|---|---|---|---|
| S60222-TB | EST-SSR | K | 170.0 | Association Mapping | Multiple lines representative of US elite soybean germplasm. | 0.0102 | |
| SATT166 | genomic SSR | L | 77.1 | Marker Regression | 9163(TOL) x 92B05(SUS) | 0.0043 | Result derived from field data. |
| SATT448 | genomic SSR | L | 78.0 | Marker Regression | 9163(TOL) x 92B05(SUS) | 0.0102 | Result derived from field data. |
| SAG1048 | genomic SSR | M | 84.2 | Intergroup Analysis | Multiple lines representative of US elite soybean germplasm. | 0.0299 | |
| SATT243 | genomic SSR | O | 157.0 | Intergroup Analysis | Multiple lines representative of US elite soybean germplasm. | 0.000012 | |
| | | | | Marker Regression | 9163(TOL) x 92B05(SUS) | 0.0000 | |

Fig. 1 (cont.)

| Marker Name | Left Primer Sequence | Right Primer Sequence | Pigtail | Repeat |
|---|---|---|---|---|
| SAG1032 | TTTGTTTGATCTATGCACTTGC (SEQ ID NO:1) | GCCAAGTCACACACACCAAG (SEQ ID NO:2) | GTTTCTT | 3 |
| SATT597 | TGCTGCAGCGTGTCTGTAGTATAATTT (SEQ ID NO:3) | GGCACAACCATCACCACCTTATT (SEQ ID NO:4) | GTTTCTT | 3 |
| SCT_026 | GAAACCCGAAACGCAAAATCTC (SEQ ID NO:5) | GAAGAAAACGCGAATAACCCCA (SEQ ID NO:6) | GTTTCTT | 3 |
| SATT391 | TGCTCAAAGGGTCAATTTCTTTCC (SEQ ID NO:7) | TGTGTAATTTCTATCACCTTATTGTGCC (SEQ ID NO:8) | GTTTCTT | 3 |
| S60817-TB | CCTCTTCAACAAAAACACCCGTT (SEQ ID NO:9) | GACCCCCAGCTTCTCATTCTCA (SEQ ID NO:10) | GTTTCTT | 3 |
| S60239-TB | ACCTCGGTTATTACGGCCTCCA (SEQ ID NO:11) | AATTGCTACACCACCACACCAA (SEQ ID NO:12) | GTTTCTT | 3 |
| SATT570 | TGCTCATGTGGTCCTACCCAGA (SEQ ID NO:13) | CGCTATCCCTTTGTATTTCTTTTGC (SEQ ID NO:14) | GTTTCTT | 3 |
| SATT356 | TGCTGCTTGTGTTTGGTTGATCT (SEQ ID NO:15) | CATATCCTGCCCCCCAATTAT (SEQ ID NO:16) | GTTTCTT | 3 |
| SATT240 | TCCTTGGGGTGAATTGTTTTTCA (SEQ ID NO:17) | CCTTCTTTGACATGGGGCCTA (SEQ ID NO:18) | GTTTCTT | 3 |
| S60222-TB | TCGGCTGAAGATCCGAGTAGT (SEQ ID NO:19) | TCAGCATAAAACCATTAAAAGCAAAA (SEQ ID NO:20) | GTTTCTT | 3 |
| SATT166 | CAGTTGATTTTTGTTTTTTCGGCA (SEQ ID NO:21) | CACGCGCATCAGCCTGTTGTAGAG (SEQ ID NO:22) | GTTTCTT | 3 |
| SATT448 | CACCACTCGTATCCTTCACAAGAGC (SEQ ID NO:23) | GCCAGCAGCCTGTTCAGTTTTT (SEQ ID NO:24) | GTTTCTT | 3 |
| SAG1048 | TGGCAGTGGGTAGTGAATG (SEQ ID NO:25) | AAAGATGGCTGACTTTGTTTACA (SEQ ID NO:26) | GTTTCTT | 3 |
| SATT463 | TTTGGATTCATATATTCAAACTTTCAAG (SEQ ID NO:27) | CTGCAAATTTGATGCACATGTGTCTA (SEQ ID NO:28) | GTTTCTT | 3 |
| SATT175 | GACCTCGCTCTCTGTTTCTCAT (SEQ ID NO:29) | GGTGACCACCCCTATTCCTTAT (SEQ ID NO:30) | | |
| SATT536 | GCGTGGAATGAGACGTAACCAA (SEQ ID NO:31) | GCATAATGGTCTAATAAAAGTGGAGACC (SEQ ID NO:32) | GTTTCTT | 3 |
| SATT243 | AATGCTTTGGTCGTTGCATTG (SEQ ID NO:33) | TGGTATCGGGAGATTTTTCAGC (SEQ ID NO:34) | | |

Fig. 2

| SNP Marker | PCR Primers | Allele Probes |
|---|---|---|
| P10646A-1 | Primer Seq 1: CCCCCAACAAAACTAAAAATAGAACCCTCAACAACC (SEQ ID NO:35)<br>Primer Seq 2: GGTCCAAGAACATTATGATCTTGAACAATCTTCAC (SEQ ID NO:36) | Allele 1 Probe: TGTGACAACCGA (SEQ ID NO:39)<br>Allele 2 Probe: GTGACACAACC (SEQ ID NO:40) |
| P7659A-2 | Primer Seq 1: CATGAAGCTCCACCATTTGCTAGTACATGAAAC (SEQ ID NO:37)<br>Primer Seq 2: CCAGAGTTACCAAACCATCTGTGAGAAATATCC (SEQ ID NO:38) | Allele 1 Probe: GAGGAGATGTAG (SEQ ID NO:41)<br>Allele 2 Probe: GAGGAAATGTAG (SEQ ID NO:42) |

Fig. 3

| Marker | Allele | Size Range (bp) |
|---|---|---|
| SAG1032 | 1 | 94.50 to 95.55 |
| | 2 | 98.50 to 100.00 |
| | 3 | 105.00 to 106.00 |
| | 4 | 100.70 to 101.50 |
| | | |
| SATT597 | 1 | 144.68 to 145.51 |
| | 2 | 147.86 to 148.82 |
| | 3 | 160.26 to 161.37 |
| | 4 | 157.34 to 158.05 |
| | | |
| SCT_026 | 1 | 328.36 to 329.50 |
| | 2 | 330.38 to 331.40 |
| | 3 | 326.64 to 326.84 |
| | 4 | 333.80 to 334.25 |
| | 5 | 317.50 to 317.65 |
| | | |
| SATT391 | 1 | 168.69 to 169.85 |
| | 2 | 183.67 to 184.90 |
| | 3 | 181.12 to 181.29 |
| | 4 | 187.28 to 187.48 |
| | 5 | 165.60 to 166.80 |
| | | |
| S60817-TB | 1 | 244.00 to 244.65 |
| | 2 | 247.00 to 248.00 |
| | 3 | 253.00 to 254.00 |
| | 4 | 256.00 to 257.00 |
| | | |
| S60239-TB | 1 | 220.00 to 221.00 |
| | 2 | 224.00 to 225.00 |
| | | |
| SATT570 | 1 | 108.50 to 109.05 |
| | 2 | 111.41 to 112.41 |
| | 3 | 114.48 to 115.41 |
| | 4 | 126.57 to 127.58 |
| | 5 | 120.72 to 120.97 |
| | 6 | 130.01 to 130.51 |
| | 7 | 132.94 to 133.17 |
| | | |
| SATT356 | 1 | 322.24 to 323.40 |
| | 2 | 325.15 to 326.50 |
| | | |
| S60222-TB | 1 | 318.75 to 319.75 |
| | 2 | 319.90 to 321.35 |
| | | |
| SATT166 | 1 | 187.08 to 188.45 |

Fig. 4

| Marker | Allele | Size Range (bp) |
|---|---|---|
|  | 2 | 220.48 to 221.35 |
|  | 3 | 226.44 to 227.75 |
|  | 4 | 229.48 to 230.45 |
|  | 5 | 232.37 to 233.80 |
|  | 6 | 223.39 to 223.76 |
|  | 7 | 217.35 to 217.75 |
|  | 8 | 206.00 to 206.50 |
|  | 9 | 211.50 to 213.00 |
|  | 10 | 193.30 to 194.70 |
|  |  |  |
| SATT448 | 1 | 340.69 to 341.70 |
|  | 2 | 347.47 to 348.25 |
|  | 3 | 350.42 to 350.92 |
|  | 4 | 355.86 to 356.92 |
|  | 5 | 361.62 to 362.12 |
|  | 6 | 358.66 to 359.50 |
|  | 7 | 364.68 to 365.08 |
|  | 8 | 343.59 to 344.60 |
|  | 9 | 332.07 to 332.27 |
|  | 10 | 324.81 to 325.01 |
|  |  |  |
| SAG1048 | 1 | 123.00 to 123.50 |
|  | 2 | 148.00 to 149.50 |
|  | 3 | 156.50 to 158.00 |
|  | 4 | 163.50 to 164.50 |
|  | 5 | 165.50 to 166.50 |
|  | 6 | 158.50 to 159.50 |
|  | 7 | 138.50 to 139.50 |
|  | 8 | 125.00 to 126.50 |
|  |  |  |
| SATT243 | 1 | 334.69 to 336.15 |
|  | 2 | 343.48 to 344.75 |
|  | 3 | 363.37 to 364.48 |
|  | 4 | 366.24 to 367.20 |
|  | 5 | 357.96 to 358.16 |
|  | 6 | 337.76 to 339.00 |
|  | 7 | 346.58 to 347.10 |
|  | 14 | 349.47 to 349.60 |

Fig. 4 (cont.)

| Strains | Class | SAG1048 Marker Allele |
|---|---|---|
| 1 | TOL | |
| 2 | TOL | 2/4 |
| 3 | TOL | 4 |
| 4 | TOL | 3 |
| 5 | TOL | |
| 6 | TOL | 2 |
| 7 | TOL | 4 |
| 8 | TOL | |
| 9 | TOL | |
| 10 | TOL | |
| 11 | TOL | 2 |
| 12 | TOL | 4 |
| 13 | TOL | 3 |
| 14 | TOL | |
| 15 | TOL | |
| 16 | TOL | |
| 17 | TOL | 3 |
| 18 | TOL | 3 |
| 19 | TOL | |
| 20 | TOL | |
| 21 | TOL | 3 |
| 22 | TOL | 3 |
| 23 | TOL | 3 |
| 24 | TOL | |
| 25 | TOL | 3 |
| 26 | TOL | |
| 27 | TOL | 3 |
| 28 | TOL | 3 |
| 29 | TOL | |
| 30 | TOL | |
| 31 | TOL | 3/8 |
| 32 | TOL | |
| 33 | TOL | 3 |
| 34 | TOL | 4 |
| 35 | TOL | |
| 36 | TOL | |
| 37 | TOL | |
| 38 | TOL | |
| 39 | TOL | |
| 1 | SUS | |
| 2 | SUS | 4 |
| 3 | SUS | 4 |
| 4 | SUS | 2 |
| 5 | SUS | 2 |
| 6 | SUS | 4 |
| 7 | SUS | 2 |
| 8 | SUS | 2 |
| 9 | SUS | |
| 10 | SUS | 2 |
| 11 | SUS | 2 |
| 12 | SUS | 4 |
| 13 | SUS | 2/3 |
| 14 | SUS | 2 |
| 15 | SUS | 2 |
| 16 | SUS | |
| 17 | SUS | 2 |
| 18 | SUS | 2 |
| 19 | SUS | 2 |
| 20 | SUS | 2 |
| 21 | SUS | 2 |
| 22 | SUS | 2 |
| 23 | SUS | 4 |
| 24 | SUS | 2 |
| 25 | SUS | 2 |
| 26 | SUS | 2/3 |
| 27 | SUS | 4 |
| 28 | SUS | 2 |
| 29 | SUS | 2 |
| 30 | SUS | 3 |
| 31 | SUS | 2 |
| 32 | SUS | 2 |
| 33 | SUS | |

Fig. 5

| Marker | Linked Markers |
|---|---|
| SAG1032<br>LG-B1 | A006_1, Satt298, BLT043_1, mO011_1, Sat_348, Satt597, BLT019_2, Sct_026, G214_3 |
| SATT597<br>LG-B1 | A006_1, Satt298, BLT043_1, mO011_1, Sat_348, Satt597, BLT019_2, Sct_026, G214_3, Sat_360, Satt332, Sat_095, L204_1, Satt430, Satt415 |
| SCT_026<br>LG-B1 | mO011_1, Sat_348, Satt597, BLT019_2, Sct_026, G214_3, Sat_360, Satt332, Sat_095, L204_1, Satt430, Satt415, Satt583, Sat_364, Satt444 |
| SATT391<br>LG-C1 | Sat_337, K001_1, V38b, Sat_140, A946_1 |
| S60817-TB<br>LG-F | BLT010_1, Satt423, AW186493, BE806387, Sat_240, Satt659, Satt206, Sat_039, W1, BLT057_1, DUBC767, Sat_298, Satt160 |
| S60239-TB<br>LG-G | Satt163, Satt038, Satt275, H3_c6_2, Sat_210, Sat_168, Satt309, B053_1, AZ254740, Bng122_1, Sat_141 |
| P10646A-1<br>LG-G | Satt163, Satt038, Satt275, H3_c6_2, Sat_210, Sat_168, Satt309, B053_1, AZ254740, Bng122_1, Sat_141, Sat_163, Satt610, Satt356, Satt688, Satt570 |
| P7659A-2<br>LG-G | Satt163, Satt038, Satt275, H3_c6_2, Sat_210, Sat_168, Satt309, B053_1, AZ254740, Bng122_1, Sat_141 |
| SATT570<br>LG-G | H3_c6_2, Sat_210, Sat_168, Satt309, B053_1, AZ254740, Bng122_1, Sat_141, Sat_163, Satt610, Satt356, Satt688, Satt570, AW734137, Satt217, Satt235 |
| SATT356<br>LG-G | Satt275, H3_c6_2, Sat_210, Sat_168, Satt309, B053_1, AZ254740, Bng122_1, Sat_141, Sat_163, Satt610, Satt356, Satt688, Satt570, AW734137, Satt217, Satt235 |
| S60222-TB<br>LG-K | R, K387_1, Sat_293, K266_1, A661_1, Sat_020, Satt196, M7E8mr3, Sat_126, E014_2, P1, Bng007_1 |
| SATT166<br>LG-L | Sct_010, Satt076, Satt448, gy3E_1, Satt166, Sat_113, Satt678, Satt527, Satt561, L050_8, A132_2 |
| SATT448<br>LG-L | Sat_340, Satt156, Sct_010, Satt076, Satt448, gy3E_1, Satt166, Sat_113, Satt678, Satt527, Satt561, L050_8, A132_2 |
| SAG1048<br>LG-M | Satt463, Sat_253, Satt245, A946_2, Satt220, A584_3, Satt626, OP_N04, Satt323, Sat_258, Satt702, L204_4, Satt536, Sat_003, Sat_148, Bng179_2, K417_3, Sat_226, Satt175 |
| SATT243<br>LG-O | Sat_038, A102_2, Mng211_1, Satt153, Satt243, Pgm1, Sat_307, BLT027_1, T027_1, Mng085_1, T010_1, Sat_109, BLT027, Sat_231, Sat_108 |

Fig. 6

Chromosome A1

| Marker | Chrom. Number | Chrom. Name | Position (cM) |
|---|---|---|---|
| SATT684 | 1 | A1 | 1.4 |
| SATT276 | 1 | A1 | 5.1 |
| SAT_368 | 1 | A1 | 5.6 |
| SATT572 | 1 | A1 | 5.7 |
| SAT_344 | 1 | A1 | 10.7 |
| SATT165 | 1 | A1 | 14.6 |
| SATT382 | 1 | A1 | 17.0 |
| SATT593 | 1 | A1 | 18.0 |
| SAT_371 | 1 | A1 | 18.3 |
| SATT042 | 1 | A1 | 19.1 |
| SATT364 | 1 | A1 | 19.1 |
| SATT454 | 1 | A1 | 19.1 |
| SATT471 | 1 | A1 | 19.1 |
| SATT526 | 1 | A1 | 19.1 |
| SATT300 | 1 | A1 | 27.1 |
| SATT591 | 1 | A1 | 27.1 |
| SATT155 | 1 | A1 | 28.5 |
| SATT050 | 1 | A1 | 48.2 |
| SATT385 | 1 | A1 | 69.9 |
| SAG1046 | 1 | A1 | 74.0 |
| SATT545 | 1 | A1 | 75.3 |
| SAG1038 | 1 | A1 | 77.1 |
| SAG1040 | 1 | A1 | 77.1 |
| SATT599 | 1 | A1 | 83.2 |
| SATT211 | 1 | A1 | 86.4 |
| SATT225 | 1 | A1 | 87.3 |
| SATT236 | 1 | A1 | 87.3 |
| SATT258 | 1 | A1 | 87.3 |
| SATT511 | 1 | A1 | 87.3 |
| SAT_271 | 1 | A1 | 89.5 |
| SAT_271-DB | 1 | A1 | 89.5 |
| SAT_217 | 1 | A1 | 93.3 |
| SAT_217-DB | 1 | A1 | 93.3 |
| BNG017_1 | 1 | A1 | 96.4 |

Chromosome A2

| Marker | Chrom. Number | Chrom. Name | Position (cM) |
|---|---|---|---|
| P12390B-1 | 2 | A2 | 0.0 |
| P6181A-2 | 2 | A2 | 2.0 |
| P11347A-1 | 2 | A2 | 5.0 |
| SATT390 | 2 | A2 | 8.6 |
| SATT207 | 2 | A2 | 19.3 |
| SAT_319-DB | 2 | A2 | 19.7 |
| SATT480 | 2 | A2 | 20.0 |
| SATT493 | 2 | A2 | 23.3 |
| SATT589 | 2 | A2 | 23.3 |
| SAG1140 | 2 | A2 | 30.0 |
| SATT315 | 2 | A2 | 33.2 |
| SATT632 | 2 | A2 | 41.8 |
| SATT632-TB | 2 | A2 | 41.8 |
| SATT187 | 2 | A2 | 50.0 |
| SATT341 | 2 | A2 | 73.5 |
| SAT_115 | 2 | A2 | 78.3 |
| SAT_129 | 2 | A2 | 78.3 |
| SATT377 | 2 | A2 | 89.9 |
| SATT525 | 2 | A2 | 93.7 |
| SATT233 | 2 | A2 | 96.2 |
| SAT_250 | 2 | A2 | 103.5 |
| SAT_250-DB | 2 | A2 | 103.5 |
| SATT327 | 2 | A2 | 108.7 |
| SATT329 | 2 | A2 | 108.7 |
| SATT508 | 2 | A2 | 108.7 |
| SATT421 | 2 | A2 | 119.6 |
| SATT470 | 2 | A2 | 119.6 |
| SATT707 | 2 | A2 | 119.6 |
| SATT333 | 2 | A2 | 123.4 |
| SATT133 | 2 | A2 | 132.4 |
| SATT209 | 2 | A2 | 135.1 |
| P10635A-1 | 2 | A2 | 136.0 |
| SATT455 | 2 | A2 | 138.2 |
| SATT409 | 2 | A2 | 154.7 |
| SATT228 | 2 | A2 | 161.8 |
| SATT538 | 2 | A2 | 173.5 |
| SAT_347 | 2 | A2 | 173.8 |
| SATT378 | 2 | A2 | 175.2 |
| SATT429 | 2 | A2 | 184.0 |

Fig. 7

Chromosome B1

| Marker | Chrom. Number | Chrom. Name | Position (cM) |
|---|---|---|---|
| SAT_270 | 3 | B1 | 17.5 |
| SATT426 | 3 | B1 | 22.5 |
| SATT509 | 3 | B1 | 26.7 |
| SAT_261 | 3 | B1 | 27.6 |
| SATT251 | 3 | B1 | 34.9 |
| SATT197 | 3 | B1 | 39.0 |
| SAT_128 | 3 | B1 | 45.0 |
| SATT519 | 3 | B1 | 56.6 |
| S60480-TB | 3 | B1 | 60.0 |
| S60468-TB | 3 | B1 | 60.5 |
| SAG1032 | 3 | B1 | 65.6 |
| SATT597 | 3 | B1 | 68.1 |
| SCT_026 | 3 | B1 | 71.6 |
| SATT332 | 3 | B1 | 73.3 |
| SATT415 | 3 | B1 | 73.3 |
| SATT583 | 3 | B1 | 74.1 |
| SATT430 | 3 | B1 | 74.8 |
| SATT444 | 3 | B1 | 76.4 |
| P12198A-1 | 3 | B1 | 80.0 |
| P8584A-1 | 3 | B1 | 85.0 |
| P8584A-2 | 3 | B1 | 85.0 |
| SATT665 | 3 | B1 | 86.3 |
| SAT_123 | 3 | B1 | 91.9 |
| SATT359 | 3 | B1 | 92.1 |
| SAT_331 | 3 | B1 | 115.2 |
| SAT_331-DB | 3 | B1 | 115.2 |
| SATT453 | 3 | B1 | 117.3 |
| SATT484 | 3 | B1 | 117.3 |
| P10648A-1 | 3 | B1 | 120.0 |

Chromosome B2

| Marker | Chrom. Number | Chrom. Name | Position (cM) |
|---|---|---|---|
| SATT577 | 4 | B2 | 0.0 |
| P12105A-1 | 4 | B2 | 20.0 |
| SAT_264 | 4 | B2 | 22.1 |
| SATT126 | 4 | B2 | 29.9 |
| SATT467 | 4 | B2 | 39.8 |
| SAT_342 | 4 | B2 | 40.6 |
| P10641A-1 | 4 | B2 | 45.0 |
| SCT_034 | 4 | B2 | 50.0 |
| SATT168 | 4 | B2 | 55.8 |
| SATT416 | 4 | B2 | 58.0 |
| SATT304 | 4 | B2 | 69.3 |
| SATT083 | 4 | B2 | 70.2 |
| SAT_355 | 4 | B2 | 71.4 |
| SATT601 | 4 | B2 | 76.1 |
| SATT318 | 4 | B2 | 78.3 |
| SCT_094 | 4 | B2 | 80.2 |
| SAT_189 | 4 | B2 | 86.1 |
| SATT556 | 4 | B2 | 86.1 |
| SATT272 | 4 | B2 | 87.0 |
| SATT122 | 4 | B2 | 87.1 |
| SATT020 | 4 | B2 | 88.6 |
| SATT066 | 4 | B2 | 97.3 |
| SATT534 | 4 | B2 | 110.9 |
| SCT_064 | 4 | B2 | 110.9 |
| SATT063 | 4 | B2 | 113.1 |
| SATT109 | 4 | B2 | 118.0 |
| P10638B-2 | 4 | B2 | 120.0 |
| SATT560 | 4 | B2 | 137.4 |
| A183_1 | 4 | B2 | 139.0 |

Fig. 7 (cont.)

Chromosome C1

| Marker | Chrom. Number | Chrom. Name | Position (cM) |
|---|---|---|---|
| SATT565 | 5 | C1 | 0.0 |
| S0YGPATR | 5 | C1 | 21.0 |
| SCT_186 | 5 | C1 | 22.7 |
| SATT396 | 5 | C1 | 29.4 |
| SATT194 | 5 | C1 | 30.2 |
| SAT_337 | 5 | C1 | 43.8 |
| SAC1006 | 5 | C1 | 48.0 |
| SATT391 | 5 | C1 | 50.0 |
| SATT578 | 5 | C1 | 74.0 |
| SATT399 | 5 | C1 | 95.8 |
| SAT_085 | 5 | C1 | 96.5 |
| SATT361 | 5 | C1 | 96.5 |
| SATT139 | 5 | C1 | 97.3 |
| SATT661 | 5 | C1 | 97.8 |
| SATT661-TB | 5 | C1 | 97.8 |
| P10639A-1 | 5 | C1 | 98.0 |
| SATT161 | 5 | C1 | 99.0 |
| SATT190 | 5 | C1 | 99.0 |
| SATT294 | 5 | C1 | 105.4 |
| SATT195 | 5 | C1 | 108.2 |
| SATT670 | 5 | C1 | 109.2 |
| SATT670-TB | 5 | C1 | 109.2 |
| P2636C-2 | 5 | C1 | 110.0 |
| SATT476 | 5 | C1 | 110.0 |
| SAT_042 | 5 | C1 | 111.0 |
| SAT_311 | 5 | C1 | 117.6 |
| SAT_311-DB | 5 | C1 | 117.6 |
| SATT524 | 5 | C1 | 171.0 |
| SATT338 | 5 | C1 | 173.0 |
| SATT180 | 5 | C1 | 177.8 |
| SATT164 | 5 | C1 | 180.9 |

Chromosome C2

| Marker | Chrom. Number | Chrom. Name | Position (cM) |
|---|---|---|---|
| SATT227 | 6 | C2 | 25.4 |
| SATT640 | 6 | C2 | 28.6 |
| SATT640-TB | 6 | C2 | 28.7 |
| SAT_062 | 6 | C2 | 29.2 |
| SATT432 | 6 | C2 | 35.1 |
| SATT520 | 6 | C2 | 45.9 |
| SATT422 | 6 | C2 | 48.1 |
| SATT291 | 6 | C2 | 48.2 |
| SAT_336 | 6 | C2 | 51.3 |
| SATT457 | 6 | C2 | 53.4 |
| SATT170 | 6 | C2 | 77.9 |
| SATT322 | 6 | C2 | 84.6 |
| SAT_246 | 6 | C2 | 102.6 |
| SATT450 | 6 | C2 | 112.8 |
| SATT363 | 6 | C2 | 127.6 |
| SAT_076 | 6 | C2 | 128.5 |
| SATT286 | 6 | C2 | 128.5 |
| SAC1161 | 6 | C2 | 132.0 |
| SATT277 | 6 | C2 | 138.8 |
| SATT365 | 6 | C2 | 139.7 |
| SATT557 | 6 | C2 | 140.9 |
| SATT134 | 6 | C2 | 141.7 |
| SATT289 | 6 | C2 | 141.7 |
| SAT_312 | 6 | C2 | 143.5 |
| SATT100 | 6 | C2 | 143.6 |
| SATT319 | 6 | C2 | 145.8 |
| SAT_142-DB | 6 | C2 | 153.5 |
| SATT708 | 6 | C2 | 155.3 |
| SATT708-TB | 6 | C2 | 155.3 |
| SATT460 | 6 | C2 | 165.8 |
| P13073A-1 | 6 | C2 | 168.3 |
| SATT307 | 6 | C2 | 168.3 |
| SCT_028 | 6 | C2 | 168.3 |
| SATT433 | 6 | C2 | 170.5 |
| SATT316 | 6 | C2 | 171.9 |
| SATT202 | 6 | C2 | 173.9 |
| SATT371 | 6 | C2 | 188.7 |
| SATT357 | 6 | C2 | 193.5 |

Fig. 7 (cont.)

Chromosome D1a

| Marker | Chrom. Number | Chrom. Name | Position (cM) |
|---|---|---|---|
| SATT184 | 7 | D1a | 8.3 |
| P10636A-1 | 7 | D1a | 35.0 |
| SATT032 | 7 | D1a | 41.1 |
| SATT368 | 7 | D1a | 41.1 |
| SATT482 | 7 | D1a | 44.6 |
| SATT532 | 7 | D1a | 49.1 |
| SATT605 | 7 | D1a | 49.1 |
| SATT320 | 7 | D1a | 49.8 |
| SATT342 | 7 | D1a | 49.8 |
| SATT221 | 7 | D1a | 51.5 |
| SATT502 | 7 | D1a | 52.1 |
| SATT321 | 7 | D1a | 54.7 |
| SATT548 | 7 | D1a | 54.7 |
| SAT_353 | 7 | D1a | 62.3 |
| SATT402 | 7 | D1a | 67.0 |
| SATT603 | 7 | D1a | 67.5 |
| SATT179 | 7 | D1a | 67.8 |
| SATT254 | 7 | D1a | 67.8 |
| SATT267 | 7 | D1a | 68.6 |
| SATT383 | 7 | D1a | 68.6 |
| SATT295 | 7 | D1a | 69.8 |
| SATT515 | 7 | D1a | 69.8 |
| SATT203 | 7 | D1a | 73.1 |
| SATT580 | 7 | D1a | 74.0 |
| SATT283 | 7 | D1a | 75.9 |
| SATT370 | 7 | D1a | 75.9 |
| SATT507 | 7 | D1a | 80.3 |
| SAT_345 | 7 | D1a | 81.9 |
| SAT_110 | 7 | D1a | 82.0 |
| SAT_343 | 7 | D1a | 82.0 |
| SAT_106 | 7 | D1a | 83.5 |
| SATT198 | 7 | D1a | 84.2 |
| P10620A-1 | 7 | D1a | 85.0 |
| SATT077 | 7 | D1a | 87.9 |
| SATT436 | 7 | D1a | 89.3 |
| SATT468 | 7 | D1a | 90.3 |
| SAT_036 | 7 | D1a | 94.1 |
| SAT_305 | 7 | D1a | 110.8 |
| SATT129 | 7 | D1a | 129.2 |
| SATT147 | 7 | D1a | 129.2 |

Chromosome D1b

| Marker | Chrom. Number | Chrom. Name | Position (cM) |
|---|---|---|---|
| SATT216 | 8 | D1b | 0.0 |
| P13071A-1 | 8 | D1b | 10.0 |
| SAT_095 | 8 | D1b | 15.8 |
| SAT_351 | 8 | D1b | 19.1 |
| P10621B-2 | 8 | D1b | 20.0 |
| SATT157 | 8 | D1b | 28.0 |
| SAC1701 | 8 | D1b | 34.4 |
| SATT701 | 8 | D1b | 36.7 |
| SATT558 | 8 | D1b | 39.8 |
| SATT634 | 8 | D1b | 41.8 |
| SATT092 | 8 | D1b | 45.0 |
| SATT296 | 8 | D1b | 46.3 |
| SATT266 | 8 | D1b | 51.6 |
| SATT282 | 8 | D1b | 64.3 |
| SATT290 | 8 | D1b | 64.3 |
| SATT428 | 8 | D1b | 64.3 |
| SATT579 | 8 | D1b | 64.3 |
| SATT005 | 8 | D1b | 65.1 |
| SATT412 | 8 | D1b | 65.1 |
| SATT537 | 8 | D1b | 65.1 |
| SATT600 | 8 | D1b | 65.1 |
| SATT141 | 8 | D1b | 65.9 |
| SATT189 | 8 | D1b | 65.9 |
| SATT506 | 8 | D1b | 65.9 |
| SATT604 | 8 | D1b | 65.9 |
| P10637A-1 | 8 | D1b | 66.0 |
| SATT350 | 8 | D1b | 66.2 |
| SAT_135 | 8 | D1b | 67.0 |
| SATT041 | 8 | D1b | 72.0 |
| SATT546 | 8 | D1b | 76.1 |
| SATT172 | 8 | D1b | 92.2 |
| SATT274 | 8 | D1b | 95.6 |
| SAT_202 | 8 | D1b | 98.1 |
| SATT271 | 8 | D1b | 119.9 |
| P13072A-1 | 8 | D1b | 120.0 |

Fig. 7 (cont.)

Chromosome D2

| Marker | Chrom. Number | Chrom. Name | Position (cM) |
|---|---|---|---|
| SCTT008 | 9 | D2 | 0.0 |
| SATT328 | 9 | D2 | 9.2 |
| SATT135 | 9 | D2 | 34.7 |
| SATT458 | 9 | D2 | 34.7 |
| SATT014 | 9 | D2 | 37.6 |
| SATT498 | 9 | D2 | 40.7 |
| SATT486 | 9 | D2 | 41.6 |
| SATT372 | 9 | D2 | 46.3 |
| SATT002 | 9 | D2 | 59.3 |
| SATT154 | 9 | D2 | 65.3 |
| SATT582 | 9 | D2 | 66.9 |
| SATT443 | 9 | D2 | 72.7 |
| SATT397 | 9 | D2 | 76.8 |
| SATT208 | 9 | D2 | 80.8 |
| SATT447 | 9 | D2 | 84.0 |
| SAT_222-DB | 9 | D2 | 91.1 |
| SATT389 | 9 | D2 | 93.8 |
| SATT461 | 9 | D2 | 99.6 |
| SATT311 | 9 | D2 | 106.6 |
| SAT_114 | 9 | D2 | 107.8 |
| SATT226 | 9 | D2 | 107.8 |
| SATT514 | 9 | D2 | 107.8 |
| SATT528 | 9 | D2 | 109.5 |
| SATT464 | 9 | D2 | 110.4 |
| SAT_300 | 9 | D2 | 111.2 |
| SATT662 | 9 | D2 | 111.8 |
| SATT082 | 9 | D2 | 112.1 |
| SATT488 | 9 | D2 | 112.1 |
| SATT543 | 9 | D2 | 112.1 |
| SATT574 | 9 | D2 | 113.8 |
| SAT_001 | 9 | D2 | 120.2 |
| SATT301 | 9 | D2 | 121.8 |
| SAT_022 | 9 | D2 | 133.5 |
| SATT186 | 9 | D2 | 139.1 |
| SATT310 | 9 | D2 | 143.0 |
| SAT_326 | 9 | D2 | 147.4 |
| SATT031 | 9 | D2 | 148.3 |
| SATT413 | 9 | D2 | 148.3 |
| SATT672 | 9 | D2 | 149.1 |
| SATT256 | 9 | D2 | 154.8 |
| SATT386 | 9 | D2 | 154.8 |
| SCT_137 | 9 | D2 | 154.8 |

Chromosome E

| Marker | Chrom. Number | Chrom. Name | Position (cM) |
|---|---|---|---|
| SATT212 | 10 | E | 0.0 |
| SATT651 | 10 | E | 0.2 |
| SATT213 | 10 | E | 12.3 |
| SATT384 | 10 | E | 16.3 |
| SAT_112 | 10 | E | 18.3 |
| SATT411 | 10 | E | 22.5 |
| P13074A-1 | 10 | E | 40.0 |
| SAT_124 | 10 | E | 64.4 |
| SATT512 | 10 | E | 66.0 |
| P10624A-1 | 10 | E | 80.0 |
| SAG1135 | 10 | E | 95.0 |
| SATT573 | 10 | E | 98.0 |
| SATT598 | 10 | E | 98.0 |
| SATT185 | 10 | E | 99.9 |
| SAT_107 | 10 | E | 100.6 |
| SATT204 | 10 | E | 100.6 |
| SATT263 | 10 | E | 100.6 |
| SATT268 | 10 | E | 100.6 |
| SAT_380 | 10 | E | 100.7 |
| SATT491 | 10 | E | 101.0 |
| SATT602 | 10 | E | 101.0 |
| SATT151 | 10 | E | 102.2 |
| SATT355 | 10 | E | 102.2 |
| SATT452 | 10 | E | 102.2 |
| SATT045 | 10 | E | 103.5 |
| SAT_273 | 10 | E | 103.7 |
| SAT_273-DB | 10 | E | 103.7 |
| SATT369 | 10 | E | 116.5 |
| SATT685 | 10 | E | 117.1 |
| SAT_381 | 10 | E | 127.7 |
| SATT231 | 10 | E | 134.9 |
| SATT230 | 10 | E | 137.8 |

Fig. 7 (cont.)

Chromosome F

| Markerv | Chrom. Number | Chrom. Name | Position (cM) |
|---|---|---|---|
| SATT146 | 11 | F | 0.0 |
| SATT193 | 11 | F | 0.0 |
| SATT325 | 11 | F | 0.0 |
| SATT569 | 11 | F | 0.0 |
| SATT343 | 11 | F | 1.7 |
| SATT030 | 11 | F | 1.9 |
| SATT586 | 11 | F | 1.9 |
| SATT176 | 11 | F | 2.0 |
| SATT040 | 11 | F | 2.5 |
| SATT649 | 11 | F | 2.7 |
| SAT_262 | 11 | F | 6.9 |
| SATT269 | 11 | F | 12.4 |
| SATT252 | 11 | F | 16.2 |
| SATT423 | 11 | F | 16.4 |
| SATT348 | 11 | F | 18.0 |
| SATT149 | 11 | F | 19.3 |
| SATT160 | 11 | F | 22.4 |
| SAT_240-DB | 11 | F | 23.4 |
| SATT659-TB | 11 | F | 24.9 |
| SATT206 | 11 | F | 28.2 |
| S60817-TB | 11 | F | 30.0 |
| SATT516 | 11 | F | 50.7 |
| SATT425 | 11 | F | 56.4 |
| SATT374 | 11 | F | 57.5 |
| SATT595 | 11 | F | 57.5 |
| SAT_133 | 11 | F | 58.6 |
| S60602-TB | 11 | F | 65.0 |
| SATT114 | 11 | F | 80.6 |
| SAT_297 | 11 | F | 82.8 |
| P10782A-1 | 11 | F | 85.0 |
| P3436A-1 | 11 | F | 87.5 |
| P3436A-7 | 11 | F | 87.5 |
| P10598A-1 | 11 | F | 90.0 |
| SATT334 | 11 | F | 95.0 |
| SCT_033 | 11 | F | 110.2 |
| SAT_120 | 11 | F | 113.3 |
| SATT510 | 11 | F | 114.8 |
| SAT_317 | 11 | F | 117.6 |
| SATT335 | 11 | F | 126.2 |
| SATT362 | 11 | F | 128.3 |
| SATT072 | 11 | F | 131.9 |
| SCT_188 | 11 | F | 133.1 |
| SAT_313 | 11 | F | 142.7 |
| SATT144 | 11 | F | 157.8 |
| SATT554 | 11 | F | 159.2 |
| SATT522 | 11 | F | 165.8 |
| SATT218 | 11 | F | 169.2 |
| P9026A-1 | 11 | F | 175.0 |
| SATT395 | 11 | F | 178.2 |
| SAT_090 | 11 | F | 180.0 |
| SAT_074 | 11 | F | 181.8 |
| SATT656 | 11 | F | 185.0 |
| K102_2 | 11 | F | 199.1 |

Fig. 7 (cont.)

Chromosome G

| Marker | Chrom. Number | Chrom. Name | Position (cM) |
|---|---|---|---|
| S60239-TB | 12 | G | 0.0 |
| SATT038 | 12 | G | 1.0 |
| SATT309 | 12 | G | 1.9 |
| P10646A-1 | 12 | G | 2.0 |
| P10355B-1 | 12 | G | 3.0 |
| P5219A-1 | 12 | G | 3.0 |
| P5219A-2 | 12 | G | 3.0 |
| RHG1-1 | 12 | G | 3.0 |
| RHG1-2 | 12 | G | 3.0 |
| P7659A-1 | 12 | G | 4.0 |
| P7659A-2 | 12 | G | 4.0 |
| SAT_163 | 12 | G | 7.0 |
| S60509-CB | 12 | G | 7.0 |
| SATT570 | 12 | G | 7.7 |
| SATT356 | 12 | G | 8.5 |
| SATT217 | 12 | G | 13.2 |
| SATT130 | 12 | G | 13.5 |
| SATT235 | 12 | G | 14.2 |
| P10633A-1 | 12 | G | 15.0 |
| SAT_315 | 12 | G | 21.9 |
| SAT_131 | 12 | G | 23.3 |
| SATT324 | 12 | G | 25.9 |
| SATT394 | 12 | G | 51.6 |
| SAT_308 | 12 | G | 51.7 |
| SATT115 | 12 | G | 53.0 |
| SATT594 | 12 | G | 61.3 |
| SAT_088 | 12 | G | 63.3 |
| SATT427 | 12 | G | 63.3 |
| SATT533 | 12 | G | 66.1 |
| SATT564 | 12 | G | 66.1 |
| SAT_094 | 12 | G | 67.0 |
| SATT504 | 12 | G | 67.0 |
| SATT303 | 12 | G | 71.6 |
| SATT352 | 12 | G | 72.4 |
| SATT566 | 12 | G | 72.4 |
| SATT131 | 12 | G | 74.2 |
| SATT340 | 12 | G | 77.4 |
| SATT501 | 12 | G | 78.5 |
| SAT_260 | 12 | G | 96.3 |
| SATT138 | 12 | G | 98.0 |
| SATT505 | 12 | G | 100.1 |
| SAT_203 | 12 | G | 100.3 |
| SATT199 | 12 | G | 100.8 |
| SATT400 | 12 | G | 100.8 |
| SATT012 | 12 | G | 101.6 |
| SATT503 | 12 | G | 103.2 |
| SATT517 | 12 | G | 103.2 |
| SATT288 | 12 | G | 112.9 |
| SATT612 | 12 | G | 116.5 |
| P10783A-1 | 12 | G | 125.0 |

| Marker | Chrom. Number | Chrom. Name | Position (cM) |
|---|---|---|---|
| SCT_199 | 12 | G | 134.3 |
| SCT_199-DB | 12 | G | 134.3 |
| SATT472 | 12 | G | 135.0 |
| SATT191 | 12 | G | 137.0 |
| SAT_117 | 12 | G | 138.4 |
| P10792A-1 | 12 | G | 145.0 |
| SCT_187 | 12 | G | 155.0 |
| A681_1 | 12 | G | 166.0 |

Fig. 7 (cont.)

Chromosome H

| Marker | Chrom. Number | Chrom. Name | Position (cM) |
|---|---|---|---|
| SATT666 | 13 | H | -8.0 |
| SAT_200 | 13 | H | -5.0 |
| SATT353 | 13 | H | 0.0 |
| SAT_127 | 13 | H | 27.6 |
| SATT568 | 13 | H | 27.6 |
| SATT192 | 13 | H | 41.1 |
| SATT442 | 13 | H | 42.3 |
| SCTT009 | 13 | H | 45.2 |
| SATT469 | 13 | H | 68.5 |
| SATT541 | 13 | H | 68.5 |
| SAT_122 | 13 | H | 70.2 |
| SAT_118 | 13 | H | 71.1 |
| SATT279 | 13 | H | 77.3 |
| SATT314 | 13 | H | 77.3 |
| SATT222 | 13 | H | 78.1 |
| SATT253 | 13 | H | 78.1 |
| SATT629 | 13 | H | 84.3 |
| SATT302 | 13 | H | 110.4 |
| SATT637 | 13 | H | 115.3 |
| SATT142 | 13 | H | 116.9 |
| SATT293 | 13 | H | 116.9 |
| SATT181 | 13 | H | 125.3 |
| P13158A-1 | 13 | H | 130.0 |
| SAT_218 | 13 | H | 140.1 |
| SATT434 | 13 | H | 152.4 |
| K007_1 | 13 | H | 162.9 |

Chromosome I

| Marker | Chrom. Number | Chrom. Name | Position (cM) |
|---|---|---|---|
| SATT451 | 14 | I | 0.0 |
| SATT571 | 14 | I | 0.0 |
| SATT419 | 14 | I | 2.4 |
| SATT367 | 14 | I | 9.8 |
| SATT127 | 14 | I | 15.5 |
| SATT587 | 14 | I | 16.5 |
| SATT614 | 14 | I | 16.5 |
| SCTT012 | 14 | I | 16.6 |
| SATT239 | 14 | I | 25.3 |
| SATT496 | 14 | I | 25.3 |
| SATT354 | 14 | I | 37.2 |
| SAT_105 | 14 | I | 57.9 |
| SATT270 | 14 | I | 57.9 |
| SATT049 | 14 | I | 63.4 |
| SAG1045 | 14 | I | 65.0 |
| SAT_104 | 14 | I | 70.0 |
| SATT330 | 14 | I | 74.0 |
| SATT292 | 14 | I | 77.4 |
| SAT_324 | 14 | I | 79.5 |
| SATT148 | 14 | I | 84.5 |
| SATT162 | 14 | I | 90.5 |
| SAT_299 | 14 | I | 98.4 |
| SATT440 | 14 | I | 114.2 |
| SCT_189 | 14 | I | 114.2 |
| P10640A-1 | 14 | I | 115.0 |

Fig. 7 (cont.)

Chromosome J

| Marker | Chrom. Number | Chrom. Name | Position (cM) |
|---|---|---|---|
| SATT405 | 15 | J | 9.8 |
| SATT249 | 15 | J | 10.5 |
| SATT287 | 15 | J | 13.1 |
| SATT285 | 15 | J | 19.5 |
| SCT_046 | 15 | J | 19.5 |
| SAG1223 | 15 | J | 19.6 |
| SAC1699 | 15 | J | 26.4 |
| P10634A-1 | 15 | J | 30.0 |
| SCT_065 | 15 | J | 61.3 |
| SATT414 | 15 | J | 63.6 |
| SATT596 | 15 | J | 63.6 |
| SCAA003 | 15 | J | 63.6 |
| SATT654 | 15 | J | 66.9 |
| SATT280 | 15 | J | 67.2 |
| SATT456 | 15 | J | 67.2 |
| SATT406 | 15 | J | 68.0 |
| SAT_093 | 15 | J | 70.8 |
| SATT380 | 15 | J | 70.8 |
| SATT183 | 15 | J | 72.6 |
| SATT529 | 15 | J | 74.4 |
| SCT_001 | 15 | J | 75.8 |
| SAT_366 | 15 | J | 83.5 |
| SATT244 | 15 | J | 105.5 |
| P2447B-2 | 15 | J | 110.0 |
| SATT431 | 15 | J | 118.0 |
| PCR2_176 | 15 | J | 124.8 |
| SATT712 | 15 | J | 128.9 |

Chromosome K

| Marker | Chrom. Number | Chrom. Name | Position (cM) |
|---|---|---|---|
| SATT667 | 16 | K | 0.0 |
| SATT539 | 16 | K | 4.3 |
| SATT242 | 16 | K | 17.9 |
| SAT_119 | 16 | K | 20.3 |
| SAG1935 | 16 | K | 39.6 |
| SATT102 | 16 | K | 44.0 |
| SATT137 | 16 | K | 50.3 |
| SATT178 | 16 | K | 55.1 |
| SATT055 | 16 | K | 59.4 |
| SAC1730 | 16 | K | 63.7 |
| SATT349 | 16 | K | 64.6 |
| SATT555 | 16 | K | 65.9 |
| SATT247 | 16 | K | 66.7 |
| SATT381 | 16 | K | 69.7 |
| SATT337 | 16 | K | 70.5 |
| SATT417 | 16 | K | 70.9 |
| SATT441 | 16 | K | 70.9 |
| SATT552 | 16 | K | 70.9 |
| SATT046 | 16 | K | 71.9 |
| P10651A-1 | 16 | K | 72.0 |
| SATT264 | 16 | K | 72.0 |
| SATT167 | 16 | K | 72.6 |
| SATT375 | 16 | K | 72.8 |
| SATT544 | 16 | K | 72.8 |
| SATT518 | 16 | K | 73.6 |
| SAT_116 | 16 | K | 79.2 |
| SATT326 | 16 | K | 82.2 |
| SATT628 | 16 | K | 82.3 |
| SAT_349 | 16 | K | 83.0 |
| SATT617 | 16 | K | 83.7 |
| SATT559 | 16 | K | 85.2 |
| SATT240 | 16 | K | 85.8 |
| SAT_044 | 16 | K | 86.9 |
| SATT001 | 16 | K | 95.9 |
| SAT_043 | 16 | K | 108.3 |
| SATT273 | 16 | K | 120.0 |
| SAT_111 | 16 | K | 122.0 |
| SATT499 | 16 | K | 134.5 |
| P10618A-1 | 16 | K | 144.0 |
| SATT475 | 16 | K | 144.3 |
| SATT260 | 16 | K | 145.1 |
| SATT196 | 16 | K | 164.8 |
| SAT_020 | 16 | K | 165.4 |
| S60222-TB | 16 | K | 170.0 |
| SAT_126 | 16 | K | 175.6 |
| SATT588 | 16 | K | 184.6 |

Fig. 7 (cont.)

Chromosome L

| Marker | Chrom. Number | Chrom. Name | Position (cM) |
|---|---|---|---|
| SATT495 | 17 | L | 4.5 |
| SATT232 | 17 | L | 7.4 |
| SATT446 | 17 | L | 9.2 |
| P10649C-3 | 17 | L | 12.5 |
| SATT182 | 17 | L | 13.4 |
| SAT_301 | 17 | L | 15.6 |
| SAT_071 | 17 | L | 19.7 |
| SATT238 | 17 | L | 19.7 |
| SATT388 | 17 | L | 22.2 |
| SATT143 | 17 | L | 31.8 |
| SAT_134 | 17 | L | 32.4 |
| SATT523 | 17 | L | 32.4 |
| SATT278 | 17 | L | 33.2 |
| SATT418 | 17 | L | 33.9 |
| SATT711 | 17 | L | 34.0 |
| SATT398 | 17 | L | 34.6 |
| SATT497 | 17 | L | 42.3 |
| SATT313 | 17 | L | 43.9 |
| SATT613 | 17 | L | 45.1 |
| SATT284 | 17 | L | 47.7 |
| SATT462 | 17 | L | 49.3 |
| SAT_340 | 17 | L | 65.2 |
| SATT156 | 17 | L | 65.8 |
| SATT481 | 17 | L | 65.8 |
| SCT_010 | 17 | L | 68.5 |
| SATT076 | 17 | L | 72.3 |
| SATT265 | 17 | L | 75.0 |
| SATT527 | 17 | L | 75.7 |
| SATT561 | 17 | L | 75.7 |
| SATT166 | 17 | L | 77.1 |
| SATT448 | 17 | L | 78.0 |
| SATT678 | 17 | L | 80.9 |
| SAT_099 | 17 | L | 89.4 |
| SAG1055 | 17 | L | 95.0 |
| S60375-TB | 17 | L | 100.0 |
| SATT006 | 17 | L | 104.7 |
| SATT229 | 17 | L | 107.7 |
| SATT373 | 17 | L | 118.0 |
| SATT513 | 17 | L | 118.6 |
| P12394A-1 | 17 | L | 124.5 |

Chromosome M

| Marker | Chrom. Number | Chrom. Name | Position (cM) |
|---|---|---|---|
| GMSC514 | 18 | M | 0.0 |
| SATT404 | 18 | M | 2.7 |
| SATT636 | 18 | M | 7.9 |
| SATT590 | 18 | M | 12.4 |
| SATT201 | 18 | M | 17.2 |
| SATT150 | 18 | M | 20.8 |
| SATT299 | 18 | M | 30.0 |
| SATT567 | 18 | M | 41.0 |
| SATT540 | 18 | M | 45.5 |
| SATT463 | 18 | M | 67.0 |
| SATT245 | 18 | M | 73.0 |
| SATT323 | 18 | M | 77.6 |
| SATT220 | 18 | M | 78.9 |
| SAG1048 | 18 | M | 84.2 |
| SAT_258 | 18 | M | 85.1 |
| SAT_003 | 18 | M | 87.6 |
| SATT536 | 18 | M | 87.6 |
| SATT175 | 18 | M | 91.1 |
| S60149-TB | 18 | M | 93.0 |
| SATT494 | 18 | M | 94.4 |
| SCT_147 | 18 | M | 95.6 |
| SAT_256 | 18 | M | 96.6 |
| SATT677 | 18 | M | 98.1 |
| SATT655 | 18 | M | 99.3 |
| SATT655-TB | 18 | M | 99.3 |
| SATT680 | 18 | M | 100.5 |
| SATT306 | 18 | M | 106.0 |
| SAC1677 | 18 | M | 110.0 |
| P10615A-1 | 18 | M | 115.0 |
| SATT551 | 18 | M | 127.3 |
| SAT_121 | 18 | M | 131.7 |
| SATT250 | 18 | M | 139.4 |
| SATT618 | 18 | M | 142.1 |
| SATT346 | 18 | M | 143.5 |
| SATT336 | 18 | M | 173.5 |
| SAT_330 | 18 | M | 180.5 |
| SAT_330-DB | 18 | M | 180.5 |

Fig. 7 (cont.)

Chromosome N

| Marker | Chrom. Number | Chrom. Name | Position (cM) |
|---|---|---|---|
| SATT631 | 19 | N | 14.9 |
| SATT159 | 19 | N | 15.5 |
| SATT152 | 19 | N | 16.3 |
| SATT009 | 19 | N | 17.2 |
| P13069A-1 | 19 | N | 20.0 |
| P5467A-1 | 19 | N | 25.0 |
| P5467A-2 | 19 | N | 25.0 |
| SATT530 | 19 | N | 25.0 |
| SATT683 | 19 | N | 32.8 |
| SATT675 | 19 | N | 33.1 |
| SATT584 | 19 | N | 35.4 |
| SATT393 | 19 | N | 36.3 |
| SATT485 | 19 | N | 36.3 |
| SAT_084 | 19 | N | 38.3 |
| P3050A-2 | 19 | N | 40.0 |
| SAT_275 | 19 | N | 40.2 |
| SAT_275-DB | 19 | N | 40.2 |
| SATT125 | 19 | N | 43.7 |
| SAT_033 | 19 | N | 54.8 |
| SATT387 | 19 | N | 61.2 |
| SATT521 | 19 | N | 75.2 |
| SATT549 | 19 | N | 80.2 |
| SATT660 | 19 | N | 83.4 |
| SATT339 | 19 | N | 88.6 |
| SATT237 | 19 | N | 90.1 |
| SATT255 | 19 | N | 92.2 |
| SAT_304 | 19 | N | 92.6 |
| SAT_091 | 19 | N | 95.5 |
| SATT234 | 19 | N | 98.0 |
| SATT257 | 19 | N | 113.0 |
| SATT410 | 19 | N | 118.5 |
| A802_1 | 19 | N | 137.0 |

Chromosome O

| Marker | Chrom. Number | Chrom. Name | Position (cM) |
|---|---|---|---|
| SAT_132 | 20 | O | 0.0 |
| P12396A-1 | 20 | O | 2.4 |
| SATT358 | 20 | O | 2.4 |
| SATT487 | 20 | O | 6.3 |
| SATT500 | 20 | O | 10.9 |
| SATT492 | 20 | O | 12.6 |
| SATT445 | 20 | O | 13.0 |
| SAT_318 | 20 | O | 18.3 |
| SATT259 | 20 | O | 37.7 |
| SATT347 | 20 | O | 39.0 |
| SAC1634 | 20 | O | 42.8 |
| SATT420 | 20 | O | 60.5 |
| SATT576 | 20 | O | 65.1 |
| SATT094 | 20 | O | 66.7 |
| SATT608 | 20 | O | 66.7 |
| SATT219 | 20 | O | 67.0 |
| SATT466 | 20 | O | 67.5 |
| SATT550 | 20 | O | 67.5 |
| SAT_291 | 20 | O | 68.4 |
| SATT479 | 20 | O | 68.4 |
| SATT585 | 20 | O | 68.4 |
| SATT633 | 20 | O | 68.9 |
| SATT262 | 20 | O | 69.2 |
| SATT473 | 20 | O | 69.2 |
| SATT173 | 20 | O | 78.0 |
| SATT345 | 20 | O | 78.0 |
| SATT563 | 20 | O | 80.0 |
| SATT478 | 20 | O | 81.7 |
| SATT477 | 20 | O | 103.8 |
| SATT592 | 20 | O | 120.5 |
| SATT581 | 20 | O | 125.0 |
| SATT331 | 20 | O | 127.9 |
| P11070A-1 | 20 | O | 130.0 |
| SAT_038 | 20 | O | 153.3 |
| SATT153 | 20 | O | 153.3 |
| SATT243 | 20 | O | 155.1 |
| SAT_108 | 20 | O | 164.5 |
| SAT_109 | 20 | O | 166.3 |
| P8230A-1 | 20 | O | 175.7 |

Fig. 7 (cont.)

SEQUENCE LISTING

```
<160> NUMBER OF SEQ ID NOS: 42

<210> SEQ ID NO 1
<211> LENGTH: 22
<212> TYPE: DNA
<213> ORGANISM: Artificial
<220> FEATURE:
<223> OTHER INFORMATION: oligonucleotide primer

<400> SEQUENCE: 1
tttgtttgat ctatgcactt gc                                              22
```

-continued

<210> SEQ ID NO 2
<211> LENGTH: 20
<212> TYPE: DNA
<213> ORGANISM: Artificial
<220> FEATURE:
<223> OTHER INFORMATION: oligonucleotide primer

<400> SEQUENCE: 2
gccaagtcac acacaccaag                                              20

<210> SEQ ID NO 3
<211> LENGTH: 27
<212> TYPE: DNA
<213> ORGANISM: Artificial
<220> FEATURE:
<223> OTHER INFORMATION: oligonucleotide primer

<400> SEQUENCE: 3
tgctgcagcg tgtctgtagt ataattt                                      27

<210> SEQ ID NO 4
<211> LENGTH: 23
<212> TYPE: DNA
<213> ORGANISM: Artificial
<220> FEATURE:
<223> OTHER INFORMATION: oligonucleotide primer

<400> SEQUENCE: 4
ggcacaacca tcaccacctt att                                          23

<210> SEQ ID NO 5
<211> LENGTH: 22
<212> TYPE: DNA
<213> ORGANISM: Artificial
<220> FEATURE:
<223> OTHER INFORMATION: oligonucleotide primer

<400> SEQUENCE: 5
gaaacccgaa acgcaaaatc tc                                           22

<210> SEQ ID NO 6
<211> LENGTH: 22
<212> TYPE: DNA
<213> ORGANISM: Artificial
<220> FEATURE:
<223> OTHER INFORMATION: oligonucleotide primer

<400> SEQUENCE: 6
gaagaaaacg cgaataaccc ca                                           22

<210> SEQ ID NO 7
<211> LENGTH: 24
<212> TYPE: DNA
<213> ORGANISM: Artificial
<220> FEATURE:
<223> OTHER INFORMATION: oligonucleotide primer

<400> SEQUENCE: 7
tgctcaaagg gtcaatttct ttcc                                         24

<210> SEQ ID NO 8
<211> LENGTH: 28
<212> TYPE: DNA
<213> ORGANISM: Artificial
<220> FEATURE:
<223> OTHER INFORMATION: oligonucleotide primer

<400> SEQUENCE: 8
tgtgtaattt ctatcacctt attgtgcc                                        28

<210> SEQ ID NO 9
<211> LENGTH: 23
<212> TYPE: DNA
<213> ORGANISM: Artificial
<220> FEATURE:
<223> OTHER INFORMATION: oligonucleotide primer

<400> SEQUENCE: 9
cctcttcaac aaaaacaccc gtt                                             23

<210> SEQ ID NO 10
<211> LENGTH: 22
<212> TYPE: DNA
<213> ORGANISM: Artificial
<220> FEATURE:
<223> OTHER INFORMATION: oligonucleotide primer

<400> SEQUENCE: 10 gaccccagc ttctcattct ca                                               22

<210> SEQ ID NO 11
<211> LENGTH: 22
<212> TYPE: DNA
<213> ORGANISM: Artificial
<220> FEATURE:
<223> OTHER INFORMATION: oligonucleotide primer

<400> SEQUENCE: 11
acctcggtta ttacggcctc ca                                              22

<210> SEQ ID NO 12
<211> LENGTH: 22
<212> TYPE: DNA
<213> ORGANISM: Artificial
<220> FEATURE:
<223> OTHER INFORMATION: oligonucleotide primer

<400> SEQUENCE: 12
aattgctaca ccaccacacc aa                                              22

<210> SEQ ID NO 13
<211> LENGTH: 22
<212> TYPE: DNA
<213> ORGANISM: Artificial
<220> FEATURE:
<223> OTHER INFORMATION: oligonucleotide primer

<400> SEQUENCE: 13
tgctcatgtg gtcctaccca ga                                              22

<210> SEQ ID NO 14
<211> LENGTH: 26
<212> TYPE: DNA
<213> ORGANISM: Artificial
<220> FEATURE:
<223> OTHER INFORMATION: oligonucleotide primer

<400> SEQUENCE: 14
cgctatccct ttgtattttc ttttgc                                          26

<210> SEQ ID NO 15

<211> LENGTH: 23
<212> TYPE: DNA
<213> ORGANISM: Artificial
<220> FEATURE:
<223> OTHER INFORMATION: oligonucleotide primer

<400> SEQUENCE: 15
tgctgcttgt gtttggttga tct                                          23

<210> SEQ ID NO 16
<211> LENGTH: 22
<212> TYPE: DNA
<213> ORGANISM: Artificial
<220> FEATURE:
<223> OTHER INFORMATION: oligonucleotide primer

<400> SEQUENCE: 16
catatcctgc cccccaatt at                                            22

<210> SEQ ID NO 17
<211> LENGTH: 23
<212> TYPE: DNA
<213> ORGANISM: Artificial
<220> FEATURE:
<223> OTHER INFORMATION: oligonucleotide primer

<400> SEQUENCE: 17
tccttggggt gaattgtttt tca                                          23

<210> SEQ ID NO 18
<211> LENGTH: 22
<212> TYPE: DNA
<213> ORGANISM: Artificial
<220> FEATURE:
<223> OTHER INFORMATION: oligonucleotide primer

<400> SEQUENCE: 18
ccttcttttg acatggggcc ta                                           22

<210> SEQ ID NO 19
<211> LENGTH: 22
<212> TYPE: DNA
<213> ORGANISM: Artificial
<220> FEATURE:
<223> OTHER INFORMATION: oligonucleotide primer

<400> SEQUENCE: 19
tcgcgctgaa gatccgagta gt                                           22

<210> SEQ ID NO 20
<211> LENGTH: 26
<212> TYPE: DNA
<213> ORGANISM: Artificial
<220> FEATURE:
<223> OTHER INFORMATION: oligonucleotide primer

<400> SEQUENCE: 20
tcagcataaa accattaaaa gcaaaa                                       26

<210> SEQ ID NO 21
<211> LENGTH: 23
<212> TYPE: DNA
<213> ORGANISM: Artificial
<220> FEATURE:
<223> OTHER INFORMATION: oligonucleotide primer

<400> SEQUENCE: 21
cagttgattt tgttttttcg gca                                           23

<210> SEQ ID NO 22
<211> LENGTH: 22
<212> TYPE: DNA
<213> ORGANISM: Artificial
<220> FEATURE:
<223> OTHER INFORMATION: oligonucleotide primer

<400> SEQUENCE: 22
cacgcgcatc agctttgtag ag                                            22

<210> SEQ ID NO 23
<211> LENGTH: 25
<212> TYPE: DNA
<213> ORGANISM: Artificial
<220> FEATURE:
<223> OTHER INFORMATION: oligonucleotide primer

<400> SEQUENCE: 23
caccactcgt atccttcaca agagc                                         25

<210> SEQ ID NO 24
<211> LENGTH: 22
<212> TYPE: DNA
<213> ORGANISM: Artificial
<220> FEATURE:
<223> OTHER INFORMATION: oligonucleotide primer

<400> SEQUENCE: 24
gccagcagcc tgttcagttt tt                                            22

<210> SEQ ID NO 25
<211> LENGTH: 19
<212> TYPE: DNA
<213> ORGANISM: Artificial
<220> FEATURE:
<223> OTHER INFORMATION: oligonucleotide primer

<400> SEQUENCE: 25
tggcagtggg tagtgaatg                                                19

<210> SEQ ID NO 26
<211> LENGTH: 23
<212> TYPE: DNA
<213> ORGANISM: Artificial
<220> FEATURE:
<223> OTHER INFORMATION: oligonucleotide primer

<400> SEQUENCE: 26
aaagatggct gactttgttt aca                                           23

<210> SEQ ID NO 27
<211> LENGTH: 26
<212> TYPE: DNA
<213> ORGANISM: Artificial
<220> FEATURE:
<223> OTHER INFORMATION: oligonucleotide primer

<400> SEQUENCE: 27
ttggatctca tattcaaact ttcaag                                        26

<210> SEQ ID NO 28
<211> LENGTH: 26
<212> TYPE: DNA

```
<213> ORGANISM: Artificial
<220> FEATURE:
<223> OTHER INFORMATION: oligonucleotide primer

<400> SEQUENCE: 28
ctgcaaattt gatgcacatg tgtcta                                    26

<210> SEQ ID NO 29
<211> LENGTH: 22
<212> TYPE: DNA
<213> ORGANISM: Artificial
<220> FEATURE:
<223> OTHER INFORMATION: oligonucleotide primer

<400> SEQUENCE: 29
gacctcgctc tctgtttctc at                                        22

<210> SEQ ID NO 30
<211> LENGTH: 22
<212> TYPE: DNA
<213> ORGANISM: Artificial
<220> FEATURE:
<223> OTHER INFORMATION: oligonucleotide primer

<400> SEQUENCE: 30
ggtgaccacc cctattcctt at                                        22

<210> SEQ ID NO 31
<211> LENGTH: 22
<212> TYPE: DNA
<213> ORGANISM: Artificial
<220> FEATURE:
<223> OTHER INFORMATION: oligonucleotide primer

<400> SEQUENCE: 31
gcgtggaatg agacgtaacc aa                                        22

<210> SEQ ID NO 32
<211> LENGTH: 28
<212> TYPE: DNA
<213> ORGANISM: Artificial
<220> FEATURE:
<223> OTHER INFORMATION: oligonucleotide primer

<400> SEQUENCE: 32
gcataatggt ctaataaaag tggagacc                                  28

<210> SEQ ID NO 33
<211> LENGTH: 21
<212> TYPE: DNA
<213> ORGANISM: Artificial
<220> FEATURE:
<223> OTHER INFORMATION: oligonucleotide primer

<400> SEQUENCE: 33
aatgctttgg tcgttgcatt g                                         21

<210> SEQ ID NO 34
<211> LENGTH: 23
<212> TYPE: DNA
<213> ORGANISM: Artificial
<220> FEATURE:
<223> OTHER INFORMATION: oligonucleotide primer

<400> SEQUENCE: 34
tggtatcggg agattttttc agc                                       23
```

```
<210> SEQ ID NO 35
<211> LENGTH: 36
<212> TYPE: DNA
<213> ORGANISM: Artificial
<220> FEATURE:
<223> OTHER INFORMATION: oligonucleotide primer

<400> SEQUENCE: 35
cccccaacaa aactaaaaat agaaccctca acaacc                                  36

<210> SEQ ID NO 36
<211> LENGTH: 35
<212> TYPE: DNA
<213> ORGANISM: Artificial
<220> FEATURE:
<223> OTHER INFORMATION: oligonucleotide primer

<400> SEQUENCE: 36
ggtccaagaa cattatgatc ttgaacaatc ttcac                                   35

<210> SEQ ID NO 37
<211> LENGTH: 33
<212> TYPE: DNA
<213> ORGANISM: Artificial
<220> FEATURE:
<223> OTHER INFORMATION: oligonucleotide primer

<400> SEQUENCE: 37
catgaagctc caccatttgc tagtacatga aac                                     33

<210> SEQ ID NO 38
<211> LENGTH: 33
<212> TYPE: DNA
<213> ORGANISM: Artificial
<220> FEATURE:
<223> OTHER INFORMATION: oligonucleotide primer

<400> SEQUENCE: 38
ccagagttac caaccatct gtgagaaata tcc                                      33

<210> SEQ ID NO 39
<211> LENGTH: 12
<212> TYPE: DNA
<213> ORGANISM: Artificial
<220> FEATURE:
<223> OTHER INFORMATION: oligonucleotide probe

<400> SEQUENCE: 39
tgtgacaacc ga                                                            12

<210> SEQ ID NO 40
<211> LENGTH: 11
<212> TYPE: DNA
<213> ORGANISM: Artificial
<220> FEATURE:
<223> OTHER INFORMATION: oligonucleotide probe

<400> SEQUENCE: 40
gtgacacaac c                                                             11

<210> SEQ ID NO 41
<211> LENGTH: 12
<212> TYPE: DNA
<213> ORGANISM: Artificial
<220> FEATURE:
```

```
<223> OTHER INFORMATION: oligonucleotide probe

<400> SEQUENCE: 41
gaggagatgt ag                                                          12

<210> SEQ ID NO 42
<211> LENGTH: 12
<212> TYPE: DNA
<213> ORGANISM: Artificial
<220> FEATURE:
<223> OTHER INFORMATION: oligonucleotide probe

<400> SEQUENCE: 42
gaggaaatgt ag                                                          12
```

GENETIC LOCI ASSOCIATED WITH *SCLEROTINIA* TOLERANCE IN SOYBEAN

CROSS-REFERENCE TO RELATED APPLICATIONS

This application claims priority to and benefit of U.S. Provisional Patent Application Ser. No. 60/629,028, filed on Nov. 17, 2004, and U.S. Provisional Patent Application Ser. No. 60/629,029, filed on Nov. 17, 2004, the specifications of which are hereby incorporated by reference in their entirety.

FIELD OF THE INVENTION

The invention relates to compositions and methods for identifying soybean plants that are tolerant, have improved tolerance, have reduced susceptibility or are susceptible to *Sclerotinia* infection (the causative agent of white mold, also called stem rot), where the methods use molecular genetic markers to identify, select and/or construct disease-tolerant plants. The invention also relates to soybean plants that display tolerance or improved tolerance to *Sclerotinia* infection that are generated by the methods of the invention.

BACKGROUND OF THE INVENTION

Soybean, a legume, has become the world's primary source of seed oil and seed protein. In addition, its utilization is being expanded to the industrial, manufacturing and pharmaceutical sectors. Soybean productivity is a vital agricultural and economic consideration. Unfortunately, soybean is host to one of the widest ranges of infectious pathogens of all crops. More than a hundred different pathogens are known to affect soybean plants, some of which pose significant economic threats. Improving soybean disease tolerance to these many pathogens is crucial to preventing yield losses.

*Sclerotinia* and Soybean White Mold

*Sclerotinia* sp. stem rot in soybean, alternatively know as white mold or *Sclerotinia* white mold, is caused by the soil-borne fungal pathogen *Sclerotinia sclerotiorum* (Lib.) de Bary. The disease was first reported in Hungary in 1924, and since been reported in many other countries. It was first reported in the United States in 1946. *Sclerotinia* stem rot caused an estimated yield loss of $6.4 \times 10^5$ metric tons in the USA during 1994 (Wrether et al. (1997) *Plant Dis.*, 81:107-110). Yield has been shown to be inversely correlated with the percent incidence of *Sclerotinia* stem rot. Yield loss has been estimated at 250 kg/ha for each 10% increment in diseased plants (Grau and Hartman (1999) *Compendium of Soybean Diseases*, 4$^{th}$ ed. APS Press, St. Paul, Minn., USA, pp. 46-48). In severe cases, the disease can cause more than 50 percent yield reduction in commercial production fields. *Sclerotinia* stem rot is now a recognized economic concern (Wrather et al., (1997) *Plant Dis.*, 81:107-110), and is considered the second most important cause of soybean yield loss, surpassed only by soybean cyst nematode.

The *S. sclerotiorum* fungus overwinters in the soil and plant debris as special survival structures termed sclerotia, which have the appearance of mouse-droppings. Sclerotia can survive in or on the soil for at least seven years in the absence of host plants. Under favorable conditions, the sclerotia germinate to produce apothecia, which eventually produce ascospores that infect soybean plants via flowers (Grau (1988) *Am Phytopathol Soc*, St. Paul, Minn., USA pp 56-66). The ascospores germinate under adequate moisture condition and use the flower petals as a nutrient base. Stem lesions originate at leaf axils where flowers are positioned and advance up and down the stem. The fungus produces oxalic acid and other chemicals which diffuse into plant tissue and kill the plant cells. After the plant cells die, the fungus absorbs nutrients from the dead tissue and continues to grow on and through the plant. Once the fungus girdles a stem, the transport of water, mineral nutrients, and photosynthates to developing pods is disrupted, and all plant tissue up from the infection dies. The symptoms of the *Sclerotinia* stem rot begin to develop at growth stages R2 and R3. Lesions are most frequently on the main stem and eventually completely encircle the stem, resulting in reduced pod development and reduced pod fill above the stem lesions, ultimately generating yield reductions.

Soybean cultivars show large variations in resistance/susceptability to *Sclerotinia* stem rot (Kim et al. (1999) *Crop Sci* 39:64-68). So far, however, no soybean genotypes with complete resistance to *S. sclerotiorum* have been identified. Classical breeding for *Sclerotinia* stem rot tolerance and/or resistance via traditional approaches has been difficult and not entirely successful (Kim et al., (1999) Crop Sci., 39:64-68; Gondran and Leclercq, (1993) Agronomie 13(2):85-94; Nelson et al., (1991) Plant Dis., 75:662-665; Chun et al., (1987) Plant Dis., 71:811-815; Boland and Hall (1987) Plant Dis., 71:934-936). In the absence of complete resistance, partial resistance can also provide economically useful disease control and is a breeding objective in many soybean improvement programs.

A common method of protecting soybean plants from *Sclerotinia* white mold utilizes the selection of specific resistance genes. Plant breeders manipulate specific resistance genes in an attempt to produce plants that are resistant to infection, or limit the extent of the infection. Unfortunately, as breeders evolve increasingly resistant strains, the host range of the pathogen similarly evolves to adapt to the changing genetic constitution of the host. Thus, resistant soybean strains produced by plant breeders are effective only for a finite period and eventually fail.

An alternative approach is to identify plants that show tolerance to a particular pathogen. Tolerance can be described as the relative ability of a plant to survive infection without showing severe symptoms such as death, stunting, loss of vigor or yield loss. Tolerance includes any mechanism other than whole-plant immunity or resistance that reduces the expression of symptoms indicative of infection. Infected plants that exhibit tolerance will yield nearly as well as uninfected plants and also prevent the evolution of host-adapted pathogenic *Sclerotinia* races capable of reducing soybean yield in previously resistant plants.

The development of molecular genetic markers has facilitated mapping and selection of agriculturally important traits in soybean. Markers tightly linked to disease tolerance genes are an asset in the rapid identification of tolerant soybean lines on the basis of genotype by the use of marker assisted selection (MAS). Introgressing disease tolerance genes into a desired cultivar would also be facilitated by using suitable DNA markers.

Molecular Markers and Marker Assisted Selection

A genetic map is a graphical representation of a genome (or a portion of a genome such as a single chromosome) where the distances between landmarks on the chromosome are measured by the recombination frequencies between the landmarks. A genetic landmark can be any of a variety of known polymorphic markers, for example but not limited to, molecular markers such as SSR markers, RFLP markers, or SNP markers. Furthermore, SSR markers can be derived from genomic or expressed nucleic acids (e.g., ESTs). The nature of these physical landmarks and the methods used to detect them vary, but all of these markers are physically distinguishable from each other (as well as from the plurality of alleles of any one particular marker) on the basis of polynucleotide length and/or sequence.

Although specific DNA sequences which encode proteins are generally well-conserved across a species, other regions of DNA (typically non-coding) tend to accumulate polymorphism, and therefore, can be variable between individuals of the same species. Such regions provide the basis for numerous molecular genetic markers. In general, any differentially inherited polymorphic trait (including nucleic acid polymorphism) that segregates among progeny is a potential marker. The genomic variability can be of any origin, for example, insertions, deletions, duplications, repetitive elements, point mutations, recombination events, or the presence and sequence of transposable elements. A large number of soybean molecular markers are known in the art, and are published or available from various sources, such as the SOYBASE internet resource. Similarly, numerous methods for detecting molecular markers are also well-established.

The primary motivation for developing molecular marker technologies from the point of view of plant breeders has been the possibility to increase breeding efficiency through marker assisted selection (MAS). A molecular marker allele that demonstrates linkage disequilibrium with a desired phenotypic trait (e.g., a quantitative trait locus, or QTL, such as resistance to a particular disease) provides a useful tool for the selection of a desired trait in a plant population. The key components to the implementation of this approach are: (i) the creation of a dense genetic map of molecular markers, (ii) the detection of QTL based on statistical associations between marker and phenotypic variability, (iii) the definition of a set of desirable marker alleles based on the results of the QTL analysis, and (iv) the use and/or extrapolation of this information to the current set of breeding germplasm to enable marker-based selection decisions to be made.

The availability of integrated linkage maps of the soybean genome containing increasing densities of public soybean markers has facilitated soybean genetic mapping and MAS. See, e.g., Cregan et al. (1999) "An Integrated Genetic Linkage Map of the Soybean Genome" *Crop Sci.* 39: 1464-1490; Song et al., "A New Integrated Genetic Linkage Map of the Soybean," Theor. Appl. Genet., 109:122-128 (2004); Diwan and Cregan (1997) "Automated sizing of fluorescent-labeled simple sequence repeat (SSR) markers to assay genetic variation in Soybean," *Theor. Appl. Genet.,* 95:220-225; the Soybase resources on the world wide web at soybase.org, including the Shoemaker Lab Home Page and other resources that can be accessed through Soybase; and see the Soybean Genomics and Improvements Laboratory (SGIL) on the world wide web, and see especially the Cregan Lab web site.

Two types of markers are frequently used in marker assisted selection protocols, namely simple sequence repeat (SSR, also known as microsatellite) markers, and single nucleotide polymorphism (SNP) markers. The term SSR refers generally to any type of molecular heterogeneity that results in length variability, and most typically is a short (up to several hundred base pairs) segment of DNA that consists of multiple tandem repeats of a two or three base-pair sequence. These repeated sequences result in highly polymorphic DNA regions of variable length due to poor replication fidelity, e.g., caused by polymerase slippage. SSRs appear to be randomly dispersed through the genome and are generally flanked by conserved regions. SSR markers can also be derived from RNA sequences (in the form of a cDNA, a partial cDNA or an EST) as well as genomic material.

The characteristics of SSR heterogeneity make them well suited for use as molecular genetic markers; namely, SSR genomic variability is inherited, is multiallelic, codominant and is reproducibly detectable. The proliferation of increasingly sophisticated amplification-based detection techniques (e.g., PCR-based) provides a variety of sensitive methods for the detection of nucleotide sequence heterogeneity. Primers (or other types of probes) are designed to hybridize to conserved regions that flank the SSR domain, resulting in the amplification of the variable SSR region. The different sized amplicons generated from an SSR region have characteristic and reproducible sizes. The different sized SSR amplicons observed from two homologous chromosomes in an individual, or from different individuals in the plant population are generally termed "marker alleles." As long as there exists at least two SSR alleles that produce PCR products with at least two different sizes, the SSRs can be employed as a marker.

Soybean markers that rely on single nucleotide polymorphisms (SNPs) are also well known in the art. Various techniques have been developed for the detection of SNPs, including allele specific hybridization (ASH; see, e.g., Coryell et al., (1999) "Allele specific hybridization markers for soybean," *Theor. Appl. Genet.,* 98:690-696). Additional types of molecular markers are also widely used, including but not limited to expressed sequence tags (ESTs) and SSR markers derived from EST sequences, restriction fragment length polymorphism (RFLP), amplified fragment length polymorphism (AFLP), randomly amplified polymorphic DNA (RAPD) and isozyme markers. A wide range of protocols are known to one of skill in the art for detecting this variability, and these protocols are frequently specific for the type of polymorphism they are designed to detect. For example, PCR amplification, single-strand conformation polymorphisms (SSCP) and self-sustained sequence replication (3SR; see Chan and Fox, "NASBA and other transcription-based amplification methods for research and diagnostic microbiology," Reviews in Medical Microbiology 10:185-196 [1999]).

Linkage of one molecular marker to another molecular marker is measured as a recombination frequency. In general, the closer two loci (e.g., two SSR markers) are on the genetic map, the closer they lie to each other on the physical map. A relative genetic distance (determined by crossing over frequencies, measured in centimorgans; cM) is generally proportional to the physical distance (measured in base pairs, e.g., kilobase pairs [kb] or megabasepairs [Mbp]) that two linked loci are separated from each other on a chromosome. A lack of precise proportionality between cM and physical distance can result from variation in recombination frequencies for different chromosomal regions, e.g., some chromosomal regions are recombinational "hot spots," while others regions do not show any recombination, or only demonstrate rare recombination events. In general, the closer one marker is to another marker, whether measured in terms of recombination or physical distance, the more strongly they are linked. In some aspects, the closer a molecular marker is to a gene that encodes a polypeptide that imparts a particular phenotype (disease tolerance), whether measured in terms of recombination or physical distance, the better that marker serves to tag the desired phenotypic trait.

Genetic mapping variability can also be observed between different populations of the same crop species, including soybean. In spite of this variability in the genetic map that may occur between populations, genetic map and marker information derived from one population generally remains useful across multiple populations in identification of plants with desired traits, counter-selection of plants with undesirable traits and in guiding MAS.

QTL Mapping

It is the goal of the plant breeder to select plants and enrich the plant population for individuals that have desired traits, for example, pathogen tolerance, leading ultimately to increased agricultural productivity. It has been recognized for quite some time that specific chromosomal loci (or intervals) can be mapped in an organism's genome that correlate with particular quantitative phenotypes. Such loci are termed quantitative trait loci, or QTL. The plant breeder can advantageously use molecular markers to identify desired individuals by identifying marker alleles that show a statistically significant probability of co-segregation with a desired phenotype (e.g., pathogenic infection tolerance), manifested as linkage disequilibrium. By identifying a molecular marker or clusters of molecular markers that co-segregate with a quantitative trait, the breeder is thus identifying a QTL. By identifying and selecting a marker allele (or desired alleles from multiple markers) that associates with the desired phenotype, the plant breeder is able to rapidly select a desired phenotype by selecting for the proper molecular marker allele (a process called marker-assisted selection, or MAS). The more molecular markers that are placed on the genetic map, the more potentially useful that map becomes for conducting MAS.

Multiple experimental paradigms have been developed to identify and analyze QTL (see, e.g., Jansen (1996) Trends Plant Sci 1:89). The majority of published reports on QTL mapping in crop species have been based on the use of the bi-parental cross (Lynch and Walsh (1997) *Genetics and Analysis of Quantitative Traits*, Sinauer Associates, Sunderland). Typically, these paradigms involve crossing one or more parental pairs, which can be, for example, a single pair derived from two inbred strains, or multiple related or unrelated parents of different inbred strains or lines, which each exhibit different characteristics relative to the phenotypic trait of interest. Typically, this experimental protocol involves deriving 100 to 300 segregating progeny from a single cross of two divergent inbred lines (e.g., selected to maximize phenotypic and molecular marker differences between the lines). The parents and segregating progeny are genotyped for multiple marker loci and evaluated for one to several quantitative traits (e.g., disease resistance). QTL are then identified as significant statistical associations between genotypic values and phenotypic variability among the segregating progeny. The strength of this experimental protocol comes from the utilization of the inbred cross, because the resulting F1 parents all have the same linkage phase. Thus, after selfing of the F1 plants, all segregating progeny (F2) are informative and linkage disequilibrium is maximized, the linkage phase is known, there are only two QTL alleles, and, except for back-cross progeny, the frequency of each QTL allele is 0.5.

Numerous statistical methods for determining whether markers are genetically linked to a QTL (or to another marker) are known to those of skill in the art and include, e.g., standard linear models, such as ANOVA or regression mapping (Haley and Knott (1992) Heredity 69:315), maximum likelihood methods such as expectation-maximization algorithms, (e.g., Lander and Botstein (1989) "Mapping Mendelian factors underlying quantitative traits using RFLP linkage maps," Genetics 121:185-199; Jansen (1992) "A general mixture model for mapping quantitative trait loci by using molecular markers," Theor. Appl. Genet., 85:252-260; Jansen (1993) "Maximum likelihood in a generalized linear finite mixture model by using the EM algorithm," Biometrics 49:227-231; Jansen (1994) "Mapping of quantitative trait loci by using genetic markers: an overview of biometrical models," In J. W. van Ooijen and J. Jansen (eds.), *Biometrics in Plant breeding: applications of molecular markers*, pp. 116-124, CPRO-DLO Metherlands; Jansen (1996) "A general Monte Carlo method for mapping multiple quantitative trait loci," Genetics 142:305-311; and Jansen and Stam (1994) "High Resolution of quantitative trait into multiple loci via interval mapping," Genetics 136:1447-1455). Exemplary statistical methods include single point marker analysis, interval mapping (Lander and Botstein (1989) Genetics 121:185), composite interval mapping, penalized regression analysis, complex pedigree analysis, MCMC analysis, MQM analysis (Jansen (1994) Genetics 138:871), HAPLO-IM+ analysis, HAPLO-MQM analysis, and HAPLO-MQM+ analysis, Bayesian MCMC, ridge regression, identity-by-descent analysis, Haseman-Elston regression, any of which are suitable in the context of the present invention. In addition, additional details regarding alternative statistical methods applicable to complex breeding populations which can be used to identify and localize QTLs are described in: U.S. Ser. No. 09/216,089 by Beavis et al. "QTL MAPPING IN PLANT BREEDING POPULATIONS" and PCT/US00/34971 by Jansen et al. "MQM MAPPING USING HAPLOTYPED PUTATIVE QTLS ALLELES: A SIMPLE APPROACH FOR MAPPING QTLS IN PLANT BREEDING POPULATIONS." Any of these approaches are computationally intensive and are usually performed with the assistance of a computer based system and specialized software. Appropriate statistical packages are available from a variety of public and commercial sources, and are known to those of skill in the art.

There is a need in the art for improved soybean strains that are tolerant to *Sclerotinia* white mold infections, such as *Sclerotinia sclerotiorum* (Lib.) de Bary infections. There is a need in the art for methods that identify soybean plants or populations (germplasm) that display tolerance to *Sclerotinia* infection. What is needed in the art is to identify molecular genetic markers that are linked to *Sclerotinia* tolerance loci (e.g., tolerance QTL) in order to facilitate MAS, and also to facilitate gene discovery and cloning of gene alleles that impart *Sclerotinia* infection tolerance. Such markers can be used to select individual plants and plant populations that show favorable marker alleles in soybean populations and then employed to select the tolerant phenotype, or alternatively, be used to counterselect plants or plant populations that show a *Sclerotinia* infection susceptibility phenotype. The present invention provides these and other advantages.

SUMMARY OF THE INVENTION

Compositions and methods for identifying soybean plants or germplasm with tolerance to *Sclerotinia* infection are provided. Methods of making soybean plants or germplasm that are tolerant to *Sclerotinia* infection, e.g., through introgression of desired tolerance marker alleles and/or by transgenic production methods, as well as plants and germplasm made by these methods, are also provided. Systems and kits for selecting tolerant plants and germplasm are also a feature of the invention.

*Sclerotinia* infection is a major disease of soybean, causing severe losses in soybean viability and overall yield. *Sclerotinia* resistant soybean cultivars have been produced in an attempt to reduce these losses. However, the strong selective pressures that resistant soybean impose on *Sclerotinia* cause relatively rapid loss of the resistance phenotype. In contrast, tolerance to *Sclerotinia* infection, in which the plant survives and produces high yields, despite a productive *Sclerotinia* infection, is an alternate strategy to combat losses due to *Sclerotinia* infection. Pathogen tolerance provides advantages over pathogen resistance. Selection for pathogen tolerance in the plant is less likely to result in the evolution of destructive races of *Sclerotinia* that combat and overcome the tolerance traits, leading to a host/pathogen relationship that more resembles commensalism as opposed to parasitism.

The identification and selection of soybean plants that show tolerance to *Sclerotinia* infection using MAS can provide an effective and environmentally friendly approach to overcoming losses caused by this disease. The present invention provides a number of soybean marker loci and QTL chromosome intervals that demonstrate statistically significant co-segregation with *Sclerotinia* tolerance. Detection of these QTL markers or additional loci linked to the QTL markers can be used in marker-assisted soybean breeding programs to produce tolerant plants, or plants with improved tolerance.

In some aspects, the invention provides methods for identifying a first soybean plant or germplasm (e.g., a line or variety) that has tolerance, improved tolerance, reduced susceptibility or susceptibility to *Sclerotinia* infection. In the methods, at least one allele of one or more marker locus (e.g., a plurality of marker loci) that is associated with the tolerance, improved tolerance, reduced susceptibility or susceptibility are detected in the first soybean plant or germplasm. The marker loci can be selected from loci provided in FIG. 1, including: SAG1032, SATT597, SCT_026, SATT391, S60817-TB, S60239-TB, P10646A-1, P7659A-2, SATT570, SATT356, S60222-TB, SATT166, SATT448 and SAG1048, as well as any other marker that is closely linked to these QTL markers (e.g., markers within about 10 cM of these loci). The invention also provides chromosomal QTL intervals that correlate with *Sclerotinia* infection tolerance. These intervals are located on linkage groups B1, G, L and M. Any marker located within (and including the termini of) these intervals also finds use as a marker for *Sclerotinia* infection tolerance and are also a feature of the invention. These intervals include:

(i) SAG1032 and SCT_026 (LG-B1);
(ii) S60239-TB and SATT356 (LG-G);
(iii) SATT166 and SATT448 (LG-L); and
(iv) SATT463 and SATT175 (LG-M).

A plurality of maker loci can be selected in the same plant. Which QTL markers are selected in combination is not particularly limited. The QTL markers used in combinations can be any of the makers listed in FIG. 1, any other marker that is closely linked to the markers in FIG. 1 (e.g., the closely linked markers as determined from FIG. 6 or FIG. 7, or determined from the SOYBASE resource), or any marker within the QTL intervals described herein.

The markers that are linked to the QTL markers of FIG. 1 can be closely linked, for example, within about 10 cM from the FIG. 1 QTL markers. In some embodiments, the linked locus displays a genetic recombination distance of 9 centiMorgans, 8, 7, 6, 5, 4, 3, 2, 1, 0.75, 0.5 or 0.25, or less from the QTL marker. In some embodiments, the closely linked locus is selected from the list of marker loci from FIG. 6 or FIG. 7.

In some embodiments, preferred QTL markers are selected from SAG1032, SATT391, S60817-TB., S60239-TB, S60222-TB, SATT166, SATT448 and SAG1048.

In some embodiments, the germplasm is a soybean line or variety. In some aspects, the tolerance or improved tolerance is a non-race specific tolerance or a non-race specific improved tolerance. In some aspects, the tolerance, improved tolerance, reduced susceptibility or susceptibility of a soybean plant to *Sclerotinia* infection can be quantitated using any suitable means, for example, by assaying soybean infection in a field where *Sclerotinia* infection occurs naturally, by a stem lesion assay or a detached leaf assay. In some aspects, the *Sclerotinia* sp. is *Sclerotinia sclerotiorum* (Lib.) de Bary.

Any of a variety of techniques can be used to identify a marker allele. It is not intended that the method of allele detection be limited in any way. Methods for allele detection typically include molecular identification methods such as amplification and detection of the marker amplicon. For example, an allelic form of a polymorphic simple sequence repeat (SSR), or of a single nucleotide polymorphism (SNP) can be detected, e.g., by an amplification based technology. In these and other amplification based detection methods, the marker locus or a portion of the marker locus is amplified (e.g., via PCR, LCR or transcription using a nucleic acid isolated from a soybean plant of interest as a template) and the resulting amplified marker amplicon is detected. In one example of such an approach, an amplification primer or amplification primer pair is admixed with genomic nucleic acid isolated from the first soybean plant or germplasm, wherein the primer or primer pair is complementary or partially complementary to at least a portion of the marker locus, and is capable of initiating DNA polymerization by a DNA polymerase using the soybean genomic nucleic acid as a template. The primer or primer pair (e.g., a primer pair provided in FIG. 2) is extended in a DNA polymerization reaction having a DNA polymerase and a template genomic nucleic acid to generate at least one amplicon. In any case, data representing the detected allele(s) can be transmitted (e.g., electronically or via infrared, wireless or optical transmission) to a computer or computer readable medium for analysis or storage. In some embodiments, plant RNA is the template for the amplification reaction. In other embodiments, plant genomic DNA is the template for the amplification reaction. In some embodiments, the QTL marker is a SNP type marker, and the detected allele is a SNP allele (see, e.g., FIG. 3), and the method of detection is allele specific hybridization (ASH).

In some embodiments, the allele that is detected is a favorable allele that positively correlates with tolerance or improved tolerance. Alternatively, the allele that is detected can be an allele that correlates with disease susceptibility, and that allele is counter-selected. For example, alleles that can be selected for (favorable alleles) or against (unfavorable alleles) include SAG1048:allele-2, SAG1048:allele-3, S60817-TB:allele-2, S60817-TB:allele-3 or S60817-TB:allele-4.

In some embodiments, the allele that is detected is a favorable allele that positively correlates with tolerance or improved tolerance, e.g., SAG1048:allele-3 and S60817-TB:allele-2. In the case where more than one marker is selected, an allele is selected for each of the markers; thus, two or more alleles are selected. In some embodiments, it can be the case that a marker locus will have more than one advantageous allele, and in that case, either allele can be selected.

It will be appreciated that the ability to identify QTL marker loci that correlate with tolerance, improved tolerance, reduced susceptibility or susceptibility of a soybean plant to *Sclerotinia* infection provides a method for selecting plants that have favorable marker loci as well. That is, any plant that is identified as comprising a desired marker locus (e.g., a marker allele that positively correlates with tolerance) can be selected for, while plants that lack the locus, or that have a locus that negatively correlates with tolerance, can be selected against. Thus, in one method, subsequent to identification of a marker locus, the methods include selecting (e.g., isolating) the first soybean plant or germplasm, or selecting a progeny of the first plant or germplasm. In some embodiments, the resulting selected first soybean plant or germplasm can be crossed with a second soybean plant or germplasm (e.g., an elite or exotic soybean, depending on characteristics that are desired in the progeny).

Similarly, in other embodiments, if an allele is correlated with tolerance or improved tolerance to *Sclerotinia* infection, the method can include introgressing the allele into a second soybean plant or germplasm to produce an introgressed soybean plant or germplasm. In some embodiments, the second soybean plant or germplasm will typically display reduced tolerance to *Sclerotinia* infection as compared to the first soybean plant or germplasm, while the introgressed soybean plant or germplasm will display an increased tolerance to *Sclerotinia* infection as compared to the second plant or germplasm. An introgressed soybean plant or germplasm produced by these methods are also a feature of the invention. In some embodiments, the favorable introgressed allele is SAG1048:allele-3 or S60817-TB:allele-2.

In some embodiments, where an introgressed soybean plant or germplasm is produced by any of the methods provided herein, the introgressed soybean plant or germplasm can be characterized by a *Sclerotinia* stem rot tolerance score greater than 6 as measured in a field location previously known to produce soybean plants that demonstrate *Sclerotinia* stem rot. In some embodiments, the introgressed soybean plant or germplasm is characterized by a *Sclerotinia* stem rot tolerance score greater than 6 as measured by use of a stem lesion assay or a detached leaf assay.

In other aspects, various mapping populations are used to determine the linked markers of the invention. In one embodiment, the mapping population used is the population derived from the cross 9163/92B05. In other embodiments, other populations can be used. In other aspects, various software can be used in determining linked marker loci. For example, TASSEL, GeneFlow and MapManager-QTX all find use with the invention. In some embodiments, such as when software is used in the linkage analysis, the detected allele information (i.e., the data) is electronically transmitted or electronically stored, for example, in a computer readable medium.

In some embodiments, a first soybean plant or germplasm that displays tolerance, improved tolerance or susceptibility to *Sclerotinia* stem rot is identified by using novel combinations (i.e., a plurality) of marker alleles. For example, the invention provides methods for identifying plants or germplasm displaying tolerance, improved tolerance, reduced susceptibility or susceptibility to *Sclerotinia* stem rot, where at least one allele of the marker locus SATT243 or a locus closely linked thereto is identified, and in addition, at least one allele of the marker loci SAG1032, SATT597, SCT_026, SATT391, S60817-TB, S60239-TB, P10646A-1, P7659A-2, SATT570, SATT356, S60222-TB, SATT166, SATT448 and SAG1048 or a locus closely linked thereto, or a locus from an interval selected from:

(i) SAG1032 and SCT_026 (LG-B1);
 (ii) S60239-TB and SATT356 (LG-G);
 (iii) SATT166 and SATT448 (LG-L); and
 (iv) SATT463 and SATT175 (LG-M), are also identified. In some embodiments, the identified alleles correlate with tolerance or improved tolerance to *Sclerotinia* stem rot, and each identified marker allele is introgressed from the first soybean plant or germplasm into a second soybean plant or germplasm to produce an introgressed soybean plant or germplasm. In some aspects, the identified alleles include SAG1048:allele-3 or S60817-TB:allele-2:allele-4. The introgressed plant produced by the above method is also a feature of the invention, where the resulting introgressed soybean plant has the following characteristics: (a) the second soybean plant or germplasm displays less tolerance to *Sclerotinia* stem rot as compared to the first soybean plant or germplasm prior to introgressing; (b) the introgressed soybean plant or germplasm displays a greater tolerance to *Sclerotinia* stem rot as compared to the second plant or germplasm; and, (c) the introgressed soybean plant or germplasm shows a *Sclerotinia* stem rot tolerance score greater than 6 as measured in a field location previously known to produce soybean plants that demonstrate *Sclerotinia* stem rot.

In addition to introgressing selected marker alleles into desired genetic backgrounds, transgenic approaches can also be used to produce *Sclerotinia* tolerant soybean plants or germplasm. For example, in some aspects, the invention provides methods of producing a soybean plant having tolerance or improved tolerance to *Sclerotinia* infection, the methods comprising introducing an exogenous nucleic acid into a target soybean plant or progeny thereof, wherein the exogenous nucleic acid is derived from a nucleotide sequence that is linked to at least one favorable allele of one or more marker locus that is associated with tolerance or improved tolerance to *Sclerotinia* infection. In some embodiments, the marker locus can be selected from: SAG1032, SATT597, SCT_026, SATT391, S60817-TB, S60239-TB, P10646A-1, P7659A-2, SATT570, SATT356, S60222-TB, SATT166, SATT448 and SAG1048, as well as any other marker that is closely linked (e.g., demonstrating not more than 10% recombination frequency) to these QTL markers; and furthermore, any marker locus that is located within the chromosomal QTL intervals including:

(i) SAG1032 and SCT_026 (LG-B1);
 (ii) S60239-TB and SATT356 (LG-G);
 (iii) SATT166 and SATT448 (LG-L); and
 (iv) SATT463 and SATT175 (LG-M).

In some embodiments, preferred QTL markers used in these transgenic plant methods are selected from SAG1032, SATT391, S60817-TB., S60239-TB, S60222-TB, SATT166, SATT448 and SAG1048.

In some embodiments, a plurality of maker loci can be used to construct the transgenic plant. Which QTL markers are used in combination is not particularly limited. The QTL markers used in combinations can be makers listed in FIG. 1, any other marker that is linked to the markers in FIG. 1 (e.g., the linked markers as determined from FIGS. 6 and 7, or determined from the SOYBASE resource), or any markers selected from the QTL intervals described herein.

In some embodiments, the tolerance or improved tolerance is a non-race specific tolerance or a non-race specific improved tolerance. In some aspects, the *Sclerotinia* sp. is *Sclerotinia sclerotiorum* (Lib.) de Bary.

Any of a variety of methods can be used to provide the exogenous nucleic acid to the soybean plant. In one method, the nucleotide sequence is isolated by positional cloning, and is identified by linkage to the favorable allele. The precise composition of the exogenous nucleic acid can vary; in one embodiment, the exogenous nucleic acid corresponds to an open reading frame (ORF) that encodes a polypeptide that, when expressed in a soybean plant, results in the soybean plant having tolerance or improved tolerance to *Sclerotinia* infection. The exogenous nucleic acid optionally comprises an expression vector to provide for expression of the exogenous nucleic acid in the plant.

In other aspects, various mapping populations are used to determine the linked markers that find use in constructing the transgenic plant. In one embodiment, the mapping population used is the population derived from the cross 9163/92B05. In other embodiments, other populations can be used. In other aspects, various software and software parameters are used in determining linked marker loci used to construct the transgenic plant. For example, TASSEL, GeneFlow and MapManager-QTX all find use with the invention.

In some aspects, the invention provides methods for producing a soybean plant having tolerance or improved tolerance to *Sclerotinia* stem rot, where the methods include the construction of transgenic plants that carry more than one transgene. In the methods for producing plants having tolerance or improved tolerance to *Sclerotinia* stem rot, the methods include introducing two or more exogenous nucleic acids into a target soybean plant or progeny thereof, where the exogenous nucleic acids are derived from genomic nucleotide sequences that are closely linked to at least one favorable allele from each of two or more marker loci that are associated with tolerance or improved tolerance to *Sclerotinia* stem rot, wherein at least one of the two or more marker loci is SATT243 or a locus closely linked thereto, and at least one locus of the two or more marker loci is selected from SAG1032, SATT597, SCT_026, SATT391, S60817-TB, S60239-TB, P10646A-1, P7659A-2, SATT570, SATT356, S60222-TB, SATT166, SATT448 and SAG1048 or a locus closely linked thereto, or a locus from an interval selected from:

(i) SAG1032 and SCT_026 (LG-B1);
(ii) S60239-TB and SATT356 (LG-G);
(iii) SATT166 and SATT448 (LG-L); and
(iv) SATT463 and SATT175 (LG-M), whereby the resulting transgenic plant displays tolerance or improved tolerance to *Sclerotinia* stem rot.

Systems for identifying a soybean plant predicted to have tolerance or improved tolerance to *Sclerotinia* infection are also a feature of the invention. Typically, the systems include: (A) a set of marker primers and/or probes configured to detect at least one favorable allele of one or more marker locus associated with tolerance or improved tolerance to *Sclerotinia* infection, wherein the marker locus or loci are selected from: SAG1032, SATT597, SCT_026, SATT391, S60817-TB, S60239-TB, P10646A-1, P7659A-2, SATT570, SATT356, S60222-TB, SATT166, SATT448 and SAG1048, as well as any other marker that is closely linked (e.g., demonstrating not more than 10% recombination frequency) to these QTL markers; and furthermore, any marker locus that is located within the chromosomal QTL intervals including:

(i) SAG1032 and SCT_026 (LG-B1);
(ii) S60239-TB and SATT356 (LG-G);
(iii) SATT166 and SATT448 (LG-L); and
(iv) SATT463 and SATT175 (LG-M);

(B) a detector that is configured to detect one or more signal outputs from the set of marker probes or primers, or amplicon thereof, thereby identifying the presence or absence of the allele; and (C) system instructions that correlate the presence or absence of the favorable allele with the predicted tolerance or susceptibility. In some system embodiments, preferred QTL markers used are selected from SAG1032, SATT391, S60817-TB., S60239-TB, S60222-TB, SATT166, SATT448 and SAG1048.

Where a system that performs marker detection or correlation is desired, the system can also include a detector that is configured to detect one or more signal outputs from the set of marker probes or primers, or amplicon thereof, thereby identifying the presence or absence of the allele; and/or system instructions that correlate the presence or absence of the favorable allele with the predicted tolerance. The precise configuration of the detector will depend on the type of label used to detect the marker allele. Typical embodiments include light detectors, radioactivity detectors, and the like. Detection of the light emission or other probe label is indicative of the presence or absence of a marker allele. Similarly, the precise form of the instructions can vary depending on the components of the system, e.g., they can be present as system software in one or more integrated unit of the system, or can be present in one or more computers or computer readable media operably coupled to the detector. In one typical embodiment, the system instructions include at least one look-up table that includes a correlation between the presence or absence of the favorable allele and predicted tolerance, improved tolerance or susceptibility.

In some embodiments, the system can be comprised of separate elements or can be integrated into a single unit for convenient detection of markers alleles and for performing marker-tolerance trait correlations. In some embodiments, the system can also include a sample, for example, genomic DNA, amplified genomic DNA, cDNA, amplified cDNA, RNA, or amplified RNA from soybean or from a selected soybean plant tissue.

Kits are also a feature of the invention. For example, a kit can include appropriate primers or probes for detecting tolerance associated marker loci and instructions in using the primers or probes for detecting the marker loci and correlating the loci with predicted *Sclerotinia* tolerance. The kits can further include packaging materials for packaging the probes, primers or instructions, controls such as control amplification reactions that include probes, primers or template nucleic acids for amplifications, molecular size markers, or the like.

In other aspects, the invention provides nucleic acid compositions that are the novel EST-derived SSR QTL markers of the invention. For example, the invention provides compositions comprising an amplification primer pair capable of initiating DNA polymerization by a DNA polymerase on a soybean nucleic acid template to generate a soybean marker amplicon, where the marker amplicon corresponds to a soybean marker selected from SAG1032, S60817-TB, S60239-TB or S60222-TB. For example, the primer pair that is specific for the marker can be selected from SEQ ID NOs:1 and 2, SEQ ID NOs:9 and 10, SEQ ID NOs:11 and 12 and SEQ ID NOs:19 and 20.

DEFINITIONS

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a," "an" and "the," for example, include plural referents unless the content clearly dictates otherwise. Thus, for example, reference to "plant," "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant. Thus, the term "soybean plant" includes whole soybean plants, soybean plant cells, soybean plant protoplast, soybean plant cell or soybean tissue culture from which soybean plants can be regenerated, soybean plant calli, soybean plant clumps and soybean plant cells that are intact in soybean plants or parts of soybean plants, such as soybean seeds, soybean pods, soybean flowers, soybean cotyledons, soybean leaves, soybean stems, soybean buds, soybean roots, soybean root tips and the like.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, that can be cultured into a whole plant.

The term "allele" refers to one of two or more different nucleotide sequences that occur at a specific locus. For example, a first allele can occur on one chromosome, while a second allele occurs on a second homologous chromosome, e.g., as occurs for different chromosomes of a heterozygous individual, or between different homozygous or heterozygous individuals in a population. A "favorable allele" is the allele at a particular locus that confers, or contributes to, an agronomically desirable phenotype, e.g., tolerance to *Sclerotinia* infection, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease-prone plants. A favorable allelic form of a chromosome segment is a chromosome segment that includes a nucleotide sequence that contributes to superior agronomic performance at one or more genetic loci physically located on the chromosome segment. "Allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An allele "positively" correlates with a trait when it is linked to it and when presence of the allele is an indictor that the desired trait or trait form will occur in a plant comprising the allele. An allele negatively correlates with a trait when it is linked to it and when presence of the allele is an indicator that a desired trait or trait form will not occur in a plant comprising the allele.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

A "locus" is a chromosomal region where a polymorphic nucleic acid, trait determinant, gene or marker is located. Thus, for example, a "gene locus" is a specific chromosome location in the genome of a species where a specific gene can be found.

The term "quantitative trait locus" or "QTL" refers to a polymorphic genetic locus with at least two alleles that differentially affect the expression of a phenotypic trait in at least one genetic background, e.g., in at least one breeding population or progeny.

The terms "marker," "molecular marker," "marker nucleic acid," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus. In some aspects, the present invention provides marker loci correlating with tolerance to *Sclerotinia* infection in soybean. Each of the identified markers is expected to be in close physical and genetic proximity (resulting in physical and/or genetic linkage) to a genetic element, e.g., a QTL, that contributes to tolerance.

"Genetic markers" are nucleic acids that are polymorphic in a population and where the alleles of which can be detected and distinguished by one or more analytic methods, e.g., RFLP, AFLP, isozyme, SNP, SSR, and the like. The terms "genetic marker" and "molecular marker" refer to a genetic locus (a "marker locus") that can be used as a point of reference when identifying a genetically linked locus such as a QTL. Such a marker is also referred to as a QTL marker. The term also refers to nucleic acid sequences complementary to the genomic sequences, such as nucleic acids used as probes.

Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A "genetic map" is a description of genetic linkage relationships among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a physical map of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map.

A "genetic recombination frequency" is the frequency of a crossing over event (recombination) between two genetic loci. Recombination frequency can be observed by following the segregation of markers and/or traits following meiosis. A genetic recombination frequency can be expressed in centimorgans (cM), where one cM is the distance between two genetic markers that show a 1% recombination frequency (i.e., a crossing-over event occurs between those two markers once in every 100 cell divisions).

As used herein, the term "linkage" is used to describe the degree with which one marker locus is "associated with" another marker locus or some other locus (for example, a tolerance locus).

As used herein, linkage equilibrium describes a situation where two markers independently segregate, i.e., sort among progeny randomly. Markers that show linkage equilibrium are considered unlinked (whether or not they lie on the same chromosome).

As used herein, linkage disequilibrium describes a situation where two markers segregate in a non-random manner, i.e., have a recombination frequency of less than 50% (and by definition, are separated by less than 50 cM on the same linkage group). Markers that show linkage disequilibrium are considered linked. Linkage occurs when the marker locus and a linked locus are found together in progeny plants more frequently than not together in the progeny plants. As used herein, linkage can be between two markers, or alternatively between a marker and a phenotype. A marker locus can be associated with (linked to) a trait, e.g., a marker locus can be associated with tolerance or improved tolerance to a plant pathogen when the marker locus is in linkage disequilibrium with the tolerance trait. The degree of linkage of a molecular marker to a phenotypic trait (e.g., a QTL) is measured, e.g., as a statistical probability of co-segregation of that molecular marker with the phenotype.

As used herein, the linkage relationship between a molecular marker and a phenotype is given as a "probability" or "adjusted probability." The probability value is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant." In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p=0.5). For example, a significant probability can be less than 0.25, less than 0.20, less than 0.15, or less than 0.1.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. The term "physically linked" is sometimes used to indicate that two loci, e.g., two marker loci, are physically present on the same chromosome.

Advantageously, the two linked loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

The phrase "closely linked," in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait (e.g., pathogenic tolerance). For example, in some aspects, these markers can be termed linked QTL markers. In other aspects, especially useful molecular markers are those markers that are linked or closely linked to QTL markers.

In some aspects, linkage can be expressed as any desired limit or range. For example, in some embodiments, two linked loci are two loci that are separated by less than 50 cM map units. In other embodiments, linked loci are two loci that are separated by less than 40 cM. In other embodiments, two linked loci are two loci that are separated by less than 30 cM. In other embodiments, two linked loci are two loci that are separated by less than 25 cM. In other embodiments, two linked loci are two loci that are separated by less than 20 cM. In other embodiments, two linked loci are two loci that are separated by less than 15 cM. In some aspects, it is advantageous to define a bracketed range of linkage, for example, between 10 and 20 cM, or between 10 and 30 cM, or between 10 and 40 cM.

The more closely a marker is linked to a second locus, the better an indicator for the second locus that marker becomes. Thus, in one embodiment, closely linked loci such as a marker locus and a second locus (e.g., a QTL marker) display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a QTL marker) display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (i.e., the two loci are "out of phase" with each other).

As used herein, the terms "chromosome interval" or "chromosome segment" designate a contiguous linear span of genomic DNA that resides in planta on a single chromosome. The genetic elements or genes located on a single chromosome interval are physically linked. The size of a chromosome interval is not particularly limited.

In some aspects, for example in the context of the present invention, generally the genetic elements located within a single chromosome interval are also genetically linked, typically within a genetic recombination distance of, for example, less than or equal to 20 centimorgan (cM), or alternatively, less than or equal to 10 cM. That is, two genetic elements within a single chromosome interval undergo recombination at a frequency of less than or equal to 20% or 10%

In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The phrase "*Sclerotinia* stem rot" refers to the plant disease caused by an infection of the fungal pathogen *Sclerotinia sclerotiorum* (Lib.) de Bary. *Sclerotinia* stem rot is alternatively referred to as white mold, *Sclerotinia* white mold or soybean white mold (when infecting soybean species). The disease caused by an infection with *Sclerotinia sclerotiorum* can display a variety pathology and a range of severity.

"Tolerance" or "improved tolerance" in a soybean plant to *Sclerotinia* infection is an indication that the soybean plant is less affected with respect to yield and/or survivability or other relevant agronomic measures, upon infection by *Sclerotinia*, than a less tolerant or more "susceptible" plant. Tolerance is a relative term, indicating that the infected plant produces better yield of soybean than another similarly infected more susceptible plant. That is, the infection causes a reduced decrease in soybean survival and/or yield in a tolerant soybean plant, as compared to a susceptible soybean plant. "Reduced susceptibility" refers to a relative reduction in a plant's susceptibility to *Sclerotinia* infection. A reduced susceptibility is a type of improvement in plant resistance, and in some embodiments, can be a desired result. One of skill will appreciate that soybean plant tolerance (or susceptibility) to *Sclerotinia* infection represents a broad phenotypic spectrum, and that tolerance also will vary depending on the severity of the infection.

One of skill will appreciate that soybean plant tolerance to *Sclerotinia* stem rot varies widely, and can represent a spectrum of more-tolerant or less-tolerant phenotypes. However, by simple observation, one of skill can generally determine the relative tolerance or susceptibility of different plants, plant lines or plant families when exposed to *Sclerotinia sclerotiorum* infection, and furthermore, will also recognize the phenotypic gradations of "tolerant."

One of skill in the art is familiar with assays for quantitating and scoring soybean plant tolerance (and resistance) to *Sclerotinia sclerotiorum* infection. See, e.g., EXAMPLES 4 and 5. In EXAMPLE 4, a plant's tolerance can be quantitated using a *Sclerotinia* stem rot scoring system. In such a system, a plant that is grown in an area known to produce *Sclerotinia sclerotiorum* infection, or in controlled greenhouse conditions using an *Sclerotinia sclerotiorum* innoculum, is assigned a tolerance rating between 1 (complete stem girdling with large lesion or lesions) to 9 (highly tolerant; no detectable *Sclerotinia sclerotiorum* infection; no browning; yield and survivability not significantly affected by *Sclerotinia sclerotiorum* infection). Soybean tolerance can also be assayed using a detached leaf method, as known in the art and described in EXAMPLE 5.

*Sclerotinia* "tolerance" differs from *Sclerotinia* "resistance" in that tolerance is a measure of a soybean plant's ability to survive and yield soybean despite the presence of *Sclerotinia* infection, as opposed to a measure of the soybean plant's ability to resist infection. As used in the art, "tolerance" is sometimes referred to as "general resistance," "rate-reducing resistance" or "partial resistance."

Resistance to *Sclerotinia* is often "race-specific." That is, over time, a population (e.g., a race) of *Sclerotinia* evolves to overcome a resistance trait in a given line of soybean. Once this occurs, the resistance trait is "race specific" in that the resistance trait is no longer effective at resisting infection by the evolved *Sclerotinia* population (that is, the evolved *Sclerotinia* population is a "race" that is not blocked from achieving a productive infection by the resistance trait). Tolerance, on the other hand, can sometimes be "non-race specific" in that populations of *Sclerotinia* are not necessarily selected to overcome tolerance, because a tolerant soybean plant permits the *Sclerotinia* pathogen to achieve a productive infection.

The term "crossed" or "cross" in the context of this invention means the fusion of gametes via pollination to produce progeny (e.g., cells, seeds or plants). The term encompasses both sexual crosses (the pollination of one plant by another) and selfing (self-pollination, e.g., when the pollen and ovule are from the same plant).

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor. Traditionally, a "subline" has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. In the context of the invention, marker-based sublines, that differ from each other based on qualitative polymorphism at the DNA level at one or more specific marker loci, are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (yield, tolerance, etc.).

An "ancestral line" is a parent line used as a source of genes e.g., for the development of elite lines. An "ancestral population" is a group of ancestors that have contributed the bulk of the genetic variation that was used to develop elite lines. "Descendants" are the progeny of ancestors, and may be separated from their ancestors by many generations of breeding. For example, elite lines are the descendants of their ancestors. A "pedigree structure" defines the relationship between a descendant and each ancestor that gave rise to that descendant. A pedigree structure can span one or more generations, describing relationships between the descendant and it's parents, grand parents, great-grand parents, etc.

An "elite line" or "elite strain" is an agronomically superior line that has resulted from many cycles of breeding and selection for superior agronomic performance. Numerous elite lines are available and known to those of skill in the art of soybean breeding. An "elite population" is an assortment of elite individuals or lines that can be used to represent the state of the art in terms of agronomically superior genotypes of a given crop species, such as soybean. Similarly, an "elite germplasm" or elite strain of germplasm is an agronomically superior germplasm, typically derived from and/or capable of giving rise to a plant with superior agronomic performance, such as an existing or newly developed elite line of soybean.

In contrast, an "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST.

An "exogenous nucleic acid" is a nucleic acid that is not native to a specified system (e.g., a germplasm, plant, variety, etc.), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts.

In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

The term "recombinant" in reference to a nucleic acid or polypeptide indicates that the material (e.g., a recombinant nucleic acid, gene, polynucleotide, polypeptide, etc.) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates. A gene sequence open reading frame is recombinant if that nucleotide sequence has been removed from it natural context and cloned into any type of artificial nucleic acid vector. Protocols and reagents to produce recombinant molecules, especially recombinant nucleic acids, are common and routine in the art. The term recombinant can also refer to an organism that harbors recombinant material, e.g., a plant that comprises a recombinant nucleic acid is considered a recombinant plant. In some embodiments, a recombinant organism is a transgenic organism.

The term "introduced" when referring to translocating a heterologous or exogenous nucleic acid into a cell refers to the incorporation of the nucleic acid into the cell using any methodology. The term encompasses such nucleic acid introduction methods as "transfection," "transformation" and "transduction."

As used herein, the term "vector" is used in reference to polynucleotide or other molecules that transfer nucleic acid segment(s) into a cell. The term "vehicle" is sometimes used interchangeably with "vector." A vector optionally comprises parts which mediate vector maintenance and enable its intended use (e.g., sequences necessary for replication, genes imparting drug or antibiotic resistance, a multiple cloning site, operably linked promoter/enhancer elements which enable the expression of a cloned gene, etc.). Vectors are often derived from plasmids, bacteriophages, or plant or animal viruses. A "cloning vector" or "shuttle vector" or "subcloning vector" contains operably linked parts that facilitate subcloning steps (e.g., a multiple cloning site containing multiple restriction endonuclease sites).

The term "expression vector" as used herein refers to a vector comprising operably linked polynucleotide sequences that facilitate expression of a coding sequence in a particular host organism (e.g., a bacterial expression vector or a plant expression vector). Polynucleotide sequences that facilitate expression in prokaryotes typically include, e.g., a promoter, an operator (optional), and a ribosome binding site, often along with other sequences. Eukaryotic cells can use promoters, enhancers, termination and polyadenylation signals and other sequences that are generally different from those used by prokaryotes.

The term "transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extrachromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"Positional cloning" is a cloning procedure in which a target nucleic acid is identified and isolated by its genomic proximity to marker nucleic acid. For example, a genomic nucleic acid clone can include part or all of two more chromosomal regions that are proximal to one another. If a marker can be used to identify the genomic nucleic acid clone from a genomic library, standard methods such as sub-cloning or sequencing can be used to identify and or isolate subsequences of the clone that are located near the marker.

A specified nucleic acid is "derived from" a given nucleic acid when it is constructed using the given nucleic acid's sequence, or when the specified nucleic acid is constructed using the given nucleic acid. For example, a cDNA or EST is derived from an expressed mRNA.

The term "genetic element" or "gene" refers to a heritable sequence of DNA, i.e., a genomic sequence, with functional significance. The term "gene" can also be used to refer to, e.g., a cDNA and/or a mRNA encoded by a genomic sequence, as well as to that genomic sequence.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome segment.

The terms "phenotype," or "phenotypic trait" or "trait" refers to one or more trait of an organism. The phenotype can be observable to the naked eye, or by any other means of evaluation known in the art, e.g., microscopy, biochemical analysis, genomic analysis, an assay for a particular disease resistance, etc. In some cases, a phenotype is directly controlled by a single gene or genetic locus, i.e., a "single gene trait." In other cases, a phenotype is the result of several genes. A "quantitative trait loci" (QTL) is a genetic domain that is polymorphic and effects a phenotype that can be described in quantitative terms, e.g., height, weight, oil content, days to germination, disease resistance, etc, and, therefore, can be assigned a "phenotypic value" which corresponds to a quantitative value for the phenotypic trait. A QTL can act through a single gene mechanism or by a polygenic mechanism.

A "molecular phenotype" is a phenotype detectable at the level of a population of (one or more) molecules. Such molecules can be nucleic acids such as genomic DNA or RNA, proteins, or metabolites. For example, a molecular phenotype can be an expression profile for one or more gene products, e.g., at a specific stage of plant development, in response to an environmental condition or stress, etc. Expression profiles are typically evaluated at the level of RNA or protein, e.g., on a nucleic acid array or "chip" or using antibodies or other binding proteins.

The term "yield" refers to the productivity per unit area of a particular plant product of commercial value. For example, yield of soybean is commonly measured in bushels of seed per acre or metric tons of seed per hectare per season. Yield is affected by both genetic and environmental factors. "Agronomics," "agronomic traits," and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability,. threshability and the like. Yield is, therefore, the final culmination of all agronomic traits.

A "set" of markers or probes refers to a collection or group of markers or probes, or the data derived therefrom, used for a common purpose, e.g., identifying soybean plants with a desired trait (e.g., tolerance to *Sclerotinia* infection). Frequently, data corresponding to the markers or probes, or data derived from their use, is stored in an electronic medium. While each of the members of a set possess utility with respect to the specified purpose, individual markers selected from the set as well as subsets including some, but not all of the markers, are also effective in achieving the specified purpose.

A "look up table" is a table that correlates one form of data to another, or one or more forms of data with a predicted outcome that the data is relevant to. For example, a look up table can include a correlation between allele data and a predicted trait that a plant comprising a given allele is likely to display. These tables can be, and typically are, multidimensional, e.g., taking multiple alleles into account simultaneously, and, optionally, taking other factors into account as well, such as genetic background, e.g., in making a trait prediction.

A "computer readable medium" is an information storage media that can be accessed by a computer using an available or custom interface. Examples include memory (e.g., ROM or RAM, flash memory, etc.), optical storage media (e.g., CD-ROM), magnetic storage media (computer hard drives, floppy disks, etc.), punch cards, and many others that are commercially available. Information can be transmitted between a system of interest and the computer, or to or from the computer to or from the computer readable medium for storage or access of stored information. This transmission can be an electrical transmission, or can be made by other available methods, such as an IR link, a wireless connection, or the like.

"System instructions" are instruction sets that can be partially or fully executed by the system. Typically, the instruction sets are present as system software.

BRIEF DESCRIPTION OF THE FIGURES

FIG. 1 provides a table listing soybean markers demonstrating linkage disequilibrium with *Sclerotinia* infection tolerance/susceptibility phenotype as determined by intergroup allele frequency distribution analysis, association mapping analysis and QTL interval mapping (including single marker regression analysis) methods. The table indicates the genomic-SSR or EST-SSR marker type (all simple sequence repeats) or SNP markers, the chromosome on which the marker is located and its approximate genetic map position relative to other known markers, given in cM, with position zero being the first (most distal) marker on the chromosome, as provided in the integrated genetic map in FIG. 7. Also shown are the soybean populations used in the analysis and the statistical probability of random segregation of the marker and the tolerance/susceptibility phenotype given as an adjusted probability taking into account the variability and false positives of multiple tests. Probability values from single marker regression are also shown.

FIG. 2 provides a table listing genomic and EST SSR markers, including those markers that demonstrated linkage disequilibrium with the *Sclerotinia* infection tolerance phenotype. The table provides the sequences of the left and right PCR primers used in the SSR marker locus genotyping analysis. Also shown is the pigtail sequence used on the 5' end of the right primer, and the number of nucleotides in the tandem repeating element in the SSR.

FIG. 3 provides a table listing the SNP markers that demonstrated linkage disequilibrium with the *Sclerotinia* infection tolerance phenotype. The table provides the sequences of the PCR primers used to generate a SNP-containing amplicon, and the allele-specific probes that were used to identify the SNP allele in an allele-specific hybridization assay (ASH assay).

FIG. 4 provides an allele dictionary for the alleles of the SSR markers shown in FIG. 1, including those markers that demonstrated linkage disequilibrium with the *Sclerotinia* infection tolerance phenotype. Each allele is defined by the size of a PCR amplicon generated from soybean genomic DNA or mRNA using the primers listed in FIG. 2. Sizes of the PCR amplicons are indicated in base pairs (bp).

FIG. 5 provides a table showing the SAG1048 marker genotypes (i.e., the observed alleles) in each of the *Sclerotinia* stem rot tolerant (TOL) and susceptible (SUS) soybean strains used in the Intergroup Allele Frequency Distribution Analysis. The numbers (e.g., 1, 2, 3, etc., or combinations thereof) in the Marker Allele column correspond to the SSR allele, as listed in the allele dictionary in FIG. 4. In some cases, more than one SSR allele appears in the analyzed DNA sample, and both alleles are listed.

FIG. 6 provides a table listing genetic markers that are closely linked to the *Sclerotinia* tolerance markers identified by the present invention.

FIG. 7 provides an integrated genetic map for approximately 750 soybean markers, including both SSR-type and SNP-type markers. These markers are distributed over each soybean chromosome. The chromosome number, as well as the equivalent historical chromosome name are indicated. The genetic map positions of the markers are indicated in centiMorgans (cM), typically with position zero being the first (most distal) marker on the chromosome.

DETAILED DESCRIPTION

*Sclerotinia* stem rot is a disease causing reduced plant viability and reductions in yield, including soybean. The disease is caused by infection with the fungal pathogen *Sclerotinia sclerotiorum*. Soybean yield losses from *Sclerotinia sclerotiorum* infection can be minimized by the field application of fungicides such as thiophanate-methyl (Topsin®-M).

An effective and environmentally compatible approach to overcoming this disease would be through the selection of naturally disease resistant varieties. However, the strong selective pressures that resistant soybean impose on *Sclerotinia* cause relatively rapid loss of resistance against races of *Sclerotinia* that evolve to combat resistance traits in the resistant soybean. Accordingly, tolerance to *Sclerotinia* infection, in which the plant survives, thrives and produces high yields, despite a productive *Sclerotinia* infection, is an alternate strategy to combat losses due to *Sclerotinia* infection. An advantage to tolerance, as compared simply to resistance, is that it is less likely to result in races of *Sclerotinia* that combat the tolerance traits, as the tolerant plants simply support a productive infection while maintaining high yield, regardless of the race of *Sclerotinia* at issue (tolerance can, therefore, be "non-race specific"). Thus, while it is possible that races of *Sclerotinia* may evolve to take advantage of the tolerance traits in *Sclerotinia* tolerant soybean in some manner, it is clear that the evolutionary pressures on both *Sclerotinia* and soybean are quite different than with a resistance phenotype. That is, there is not a strong negative selection against *Sclerotinia* imposed by tolerance, because tolerant soybean plants support a productive *Sclerotinia* infection.

The identification and selection of soybean plants that show tolerance to *Sclerotinia* infection using MAS can provide an effective and environmentally friendly approach to overcoming losses caused by this disease. The present invention provides soybean marker loci that demonstrate statistically significant co-segregation with *Sclerotinia* tolerance. Detection of these loci or additional linked loci can be used in marker assisted soybean breeding programs to produce tolerant plants, or plants with improved tolerance. The linked SSR markers identified herein are provided in FIG. 1. These markers include SAG1032, SATT597, SCT_026, SATT391, S60817-TB, S60239-TB, P10646A-1, P7659A-2, SATT570, SATT356, S60222-TB, SATT166, SATT448 and SAG1048.

Each of the SSR-type markers display a plurality of alleles that can be visualized as different sized PCR amplicons, as summarized in the SSR allele dictionary in FIG. 4. The PCR primers that are used to generate the SSR-marker amplicons are provided in FIG. 2. The alleles of SNP-type markers are determined using an allele-specific hybridization protocol, as known in the art.

As recognized in the art, any other marker that is linked to a QTL marker (e.g., a disease tolerance marker) also finds use for that same purpose. Examples of additional markers that are linked to the disease tolerance markers recited herein are provided. For example, a linked marker can be determined from the soybean consensus genetic map provided in FIG. 7. Additional closely linked markers are further provided in FIG. 6. It is not intended, however, that linked markers finding use with the invention be limited to those recited in FIG. 6 or 7.

The invention also provides chromosomal QTL intervals that correlate with *Sclerotinia* infection tolerance. These intervals are located on linkage groups B1, G, K and M. Any marker located within these intervals finds use as a marker for *Sclerotinia* infection tolerance. These intervals include:

(i) SAG1032 and SCT_026 (LG-B1);
(ii) S60239-TB and SATT356 (LG-G);
(iii) SATT166 and SATT448 (LG-L); and
(iv) SATT463 and SATT175 (LG-M).

Methods for identifying soybean plants or germplasm that carry preferred alleles of tolerance marker loci are a feature of the invention. In these methods, any of a variety of marker detection protocols are used to identify marker loci, depending on the type of marker loci. Typical methods for marker detection include amplification and detection of the resulting amplified markers, e.g., by PCR, LCR, transcription based amplification methods, or the like. These include ASH, SSR detection, RFLP analysis and many others.

Although particular marker alleles can show co-segregation with a disease tolerance or susceptibility phenotype, it is important to note that the marker locus is not necessarily part of the QTL locus responsible for the tolerance or susceptibility. For example, it is not a requirement that the marker polynucleotide sequence be part of a gene that imparts disease resistance (for example, be part of the gene open reading frame). The association between a specific marker allele with the tolerance or susceptibility phenotype is due to the original "coupling" linkage phase between the marker allele and the QTL tolerance or susceptibility allele in the ancestral soybean line from which the tolerance or susceptibility allele originated. Eventually, with repeated recombination, crossing over events between the marker and QTL locus can change this orientation. For this reason, the favorable marker allele may change depending on the linkage phase that exists within the tolerant parent used to create segregating populations. This does not change the fact the genetic marker can be used to monitor segregation of the phenotype. It only changes which marker allele is considered favorable in a given segregating population.

Identification of soybean plants or germplasm that include a marker locus or marker loci linked to a tolerance trait or traits provides a basis for performing marker assisted selection of soybean. Soybean plants that comprise favorable markers or favorable alleles are selected for, while soybean plants that comprise markers or alleles that are negatively correlated with tolerance can be selected against. Desired markers and/or alleles can be introgressed into soybean having a desired (e.g., elite or exotic) genetic background to produce an introgressed tolerant soybean plant or germplasm. In some aspects, it is contemplated that a plurality of tolerance markers are sequentially or simultaneous selected and/or introgressed. The combinations of tolerance markers that are selected for in a single plant is not limited, and can include a combination of markers recited in FIG. 1, any markers linked to the markers recited in FIG. 1, or any markers located within the QTL intervals defined herein.

As an alternative to standard breeding methods of introducing traits of interest into soybean (e.g., introgression), transgenic approaches can also be used. In these methods, exogenous nucleic acids that encode traits linked to markers are introduced into target plants or germplasm. For example, a nucleic acid that codes for a tolerance trait is cloned, e.g., via positional cloning and introduced into a target plant or germplasm.

Verification of tolerance can be performed by available tolerance protocols, as discussed in more detail below. For example, see Examples 4 and 5. Tolerance assays are useful to verify that the tolerance trait still segregates with the marker in any particular plant or population, and, of course, to measure the degree of tolerance improvement achieved by introgressing or recombinantly introducing the trait into a desired background.

Systems, including automated systems for selecting plants that comprise a marker of interest and/or for correlating presence of the marker with tolerance are also a feature of the invention. These systems can include probes relevant to marker locus detection, detectors for detecting labels on the probes, appropriate fluid handling elements and temperature controllers that mix probes and templates and/or amplify templates, and systems instructions that correlate label detection to the presence of a particular marker locus or allele.

Kits are also a feature of the invention. For example, a kit can include appropriate primers or probes for detecting tolerance associated marker loci and instructions in using the primers or probes for detecting the marker loci and correlating the loci with predicted *Sclerotinia* tolerance. The kits can further include packaging materials for packaging the probes, primers or instructions, controls such as control amplification reactions that include probes, primers or template nucleic acids for amplifications, molecular size markers, or the like.

Tolerance Markers and Favorable Alleles

In traditional linkage analysis, no direct knowledge of the physical relationship of genes on a chromosome is required. Mendel's first law is that factors of pairs of characters are segregated, meaning that alleles of a diploid trait separate into two gametes and then into different offspring. Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked." The frequency with which the traits are inherited together is the primary measure of how tightly the traits are linked, i.e., traits which are inherited together with a higher frequency are more closely linked than traits which are inherited together with lower (but still above random) frequency. Traits are linked because the genes which underlie the traits reside on the same chromosome. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in two genes segregating separately into progeny.

A common measure of linkage is the frequency with which traits cosegregate. This can be expressed as a percentage of cosegregation (recombination frequency) or, also commonly, in centiMorgans (cM). The cM is named after the pioneering geneticist Thomas Hunt Morgan and is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency. For example, in soybean, 1 cM correlates, on average, to about 400,000 base pairs (400 Kb).

Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation. The markers herein, as described in FIG. 1, e.g., SAG1032, SATT597, SCT_026, SATT391, S60817-TB, S60239-TB, P10646A-1, P7659A-2, SATT570, SATT356, S60222-TB, SATT166, SATT448 and SAG1048, as well as any of the chromosome intervals (i) SAG1032 and SCT_026 (LG-B1);
(ii) S60239-TB and SATT356 (LG-G);
(iii) SATT166 and SATT448 (LG-L); and
(iv) SATT463 and SATT175 (LG-M).

have been found to correlate with tolerance, improved tolerance or susceptibility to *Sclerotinia* infection in soybean. This means that the markers are sufficiently proximal to a tolerance trait that they can be used as a predictor for the tolerance trait. This is extremely useful in the context of marker assisted selection (MAS), discussed in more detail herein. In brief, soybean plants or germplasm can be selected for markers or marker alleles that positively correlate with tolerance, without actually raising soybean and measuring for tolerance or improved tolerance (or, contrawise, soybean plants can be selected against if they possess markers that negatively correlate with tolerance or improved tolerance). MAS is a powerful shortcut to selecting for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In some embodiments, the most preferred QTL markers are a subset of the markers provided in FIG. 1. For example, the most preferred markers can be selected from SAG1032, SATT391, S60817-TB., S60239-TB, S60222-TB, SATT166, SATT448 and SAG1048.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (i.e., the two loci are "out of phase" with each other).

A favorable allele of a marker is that allele of the marker that co-segregates with a desired phenotype (e.g., disease tolerance). As used herein, a QTL marker has a minimum of one favorable allele, although it is possible that the marker might have two or more favorable alleles found in the population. Any favorable allele of that marker can be used advantageously for the identification and construction of tolerant soybean lines. Optionally, one, two, three or more favorable allele(s) of different markers are identified in, or introgressed into a plant, and can be selected for or against during MAS. Desirably, plants or germplasm are identified that have at least one such favorable allele that positively correlates with tolerance or improved tolerance.

Alternatively, a marker allele that co-segregates with disease susceptibility also finds use with the invention, since that allele can be used to identify and counter select disease-susceptible plants. Such an allele can be used for exclusionary purposes during breeding to identify alleles that negatively correlate with tolerance, to eliminate susceptible plants or germplasm from subsequent rounds of breeding.

In some embodiments of the invention, a plurality of marker alleles are simultaneously selected for in a single plant or a population of plants. In these methods, plants are selected that contain favorable alleles from more than one tolerance marker, or alternatively, favorable alleles from more than one tolerance marker are introgressed into a desired soybean germplasm. One of skill in the art recognizes that the simultaneous selection of favorable alleles from more than one disease tolerance marker in the same plant is likely to result in an additive (or even synergistic) protective effect for the plant.

One of skill recognizes that the identification of favorable marker alleles is germplasm-specific. The determination of which marker alleles correlate with tolerance (or susceptibility) is determined for the particular germplasm under study. One of skill recognizes that methods for identifying the favorable alleles are routine and well known in the art, and furthermore, that the identification and use of such favorable alleles is well within the scope of the invention. Furthermore still, identification of favorable marker alleles in soybean populations other than the populations used or described herein is well within the scope of the invention.

Amplification primers for amplifying SSR-type marker loci are a feature of the invention. FIG. 2 provides specific primers for marker locus amplification. However, one of skill will immediately recognize that other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the invention is not limited to the primers and probes specifically recited herein.

In some aspects, methods of the invention utilize an amplification step to detect/genotype a marker locus. However, it will be appreciated that amplification is not a requirement for marker detection—for example, one can directly detect unamplified genomic DNA simply by performing a Southern blot on a sample of genomic DNA. Procedures for performing Southern blotting, amplification (PCR, LCR, or the like) and many other nucleic acid detection methods are well established and are taught, e.g., in Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis et al. eds) Academic Press Inc. San Diego, Calif. (1990) (Innis). Additional details regarding detection of nucleic acids in plants can also be found, e.g., in *Plant Molecular Biology* (1993) Croy (ed.) BIOS Scientific Publishers, Inc.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Typically, molecular markers are detected by any established method available in the art, including, without limitation, allele specific hybridization (ASH) or other methods for detecting single nucleotide polymorphisms (SNP), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, isozyme markers detection, or the like. While the exemplary markers provided in the figures and tables herein are either SSR or SNP (ASH) markers, any of the aforementioned marker types can be employed in the context of the invention to identify chromosome segments encompassing genetic element that contribute to superior agronomic performance (e.g., tolerance or improved tolerance).

QTL Chromosome Intervals

In some aspects, the invention provides QTL chromosome intervals, where a QTL (or multiple QTLs) that segregate with *Sclerotinia* disease tolerance are contained in those intervals. A variety of methods well known in the art are available for identifying chromosome intervals (also as described in detail in EXAMPLE 3). The boundaries of such chromosome intervals are drawn to encompass markers that will be linked to one or more QTL. In other words, the chromosome interval is drawn such that any marker that lies within that interval (including the terminal markers that define the boundaries of the interval) can be used as markers for disease tolerance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTL. Regardless, knowledge of how many QTL are in a particular interval is not necessary to make or practice the invention.

The present invention provides soybean chromosome intervals, where the markers within that interval (including the markers that define the termini of the interval) demonstrate co-segregation with tolerance to *Sclerotinia* infection. Thus, each of these intervals comprises at least one *Sclerotinia* tolerance QTL. These intervals are:

| Linkage Group | Flanking Markers | Method(s) of Identification |
| --- | --- | --- |
| B1 | SAG1032 and SCT_026 | Marker Clustering |
| G | S60239-TB and SATT356 | Marker Clustering |
| L | SATT166 and SATT448 | Marker Clustering |
| M | SATT463 and SATT175 | Linkage to a preferred marker |

Each of the intervals described above shows a clustering of markers that co-segregate with *Sclerotinia* disease tolerance. This clustering of markers occurs in relatively small domains on the linkage groups, indicating the presence of one or more QTL in those chromosome regions. QTL intervals were drawn to encompass the markers that co-segregate with pathogen tolerance. The intervals are defined by the markers on their termini, where the interval encompasses all the markers that map within the interval as well as the markers that define the termini.

In some cases, an interval can be drawn, where the interval is defined by linkage to a preferred marker. For example, an interval on LG M is defined, where any marker that is linked to the marker SAG1048 is a member of that interval. For example, as used here, linkage is defined as any marker that is within 10 cM from SAG1048. This interval on LG M is further illustrated in FIG. 6. The experimentally demonstrated marker SAG1048 is shown, as are markers that are linked to SAG1048 (e.g., within 10 cM of SAG1048) as determined by any suitable genetic linkage map (for example, Song et al., (2004) "A New Integrated Genetic Linkage Map of the Soybean," Theor. Appl. Genet., 109:122-128). These markers are shown in genetic order. Each of the markers listed, including the terminal markers SATT463 and SATT175, are members of the interval. The SATT463 and SATT175 markers are known in the art (see, for example, GenBank Accession Numbers BH126636 and BH126384, and FIG. 2 which provides primers suitable for amplification of these marker sequences).

As described above, an interval (e.g., a chromosome interval or a QTL interval) need not depend on an absolute measure of interval size such as a centimorgans value. An interval can be described by the terminal markers that define the endpoints of the interval, and typically the interval will include the terminal markers that define the extent of the interval. An interval can include any marker localizing within that chromosome domain, whether those markers are currently known or unknown. The invention provides a variety of means for defining a chromosome interval, for example, in the marker loci provided in the genetic map in FIG. 7, in the lists of linked markers of FIG. 6, and in references cited herein (e.g., Song et al., (2004) "A New Integrated Genetic Linkage Map of the Soybean," Theor. Appl. Genet., 109:122-128).

Genetic Maps

As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL/marker genetic map relationships. However, it is not intended that the invention be limited to any particular mapping populations, use of any particular software, or any particular set of software parameters to determine linkage of a particular marker or chromosome interval with the *Sclerotinia* tolerance phenotype. It is well within the ability of one of ordinary skill in the art to extrapolate the novel features described herein to any soybean gene pool or population of interest, and using any particular software and software parameters. Indeed, observations regarding tolerance markers and chromosome intervals in populations in additions to those described herein are readily made using the teaching of the present disclosure.

Mapping Populations

Any suitable soybean strains can be used to generate mapping data or for marker association studies. A large number of commonly used soybean lines (e.g., commercial varieties) and mapping populations are known in the art. Additional strains finding use with the invention are also described in the present disclosure. Useful soybean mapping populations and lines include but are not limited to:

| Mapping Population | Description/Reference |
|---|---|
| UP1C6-43 × 90B73 | UP1C6-43 is a public line from the University of Nebraska.. 90B73 is described in Plant Variety Protection Act, Certificate No. 200000152 for Soybean '90B73' issued May 8, 2001; see also, U.S. Pat. No. 6,316,700, issued Nov. 13, 2001, to Hedges. |
| P1082 × 90B73 | P1082 is described in Plant Variety Protection Act, Certificate No. 8200115, issued May 26, 1982. 90B73 is described in Plant Variety Protection Act, Certificate No. 200000152 for Soybean '90B73' issued May 8, 2001; see also, U.S. Pat. No. 6,316,700, issued Nov. 13, 2001, to Hedges. |
| Minsoy × Noir 1 | Recombinant Inbred Line (RIL) population derived by single seed descent, consisting of 240 F7-derived RILs. Described in Lark et al., (1993) "A genetic map of soybean (*Glycine max* L.) and using an intraspecific cross of two cultivars: Minosy and Noir 1," Theor. Appl. Genet., 86: 901-906; Mansur and Orf (1995) "Evaluation of soybean recombinant inbreds for agronomic performance in northern USA and Chile," Crop Sci., 35: 422-425; Mansur et al., (1996) "Genetic mapping of agronomic traits using recombinant inbred lines of soybean," Crop Sci., 36: 1327-1336. Developed at the University of Utah. See also Intl. patent application No. WO 98/49887, filed May 1, 1998. |
| Minsoy × Archer | RIL population derived by single seed descent, consisting of 233 F7-derived RILs. Described in Mansur and Orf (1995) "Evaluation of soybean recombinant inbreds for agronomic performance in northern USA and Chile," Crop Sci., 35: 422-425; Mansur et al., (1996) "Genetic mapping of agronomic traits using recombinant inbred lines of soybean," Crop Sci., 36: 1327-1336. Developed at the University of Utah. See also Intl. patent application No. WO 98/49887, filed May 1, 1998. |
| Noir 1 × Archer | RIL Population derived by single seed descent, consisting of 240 F7-derived RILs. Described in Mansur and Orf (1995) "Evaluation of soybean recombinant inbreds for agronomic performance in northern USA and Chile," Crop Sci., 35: 422-425; Mansur et al., (1996) "Genetic mapping of agronomic traits using recombinant inbred lines of soybean," Crop Sci., 36: 1327-1336. Developed at the University of Utah. See also Intl. patent application No. WO 98/49887, filed May 1, 1998. |
| Clark × Harosoy | Population derived from the cross of near isogenic lines (NILs) of the cultivars Clark and Harosoy. The population consists of derivatives of 57 F2 plants (see, Shoemaker and Specht (1995) "Integration of the soybean molecular and classical genetic linkage groups," Crop Sci., 35: 436-446). Developed at the University of Nebraska. |
| A81-356022 × PI468916 | This is an F2-derived mapping population from the interspecific cross of the A81-356022 (*Glycine max*) and PI468.916 (*G. soja*). The population consists of 59 F2 plant derivatives and has been described in detail (Keim et al., (1990) "RFLP mapping in soybean: association between marker loci and variation in quantitative traits," Genetics 126: 735-742; Shoemaker and Specht (1995) "Integration of the soybean molecular and classical genetic linkage groups," Crop Sci., 35: 436-446; Shoemaker and Olson (1993) Molecular linkage map of soybean (*Glycine max* L. Merr.). p.6.131-6.138, in Genetic maps: Locus maps of complex genomes [O'Brien (ed.)] Cold Spring Harbor Laboratory Press, New York). Commonly referred to as the USDA/Iowa State University Population (MS). |

-continued

| Mapping Population | Description/Reference |
| --- | --- |
| OX715 × P9242 | OX715 is a public variety. P9242 is described in Plant Variety Protection Act, Certificate No. 9300238 for Soybean '9242' issued May 30, 1997. |
| Sloan, Williams, Harosoy and Conrad (various RILs derived from crosses of the above cultivars) | See, Burnham et al., Crop Sci., "Quantitative Trait Loci for Partial Resistance to *Phytophthora sojae* in Soybean," 43: 1610-1617 (2003); Weiss and Stevenson, Agron. J., 47: 541-543 (1955); Bernard and Lindahl, Crop Sci., 43: 101-105 (1972); Bahrenfus and Fehr, Crop Sci., 20: 673 (1980); Fehr et al., Crop Sci., 29: 830 (1989). |
| Bert, Marcus, Corsoy, A92-627030, Simpson, OT92-1, Hendricks, Freeborn, Surge, Kenwood 94 (various RILs derived from crosses of the above cultivars) | See, Glover and Scott, "Heritability and Phenotypic Variation of Tolerance to *Phytophthora* Root Rot of Soybean," Crop Sci., 38: 1495-1500 (1998); and additional references made therein. |
| Essex × Forrest Flyer × Hartwig | See, Yuan et al., "Quantitative trait loci in two soybean recombinant inbred line populations segregating for yield and disease resistance," Crop Sci., 42: 271-277 (2002). |
| Williams × PI399073 | U.S. patent application No. 2004/0034890, published Feb. 19, 2004; |
| S 19-90 × PI399073 | U.S. patent application No. 2004/0261144, published Dec. 23, 2004. |
| 9163 × 92B05 | P9163 is a commercially available Pioneer variety described in Plant Variety Protection Act, Certificate No. 9600053. 92B05 is a commercially available Pioneer variety described in Plant Variety Protection Act, Certificate No. 9900092 for Soybean '92B05' issued Sep. 21, 2000; see also, U.S. Pat. No. 5,942,668, issued Aug. 24, 1999 to Grace et al. |
| 9362 × 93B41 | P9362 is a commercially available Pioneer variety described in Plant Variety Protection Act, Certificate No. 9400098. 93B41 is a commercially available Pioneer variety described in Plant Variety Protection Act, Certificate No. 9800068; see also, U.S. Pat. No. 5,750,853, issued May 12, 1998 to Fuller et al. |
| 93B35 | Described in Plant Variety Protection Act, Certificate No. 200000035, issued Apr. 24, 2001. See also, U.S. Pat. No. 6,153,818, issued Nov. 28, 2000. |
| 93B53 | Described in Plant Variety Protection Act, Certificate No. 9900101, issued Oct. 27, 2000. See also, U.S. Pat. No. 6,075,182, issued Jun. 13, 2000. |
| 93M11 | Described in Plant Variety Protection Act, Certificate No. 200400080, issued Aug. 16, 2004. See also, U.S. Pat. No. 6,855,875, issued Feb. 15, 2005. |
| 93B68 | Described in Plant Variety Protection Act, Certificate No. 200200084, issued Jun. 10, 2002. See also, U.S. patent application Ser. No. 10/271,115. |
| 93B72 | Described in Plant Variety Protection Act, Certificate No. 200100071, issued May 8, 2001. See also, U.S. Pat. No. 6,566,589, issued May 20, 2003. |
| 94B53 | Described in Plant Variety Protection Act, Certificate No. 200000031, issued May 8, 2001. See also, U.S. Pat. No. 6,235,976, issued May 22, 2001. |
| 94M80 | Described in pending Plant Variety Protection Act, Certificate No. 200500084, filed Jan. 18, 2005. See also, pending U.S. patent application Ser. No. 10/768,275, filed Jan. 30, 2005. |
| 9492 | Described in Plant Variety Protection Act, Certificate No. 9800077, issued Sep. 12, 2001. See also, U.S. Pat. No. 5,792,907, issued Aug. 11, 1998. |

Mapping Software

A variety of commercial software is available for genetic mapping and marker association studies (e.g., QTL mapping). This software includes but is not limited to:

| Software | Description/References |
| --- | --- |
| JoinMap ® | VanOoijen, and Voorrips (2001) "JoinMap 3.0 software for the calculation of genetic linkage maps," Plant Research International, Wageningen, the Netherlands; and, Stam "Construction of integrated genetic linkage maps by means of a new computer package: JoinMap," The Plant Journal 3(5): 739-744 (1993) |
| MapQTL ® | J. W. vanOoijen, "Software for the mapping of quantitative trait loci in experimental populations," Kyazma B. V., Wageningen, Netherlands |

| Software | Description/References |
|---|---|
| MapManager QT | Manly and Olson, "Overview of QTL mapping software and introduction to Map Manager QT," Mamm. Genome 10: 327-334 (1999) |
| MapManager QTX | Manly, Cudmore and Meer, "MapManager QTX, cross-platform software for genetic mapping," Mamm. Genome 12: 930-932 (2001) |
| GeneFlow ® and QTLocate ™ | GENEFLOW, Inc. (Alexandria, VA) |
| TASSEL | (Trait Analysis by aSSociation, Evolution, and Linkage) by Edward Buckler, and information about the program can be found on the Buckler Lab web page at the Institute for Genomic Diversity at Cornell University. |

Unified Genetic Maps

"Unified," "consensus" or "integrated" genetic maps have been created that incorporate mapping data from two or more sources, including sources that used different mapping populations and different modes of statistical analysis. The merging of genetic map information increases the marker density on the map, as well as improving map resolution. These improved maps can be advantageously used in marker assisted selection, map-based cloning, provide an improved framework for positioning newly identified molecular markers and aid in the identification of QTL chromosome intervals and clusters of advantageously-linked markers.

In some aspects, a consensus map is derived by simply overlaying one map on top of another. In other aspects, various algorithms, e.g., JoinMap® analysis, allows the combination of genetic mapping data from multiple sources, and reconciles discrepancies between mapping data from the original sources. See, Van Ooijen, and Voorrips (2001) "Join-Map 3.0 software for the calculation of genetic linkage maps," Plant Research International, Wageningen, the Netherlands; and, Stam (1993) "Construction of integrated genetic linkage maps by means of a new computer package: Join-Map," The Plant Journal 3(5):739-744.

FIG. 7 provides a composite genetic map that incorporates mapping information from various sources. This map was derived using the USDA/Iowa State University mapping population data (as described in Cregan et al., "An Integrated Genetic Linkage Map of the Soybean Genome" Crop Science 39:1464-1490 [1999]; and see references therein) as a framework. Additional markers, as they became known, have been continuously added to that map, including public SSR markers, EST-derived markers, and SNP markers. This map contains approximately 750 soybean markers that are distributed over each of the soybean chromosomes. The markers that are on this map are known in the art (i.e., have been previously described; see, e.g., the SOYBASE on-line resource for extensive listings of these markers and descriptions of the individual markers) or are described herein.

Additional integrated maps are known in the art. See, e.g., Cregan et al., "An Integrated Genetic Linkage Map of the Soybean Genome" Crop Science 39:1464-1490 (1999); and also International Application No. PCT/US2004/024919 by Sebastian, filed Jul. 27, 2004, entitled "Soybean Plants Having Superior Agronomic Performance and Methods for their Production").

Song et al. provides another integrated soybean genetic map that incorporates mapping information from five different mapping populations (Song et al., "A New Integrated Genetic Linkage Map of the Soybean," Theor. Appl. Genet., 109:122-128 [2004]). This integrated map contains approximately 1,800 soybean markers, including SSR and SNP-type markers, as well as EST markers, RPLP markers, AFLP, RAPD, isozyme and classical markers (e.g., seed coat color). The markers that are on this map are known in the art and have been previously characterized. This information is also available at the website for the Soybean Genomics and Improvement Laboratory (SGIL) at the USDA Beltsville Agricultural Research Center (BARC). See, specifically, the description of projects in the Cregan Laboratory on that website.

The soybean integrated linkage map provided in Song et al. (2004) is based on the principle described by Stam (1993) "Construction of integrated genetic linkage maps by means of a new computer package: JoinMap," The Plant Journal 3(5): 739-744; and Van Ooijen and Voorrips (2001) "JoinMap 3.0 software for the calculation of genetic linkage maps," Plant Research International, Wageningen, the Netherlands. Mapping information from five soybean populations was used in the map integration, and also used to place recently identified SSR markers onto the soybean genome. These mapping populations were Minsoy×Noir 1 (MN), Minsoy×Archer (MA), Noir 1×Archer (NA), Clark×Harosoy (CH) and A81-356022×PI468916 (MS). The JoinMap® analysis resulted in a map with 20 linkage groups containing a total of 1849 markers, including 1015 SSRs, 709 RFLPs, 73 RAPDs, 24 classical traits, six AFLPs, ten isozymes and 12 others. Among the mapped SSR markers were 417 previously uncharacterized SSRs.

Initially, LOD scores and pairwise recombination frequencies between markers were calculated. A LOD of 5.0 was used to create groups in the MS, MA, NA populations and LOD 4.0 in the MN and CH populations. The map of each linkage group was then integrated. Recombination values were converted to genetic distances using the Kosambi mapping function.

Linked Markers

From the present disclosure and widely recognized in the art, it is clear that any genetic marker that has a significant probability of co-segregation with a phenotypic trait of interest (e.g., in the present case, a pathogen tolerance or improved tolerance trait) can be used as a marker for that trait. A list of useful QTL markers provided by the present invention is provided in FIG. 1.

In addition to the QTL markers noted in FIG. 1, additional markers linked to (showing linkage disequilibrium with) the QTL markers can also be used to predict the tolerance or improved tolerance trait in a soybean plant. In other words, any other marker showing less than 50% recombination frequency (separated by a genetic distance less than 50 cM) with a QTL marker of the invention (e.g., the markers provided in FIG. 1) is also a feature of the invention. Any marker that is linked to a QTL marker can also be used advantageously in marker-assisted selection for the particular trait.

Genetic markers that are linked to QTL markers (e.g., QTL markers provided in FIG. 1) are particularly useful when they are sufficiently proximal (e.g., closely linked) to a given QTL marker so that the genetic marker and the QTL marker display a low recombination frequency. In the present invention, such closely linked markers are a feature of the invention. As defined herein, closely linked markers display a recombination frequency of about 10% or less (the given marker is within 10 cM of the QTL). Put another way, these closely linked loci co-segregate at least 90% of the time. Indeed, the closer a marker is to a QTL marker, the more effective and advantageous that marker becomes as an indicator for the desired trait.

Thus, in other embodiments, closely linked loci such as a QTL marker locus and a second locus display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus such as a QTL) display a recombination a frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

In some aspects, linked markers (including closely linked markers) of the invention are determined by review of a genetic map, for example, the integrated genetic map shown in FIG. 7. For example, it is shown herein that the linkage group L marker SATT166 correlates with at least one Sclerotinia tolerance QTL. Markers that are linked to SATT166 can be determined from the map provided in FIG. 7. For example, markers on linkage group A1 that are closely linked to SATT166 include:

| Marker | Linkage Group | Map Position (cM) |
| --- | --- | --- |
| SCT_010 | L | 68.5 |
| SATT076 | L | 72.3 |
| SATT265 | L | 75.0 |
| SATT527 | L | 75.7 |
| SATT561 | L | 75.7 |
| SATT166 | L | 77.1 |
| SATT448 | L | 78.0 |
| SATT678 | L | 80.9 |

Similarly, linked markers (including closely linked markers) of the invention can be determined by review of any suitable soybean genetic map. For example, the integrated genetic map described in Song et al. (2004) also provides a means to identify linked (including closely linked) markers. See, Song et al., "A New Integrated Genetic Linkage Map of the Soybean," Theor. Appl. Genet., 109:122-128 [2004]; see also the website for the Soybean Genomics and Improvement Laboratory (SGIL) at the USDA Beltsville Agricultural Research Center (BARC), and see specifically the description of projects in the Cregan Laboratory on that website. That genetic map incorporates a variety of genetic markers that are known in the art or alternatively are described in that reference. Detailed descriptions of numerous markers, including many of those described in Song et al. (2004) can be found at the SOYBASE website resource.

For example, according to the Song et al. (2004) integrated genetic map, markers on linkage group A1 that are closely linked to SATT166 include: Sct_010, Satt076, Satt448, gy3E_1, Satt166, Sat_113, Satt678, Satt527, Satt561, L050_8 and A132_2. In some embodiments, these linked markers form an interval, where the interval is defined by the terminal markers Sct_010 and A132_2.

It is not intended that the determination of linked or closely linked markers be limited to the use of any particular soybean genetic map. Indeed, a large number of soybean genetic maps is available and are well known to one of skill in the art. Another map that finds use with the invention in this respect is the integrated soybean genetic maps found on the SOYBASE website resource. Alternatively still, the determination of linked and closely linked markers can be made by the generation of an experimental dataset and linkage analysis.

It is not intended that the identification of markers that are linked (e.g., within about 50 cM or within about 10 cM) to the Sclerotinia tolerance QTL markers identified herein be limited to any particular map or methodology. The integrated genetic map provided in FIG. 7 serves only as example for identifying linked markers. Indeed, linked markers as defined herein can be determined from any genetic map known in the art (an experimental map or an integrated map), or alternatively, can be determined from any new mapping dataset.

It is noted that lists of linked and closely linked markers may vary between maps and methodologies due to various factors. First, the markers that are placed on any two maps may not be identical, and furthermore, some maps may have a greater marker density than another map. Also, the mapping populations, methodologies and algorithms used to construct genetic maps can differ. One of skill in the art recognizes that one genetic map is not necessarily more or less accurate than another, and furthermore, recognizes that any soybean genetic map can be used to determine markers that are linked and closely linked to the QTL markers of the present invention.

Techniques for Marker Detection

The invention provides molecular markers that have a significant probability of co-segregation with QTL that impart a Sclerotinia tolerance phenotype. These QTL markers find use in marker assisted selection for desired traits (tolerance or improved tolerance), and also have other uses. It is not intended that the invention be limited to any particular method for the detection of these markers.

Markers corresponding to genetic polymorphisms between members of a population can be detected by numerous methods well-established in the art (e.g., PCR-based sequence specific amplification, restriction fragment length polymorphisms (RFLPs), isozyme markers, allele specific hybridization (ASH), amplified variable sequences of the plant genome, self-sustained sequence replication, simple sequence repeat (SSR), single nucleotide polymorphism (SNP), random amplified polymorphic DNA ("RAPD") or amplified fragment length polymorphisms (AFLP). In one additional embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In general, the majority of genetic markers rely on one or more property of nucleic acids for their detection. For example, some techniques for detecting genetic markers utilize hybridization of a probe nucleic acid to nucleic acids corresponding to the genetic marker (e.g., amplified nucleic acids produced using genomic soybean DNA as a template). Hybridization formats, including but not limited to solution phase, solid phase, mixed phase, or in situ hybridization assays are useful for allele detection. An extensive guide to the hybridization of nucleic acids is found in Tijssen (1993) *Laboratory Techniques in Biochemistry and Molecular Biology—Hybridization with Nucleic Acid Probes* Elsevier, N.Y., as well as in Sambrook, Berger and Ausubel (herein).

For example, markers that comprise restriction fragment length polymorphisms (RFLP) are detected, e.g., by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals or populations. Determining one or more restriction enzyme that produces informative fragments for each cross is a simple procedure, well known in the art. After separation by length in an appropriate matrix (e.g., agarose or polyacrylamide) and transfer to a membrane (e.g., nitrocellulose, nylon, etc.), the labeled probe is hybridized under conditions which result in equilibrium binding of the probe to the target followed by removal of excess probe by washing.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eigth Edition* by Molecular Probes, Inc. (Eugene Oreg.) (Available on CD ROM).

Amplification-based Detection Methods

PCR, RT-PCR and LCR are in particularly broad use as amplification and amplification-detection methods for amplifying nucleic acids of interest (e.g., those comprising marker loci), facilitating detection of the markers. Details regarding the use of these and other amplification methods can be found in any of a variety of standard texts, including, e.g., Sambrook, Ausubel, Berger and Croy, herein. Many available biology texts also have extended discussions regarding PCR and related amplification methods. One of skill will appreciate that essentially any RNA can be converted into a double stranded DNA suitable for restriction digestion, PCR expansion and sequencing using reverse transcriptase and a polymerase ("Reverse Transcription-PCR, or "RT-PCR"). See also, Ausubel, Sambrook and Berger, above.

Real Time Amplification/Detection Methods

In one aspect, real time PCR or LCR is performed on the amplification mixtures described herein, e.g., using molecular beacons or TaqMan™ probes. A molecular beacon (MB) is an oligonucleotide or PNA which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched. Details regarding standard methods of making and using MBs are well established in the literature and MBs are available from a number of commercial reagent sources. See also, e.g., Leone et al. (1995) "Molecular beacon probes combined with amplification by NASBA enable homogenous real-time detection of RNA." *Nucleic Acids Res.* 26:2150-2155; Tyagi and Kramer (1996) "Molecular beacons: probes that fluoresce upon hybridization" *Nature Biotechnology* 14:303-308; Blok and Kramer (1997) "Amplifiable hybridization probes containing a molecular switch" *Mol Cell Probes* 11:187-194; Hsuih et al. (1997) "Novel, ligation-dependent PCR assay for detection of hepatitis C in serum" *J Clin Microbiol* 34:501-507; Kostrikis et al. (1998) "Molecular beacons: spectral genotyping of human alleles" *Science* 279:1228-1229; Sokol et al. (1998) "Real time detection of DNA:RNA hybridization in living cells" *Proc. Natl. Acad. Sci. U.S.A.* 95:11538-11543; Tyagi et al. (1998) "Multicolor molecular beacons for allele discrimination" *Nature Biotechnology* 16:49-53; Bonnet et al. (1999) "Thermodynamic basis of the chemical specificity of structured DNA probes" *Proc. Natl. Acad. Sci. U.S.A.* 96:6171-6176; Fang et al. (1999) "Designing a novel molecular beacon for surface-immobilized DNA hybridization studies" *J. Am. Chem. Soc.* 121:2921-2922; Marras et al. (1999) "Multiplex detection of single-nucleotide variation using molecular beacons" *Genet. Anal. Biomol. Eng.* 14:151-156; and Vet et al. (1999) "Multiplex detection of four pathogenic retroviruses using molecular beacons" *Proc. Natl. Acad. Sci. U.S.A.* 96:6394-6399. Additional details regarding MB construction and use is found in the patent literature, e.g., U.S. Pat. No. 5,925,517 (Jul. 20, 1999) to Tyagi et al. entitled "Detectably labeled dual conformation oligonucleotide probes, assays and kits;" U.S. Pat. No. 6,150,097 to Tyagi et al (Nov. 21, 2000) entitled "Nucleic acid detection probes having non-FRET fluorescence quenching and kits and assays including such probes" and U.S. Pat. No. 6,037,130 to Tyagi et al (Mar. 14, 2000), entitled "Wavelength-shifting probes and primers and their use in assays and kits."

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes).

Additional Details Regarding Amplified Variable Sequences, SSR, AFLP ASH, SNPs and Isozyme Markers Amplified variable sequences refer to amplified sequences of the plant genome which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Preferably, DNA from the plant serves as a template for amplification with primers that flank a variable sequence of DNA. The variable sequence is amplified and then sequenced.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) Rnase H, and (3) a DNA-dependent RNA polymerase (Guatelli et al. (1990) *Proc Natl Acad Sci USA* 87:1874). By mimicking the retroviral strategy of RNA replication by means of cDNA intermediates, this reaction accumulates cDNA and RNA copies of the original target.

Amplified fragment length polymophisms (AFLP) can also be used as genetic markers (Vos et al. (1995) *Nucl Acids Res* 23:4407). The phrase "amplified fragment length polymorphism" refers to selected restriction fragments which are amplified before or after cleavage by a restriction endonuclease. The amplification step allows easier detection of specific restriction fragments. AFLP allows the detection large numbers of polymorphic markers and has been used for genetic mapping of plants (Becker et al. (1995) *Mol Gen Genet* 249:65; and Meksem et al. (1995) *Mol Gen Genet* 249:74).

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one embodiment, ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. However, alternative modes of detection, such as hybridization, e.g., ASH, or RFLP analysis are also appropriate.

Isozyme markers can be employed as genetic markers, e.g., to track markers other than the tolerance markers herein, or to track isozyme markers linked to the markers herein. Isozymes are multiple forms of enzymes that differ from one another in their amino acid, and therefore their nucleic acid sequences. Some isozymes are multimeric enzymes contianing slightly different subunits. Other isozymes are either multimeric or monomeric but have been cleaved from the proenzyme at different sites in the amino acid seuqence. Isozymes can be characterized and analyzed at the protein level, or alternatively, isozymes which differ at the nucleic acid level can be determined. In such cases any of the nucleic acid based methods described herein can be used to analyze isozyme markers.

Additional Details Regarding Nucleic Acid Amplification

As noted, nucleic acid amplification techniques such as PCR and LCR are well known in the art and can be applied to the present invention to amplify and/or detect nucleic acids of interest, such as nucleic acids comprising marker loci. Examples of techniques sufficient to direct persons of skill through such in vitro methods, including the polymerase chain reaction (PCR), the ligase chain reaction (LCR), Qβ-replicase amplification and other RNA polymerase mediated techniques (e.g., NASBA), are found in the references noted above, e.g., Innis, Sambrook, Ausubel, Berger and Croy. Additional details are found in Mullis et al. (1987) U.S. Pat. No. 4,683,202; Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of amplifying large nucleic acids by PCR, which is useful in the context of positional cloning, are further summarized in Cheng et al. (1994) *Nature* 369: 684, and the references therein, in which PCR amplicons of up to 40 kb are generated.

Detection of Markers for Positional Cloning

In some embodiments, a nucleic acid probe is used to detect a nucleic acid that comprises a marker sequence. Such probes can be used, for example, in positional cloning to isolate nucleotide sequences linked to the marker nucleotide sequence. It is not intended that the nucleic acid probes of the invention be limited to any particular size. In some embodiments, nucleic acid probe is at least 20 nucleotides in length, or alternatively, at least 50 nucleotides in length, or alternatively, at least 100 nucleotides in length, or alternatively, at least 200 nucleotides in length.

A hybridized probe is detected using, autoradiography, fluorography or other similar detection techniques depending on the label to be detected. Examples of specific hybridization protocols are widely available in the art, see, e.g., Berger, Sambrook, and Ausubel, all herein.

Probe/Primer Synthesis Methods

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers (1981), *Tetrahedron Letts.*, 22(20): 1859-1862, e.g., using a commercially available automated synthesizer, e.g., as described in Needham-VanDevanter et al. (1984) *Nucleic Acids Res.*, 12:6159-6168. Oligonucleotides, including modified oligonucleotides can also be ordered from a variety of commercial sources known to persons of skill. There are many commercial providers of oligo synthesis services, and thus this is a broadly accessible technology. Any nucleic acid can be custom ordered from any of a variety of commercial sources, such as The Midland Certified Reagent Company, The Great American Gene Company, ExpressGen Inc., Operon Technologies Inc. (Alameda, Calif.) and many others. Similarly, PNAs can be custom ordered from any of a variety of sources, such as PeptidoGenic, HTI Bio-Products, Inc., BMA Biomedicals Ltd (U.K.), Bio•Synthesis, Inc., and many others.

In Silico Marker Detection

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

Amplification Primers for Marker Detection

In some preferred embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. As used in the art, PCR primers used to amplify a molecular marker are sometimes termed "PCR markers" or simply "markers."

It will be appreciated that, although many specific examples of primers are provided herein (see, FIG. 2), suitable primers to be used with the invention can be designed using any suitable method. It is not intended that the invention be limited to any particular primer or primer pair. For example, primers can be designed using any suitable software program, such as LASERGENE®.

In some embodiments, the primers of the invention are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose gel electrophoresis. In some embodiments, ethidium bromide staining of the PCR amplicons following size resolution allows visualization of the different size amplicons.

It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length that is longer or shorter than those given in the allele definitions in FIG. 4. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Marker alleles in addition to those recited in FIG. 4 also find use with the present invention.

Marker Assisted Selection and Breeding of Plants

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype to their progeny. Genetic markers can be used to identify plants that contain a desired genotype at one locus, or at several unlinked or linked loci (e.g., a haplotype), and that would be expected to transfer the desired genotype, along with a desired phenotype to their progeny. The present invention provides the means to identify plants, particularly soybean plants, that are tolerant, exhibit improved tolerance or are susceptible to *Sclerotinia* infection by identifying plants having a specified allele at one of those loci, e.g., SAG1032, SATT597, SCT_026, SATT391, S60817-TB, S60239-TB, P10646A-1, P7659A-2, SATT570, SATT356, S60222-TB, SATT166, SATT448 and SAG1048.

Similarly, by identifying plants lacking the desired marker locus, susceptible or less tolerant plants can be identified, and, e.g., eliminated from subsequent crosses. Similarly, these marker loci can be introgressed into any desired genomic background, germplasm, plant, line, variety, etc., as part of an overall MAS breeding program designed to enhance soybean yield.

The invention also provides chromosome QTL intervals that find equal use in MAS to select plants that demonstrate *Sclerotinia* tolerance or improved tolerance. Similarly, the QTL intervals can also be used to counter-select plants that are susceptible or have reduced tolerance to *Sclerotinia* infection. Any marker that maps within the QTL interval (including the termini of the intervals) finds use with the invention. These intervals are defined by the following pairs of markers that are the interval termini:

(i) SAG1032 and SCT_026 (LG-B1);
(ii) S60239-TB and SATT356 (LG-G);
(iii) SATT166 and SATT448 (LG-L); and
(iv) SATT463 and SATT175 (LG-M).

In general, MAS uses polymorphic markers that have been identified as having a significant likelihood of co-segregation with a tolerance trait. Such markers are presumed to map near a gene or genes that give the plant its tolerance phenotype, and are considered indicators for the desired trait, and are termed QTL markers. Plants are tested for the presence of a desired allele in the QTL marker. The most preferred markers (or marker alleles) are those that have the strongest association with the tolerance trait.

Linkage analysis is used to determine which polymorphic marker allele demonstrates a statistical likelihood of co-segregation with the tolerance phenotype (thus, a "tolerance marker allele"). Following identification of a marker allele for co-segregation with the tolerance phenotype, it is possible to use this marker for rapid, accurate screening of plant lines for the tolerance allele without the need to grow the plants through their life cycle and await phenotypic evaluations, and furthermore, permits genetic selection for the particular tolerance allele even when the molecular identity of the actual tolerance QTL is unknown. Tissue samples can be taken, for example, from the first leaf of the plant and screened with the appropriate molecular marker, and it is rapidly determined which progeny will advance. Linked markers also remove the impact of environmental factors that can often influence phenotypic expression.

A polymorphic QTL marker locus can be used to select plants that contain the marker allele (or alleles) that correlate with the desired tolerance phenotype, typically called marker-assisted selection (MAS). In brief, a nucleic acid corresponding to the marker nucleic acid allele is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, or the like. A variety of procedures for detecting markers are described herein, e.g., in the section entitled "*TECHNIQUES FOR MARKER DETECTION.*" After the presence (or absence) of a particular marker allele in the biological sample is verified, the plant is selected, e.g., used to make progeny plants by selective breeding.

Soybean plant breeders desire combinations of tolerance loci with genes for high yield and other desirable traits to develop improved soybean varieties. Screening large numbers of samples by non-molecular methods (e.g., trait evaluation in soybean plants) can be expensive, time consuming, and unreliable. Use of the polymorphic markers described herein, when genetically-linked to tolerance loci, provide an effective method for selecting resistant varieties in breeding programs. For example, one advantage of marker-assisted selection over field evaluations for tolerance resistance is that MAS can be done at any time of year, regardless of the growing season. Moreover, environmental effects are largely irrelevant to marker-assisted selection.

When a population is segregating for multiple loci affecting one or multiple traits, e.g., multiple loci involved in tolerance, or multiple loci each involved in tolerance or resistance to different diseases, the efficiency of MAS compared to phenotypic screening becomes even greater, because all of the loci can be evaluated in the lab together from a single sample of DNA. In the present instance, the SAG1032, SATT597, SCT_026, SATT391, S60817-TB, S60239-TB, P10646A-1, P7659A-2, SATT570, SATT356, S60222-TB, SATT166, SATT448 and SAG1048 markers, as well as any of the chromosome intervals:
 (i) SAG1032 and SCT_026 (LG-B1);
 (ii) S60239-TB and SATT356 (LG-G);
 (iii) SATT166 and SATT448 (LG-L); and
 (iv) SATT463 and SATT175 (LG-M), can be assayed simultaneously or sequentially from a single sample or from a plurality of parallel samples.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable tolerance marker loci) into an otherwise desirable genetic background from the recurrent parent (e.g., an otherwise high yielding soybean line). The more cycles of backcrossing that are done, the greater the genetic contribution of the recurrent parent to the resulting introgressed variety. This is often necessary, because tolerant plants may be otherwise undesirable, e.g., due to low yield, low fecundity, or the like. In contrast, strains which are the result of intensive breeding programs may have excellent yield, fecundity or the like, merely being deficient in one desired trait such as tolerance to *Sclerotinia* infection.

The presence and/or absence of a particular genetic marker or allele, e.g., SAG1032, SATT597, SCT_026, SATT391, S60817-TB, S60239-TB, P10646A-1, P7659A-2, SATT570, SATT356, S60222-TB, SATT166, SATT448 and SAG1048 markers, as well as any of the chromosome intervals
 (i) SAG1032 and SCT_026 (LG-B1);
 (ii) S60239-TB and SATT356 (LG-G);
 (iii) SATT166 and SATT448 (LG-L); and
 (iv) SATT463 and SATT175 (LG-M), in the genome of a plant is made by any method noted herein. If the nucleic acids from the plant are positive for a desired genetic marker allele, the plant can be self fertilized to create a true breeding line with the same genotype, or it can be crossed with a plant with the same marker or with other desired characteristics to create a sexually crossed hybrid generation.

Introgression of Favorable Alleles—Efficient Backcrossing of Tolerance Markers into Elite Lines One application of MAS, in the context of the present invention is to use the tolerance or improved tolerance markers to increase the efficiency of an introgression or backcrossing effort aimed at introducing a tolerance QTL into a desired (typically high yielding) background. In marker assisted backcrossing of specific markers (and associated QTL) from a donor source, e.g., to an elite or exotic genetic background, one selects among backcross progeny for the donor trait and then uses repeated backcrossing to the elite or exotic line to reconstitute as much of the elite/exotic background's genome as possible.

Thus, the markers and methods of the present invention can be utilized to guide marker assisted selection or breeding of soybean varieties with the desired complement (set) of allelic forms of chromosome segments associated with superior agronomic performance (tolerance, along with any other available markers for yield, disease resistance, etc.). Any of the disclosed marker alleles can be introduced into a soybean line via introgression, by traditional breeding (or introduced via transformation, or both) to yield a soybean plant with superior agronomic performance. The number of alleles associated with tolerance that can be introduced or be present in a soybean plant of the present invention ranges from 1 to the number of alleles disclosed herein, each integer of which is incorporated herein as if explicitly recited.

The present invention also extends to a method of making a progeny soybean plant and these progeny soybean plants, per se. The method comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for alleles associated with tolerance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant of the present invention in that it comprises at least one of the allelic forms of the markers of the present invention, such that the progeny are capable of inheriting the allele.

Often, a method of the present invention is applied to at least one related soybean plant such as from progenitor or descendant lines in the subject soybean plants pedigree such that inheritance of the desired tolerance allele can be traced. The number of generations separating the soybean plants being subject to the methods of the present invention will generally be from 1 to 20, commonly 1 to 5, and typically 1, 2, or 3 generations of separation, and quite often a direct descendant or parent of the soybean plant will be subject to the method (i.e., one generation of separation).

Introgression of Favorable Alleles—Incorporation of "Exotic" Germplasm while Maintaining Breeding Progress Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provide an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers of the present invention can be used for MAS in crosses involving elite x exotic soybean lines by subjecting the segregating progeny to MAS to maintain major yield alleles, along with the tolerance marker alleles herein.

Positional Cloning

The molecular marker loci and alleles of the present invention, e.g., SAG1032, SATT597, SCT_026, SATT391, S60817-TB, S60239-TB, P10646A-1, P7659A-2, SATT570, SATT356, S60222-TB, SATT166, SATT448 and SAG1048 markers, as well as any of the chromosome intervals
　(i) SAG1032 and SCT_026 (LG-B1);
　(ii) S60239-TB and SATT356 (LG-G);
　(iii) SATT166 and SATT448 (LG-L); and
　(iv) SATT463 and SATT175 (LG-M), can be used, as indicated previously, to identify a tolerance QTL, which can be cloned by well established procedures, e.g., as described in detail in Ausubel, Berger and Sambrook, herein.

These tolerance clones are first identified by their genetic linkage to markers of the present invention. Isolation of a nucleic acid of interest is achieved by any number of methods as discussed in detail in such references as Ausubel, Berger and Sambrook, herein, and Clark, Ed. (1997) *Plant Molecular Biology: A Laboratory Manual* Springer-Verlag, Berlin.

For example, "positional gene cloning" uses the proximity of a tolerance marker to physically define an isolated chromosomal fragment containing a tolerance QTL gene. The isolated chromosomal fragment can be produced by such well known methods as digesting chromosomal DNA with one or more restriction enzymes, or by amplifying a chromosomal region in a polymerase chain reaction (PCR), or any suitable alternative amplification reaction. The digested or amplified fragment is typically ligated into a vector suitable for replication, and, e.g., expression, of the inserted fragment. Markers that are adjacent to an open reading frame (ORF) associated with a phenotypic trait can hybridize to a DNA clone (e.g., a clone from a genomic DNA library), thereby identifying a clone on which an ORF (or a fragment of an ORF) is located. If the marker is more distant, a fragment containing the open reading frame is identified by successive rounds of screening and isolation of clones which together comprise a contiguous sequence of DNA, a process termed "chromosome walking", resulting in a "contig" or "contig map." Protocols sufficient to guide one of skill through the isolation of clones associated with linked markers are found in, e.g. Berger, Sambrook and Ausubel, all herein.

Generation of Transgenic Cells and Plants

The present invention also relates to host cells and organisms which are transformed with nucleic acids corresponding to tolerance QTL identified according to the invention. For example, such nucleic acids include chromosome intervals (e.g., genomic fragments), ORFs and/or cDNAs that encode a tolerance or improved tolerance trait. Additionally, the invention provides for the production of polypeptides that provide tolerance or improved tolerance by recombinant techniques.

General texts which describe molecular biological techniques for the cloning and manipulation of nucleic acids and production of encoded polypeptides include Berger and Kimmel, *Guide to Molecular Cloning Techniques, Methods in Enzymology volume* 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through 2004 or later) ("Ausubel")). These texts describe mutagenesis, the use of vectors, promoters and many other relevant topics related to, e.g., the generation of clones that comprise nucleic acids of interest, e.g., marker loci, marker probes, QTL that segregate with marker loci, etc.

Host cells are genetically engineered (e.g., transduced, transfected, transformed, etc.) with the vectors of this invention (e.g., vectors, such as expression vectors which comprise an ORF derived from or related to a tolerance QTL) which can be, for example, a cloning vector, a shuttle vector or an expression vector. Such vectors are, for example, in the form of a plasmid, a phagemid, an *agrobacterium*, a virus, a naked polynucleotide (linear or circular), or a conjugated polynucleotide. Vectors can be introduced into bacteria, especially for the purpose of propagation and expansion. The vectors are also introduced into plant tissues, cultured plant cells or plant protoplasts by a variety of standard methods known in the art, including but not limited to electroporation (From et al. (1985) *Proc. Natl. Acad. Sci. USA* 82; 5824), infection by viral vectors such as cauliflower mosaic virus (CaMV) (Hohn et al. (1982) *Molecular Biology of Plant Tumors* (Academic Press, New York, pp. 549-560; Howell U.S. Pat. No. 4,407, 956), high velocity ballistic penetration by small particles with the nucleic acid either within the matrix of small beads or particles, or on the surface (Klein et al. (1987) *Nature* 327; 70), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233;496; Fraley et al. (1983) *Proc. Natl. Acad. Sci. USA* 80;4803). Additional details regarding nucleic acid introduction methods are found in Sambrook, Berger and Ausubel, infra. The method of introducing a nucleic acid of the present invention into a host cell is not critical to the instant invention, and it is not intended that the invention be limited to any particular method for introducing exogenous genetic material into a host cell. Thus, any suitable method, e.g., including but not limited to the methods provided herein, which provides for effective introduction of a nucleic acid into a cell or protoplast can be employed and finds use with the invention.

The engineered host cells can be cultured in conventional nutrient media modified as appropriate for such activities as, for example, activating promoters or selecting transformants. These cells can optionally be cultured into transgenic plants. In addition to Sambrook, Berger and Ausubel, all infra, Plant regeneration from cultured protoplasts is described in Evans et al. (1983) "Protoplast Isolation and Culture," *Handbook of Plant Cell Cultures* 1, 124-176 (MacMillan Publishing Co., New York; Davey (1983) "Recent Developments in the Culture and Regeneration of Plant Protoplasts," *Protoplasts*, pp. 12-29, (Birkhauser, Basel); Dale (1983) "Protoplast Culture and Plant Regeneration of Cereals and Other Recalcitrant Crops," *Protoplasts* pp. 31-41, (Birkhauser, Basel); Binding (1985) "Regeneration of Plants," *Plant Protoplasts*, pp. 21-73, (CRC Press, Boca Raton, Fla.). Additional details regarding plant cell culture and regeneration include Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture; Fundamental Methods* Springer Lab Manual, Springer-Verlag (Berlin Heidelberg New York) and *Plant Molecular Biolgy* (1993) R. R. D. Croy, Ed. Bios Scientific Publishers, Oxford, U.K. ISBN 0 12 198370 6. Cell culture media in general are also set forth in Atlas and Parks (eds) *The Handbook of Microbiological Media* (1993) CRC Press, Boca Raton, Fla. Additional information for cell culture is found in available commercial literature such as the *Life Science Research Cell Culture Catalogue* (1998) from Sigma-Aldrich, Inc (St Louis, Mo.) ("Sigma-LSRCCC") and, e.g., *the Plant Culture Catalogue* and supplement (e.g., 1997 or later) also from Sigma-Aldrich, Inc (St Louis, Mo.) ("Sigma-PCCS").

The present invention also relates to the production of transgenic organisms, which may be bacteria, yeast, fungi, animals or plants, transduced with the nucleic acids of the invention (e.g., nucleic acids comprising the marker loci and/or QTL noted herein). A thorough discussion of techniques relevant to bacteria, unicellular eukaryotes and cell culture is found in references enumerated herein and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith (1979) *Gene* 8:81; Roberts et al. (1987) *Nature* 328: 731; Schneider et al. (1995) *Protein Expr. Purif.* 6435:10; Ausubel, Sambrook, Berger (all infra). A catalogue of Bacteria and Bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA*, Second Edition, Scientific American Books, N.Y. In addition, essentially any nucleic acid (and virtually any labeled nucleic acid, whether standard or nonstandard) can be custom or standard ordered from any of a variety of commercial sources, such as the Midland Certified Reagent Company (Midland, Tex.), The Great American Gene Company (Ramona, Calif.), ExpressGen Inc. (Chicago, Ill.), Operon Technologies Inc. (Alameda, Calif.) and many others.

Introducing Nucleic Acids into Plants.

Embodiments of the present invention pertain to the production of transgenic plants comprising the cloned nucleic acids, e.g., isolated ORFs and cDNAs encoding tolerance genes. Techniques for transforming plant cells with nucleic acids are widely available and can be readily adapted to the invention. In addition to Berger, Ausubel and Sambrook, all infra, useful general references for plant cell cloning, culture and regeneration include Jones (ed) (1995) *Plant Gene Transfer and Expression Protocols—Methods in Molecular Biology, Volume* 49 Humana Press Towata N.J.; Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg N.Y.) (Gamborg). A variety of cell culture media are described in Atlas and Parks (eds) *The Handbook of Microbiological Media* (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St Louis, Mo.) (Sigma-PCCS). Additional details regarding plant cell culture are found in Croy, (ed.) (1993) *Plant Molecular Biology*, Bios Scientific Publishers, Oxford, U.K.

The nucleic acid constructs of the invention, e.g., plasmids, cosmids, artificial chromosomes, DNA and RNA polynucleotides, are introduced into plant cells, either in culture or in the organs of a plant by a variety of conventional techniques. Where the sequence is expressed, the sequence is optionally combined with transcriptional and translational initiation regulatory sequences which direct the transcription or translation of the sequence from the exogenous DNA in the intended tissues of the transformed plant.

Isolated nucleic acid acids of the present invention can be introduced into plants according to any of a variety of techniques known in the art. Techniques for transforming a wide variety of higher plant species are also well known and described in widely available technical, scientific, and patent literature. See, for example, Weising et al. (1988) *Ann. Rev. Genet.* 22:421-477.

The DNA constructs of the invention, for example plasmids, phagemids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Microinjection techniques for injecting plant, e.g., cells, embryos, callus and protoplasts, are known in the art and well described in the scientific and patent literature. For example, a number of methods are described in Jones (ed) (1995) *Plant Gene Transfer and Expression Protocols—Methods in Molecular Biology, Volume* 49 Humana Press, Towata, N.J., as well as in the other references noted herein and available in the literature.

For example, the introduction of DNA constructs using polyethylene glycol precipitation is described in Paszkowski, et al., *EMBO J.* 3:2717 (1984). Electroporation techniques are described in Fromm, et al., *Proc. Natl. Acad. Sci. USA* 82:5824 (1985). Ballistic transformation techniques are described in Klein, et al., *Nature* 327:70-73 (1987). Additional details are found in Jones (1995) and Gamborg and Phillips (1995), supra, and in U.S. Pat. No. 5,990,387.

Alternatively, and in some cases preferably, *Agrobacterium* mediated transformation is employed to generate transgenic plants. *Agrobacterium*-mediated transformation techniques, including disarming and use of binary vectors, are also well described in the scientific literature. See, for example, Horsch, et al. (1984) *Science* 233:496; and Fraley et al. (1984) *Proc. Nat'l. Acad. Sci. USA* 80:4803 and recently reviewed in Hansen and Chilton (1998) *Current Topics in Microbiology* 240:22 and Das (1998) *Subcellular Biochemistry* 29: *Plant Microbe Interactions*, pp 343-363.

DNA constructs are optionally combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller (1987) In: *Genetic Engineering*, vol. 6, P W J Rigby, Ed., London, Academic Press; and Lichtenstein; C. P., and Draper (1985) In: *DNA Cloning*, Vol. II, D. M. Glover, Ed., Oxford, IRI Press; WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman et al. (1984) *Plant Cell Physiol.* 25:1353), (3) the vortexing method (see, e.g., Kindle (1990) *Proc. Natl. Acad. Sci.*, (*USA*) 87:1228.

DNA can also be introduced into plants by direct DNA transfer into pollen as described by Zhou et al. (1983) *Methods in Enzymology*, 101:433; D. Hess (1987) *Intern Rev. Cytol.* 107:367; Luo et al. (1988) *Plant Mol. Biol. Reporter* 6:165. Expression of polypeptide coding genes can be obtained by injection of the DNA into reproductive organs of a plant as described by Pena et al. (1987) *Nature* 325:274. DNA can also be injected directly into the cells of immature embryos and the desiccated embryos rehydrated as described by Neuhaus et al.(1987) *Theor. Appl. Genet.* 75:30; and Benbrook et al. (1986) in *Proceedings Bio Expo* Butterworth, Stoneham, Mass., pp. 27-54. A variety of plant viruses that can be employed as vectors are known in the art and include cauliflower mosaic virus (CaMV), geminivirus, brome mosaic virus, and tobacco mosaic virus.

Generation/Regeneration of Transgenic Plants

Transformed plant cells which are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York); Evans et al. (1983) *Protoplasts Isolation and Culture, Handbook of Plant Cell Culture* pp. 124-176, Macmillian Publishing Company, New York; and Binding (1985) *Regeneration of Plants, Plant Protoplasts* pp. 21-73, CRC Press, Boca Raton. Regeneration can also be obtained from plant callus, explants, somatic embryos (Dandekar et al. (1989) *J. Tissue Cult. Meth.* 12:145; McGranahan, et al. (1990) *Plant Cell Rep.* 8:512) organs, or parts thereof. Such regeneration techniques are described generally in Klee et al. (1987)., *Ann. Rev. of Plant Phys.* 38:467-486. Additional details are found in Payne (1992) and Jones (1995), both supra, and Weissbach and Weissbach, eds.(1988) *Methods for Plant Molecular Biology* Academic Press, Inc., San Diego, Calif. This regeneration and growth process includes the steps of selection of transformant cells and shoots, rooting the transformant shoots and growth of the plantlets in soil. These methods are adapted to the invention to produce transgenic plants bearing QTLs and other genes isolated according to the methods of the invention.

In addition, the regeneration of plants containing the polynucleotide of the present invention and introduced by *Agrobacterium* into cells of leaf explants can be achieved as described by Horsch et al. (1985) *Science* 227:1229-1231. In this procedure, transformants are grown in the presence of a selection agent and in a medium that induces the regeneration of shoots in the plant species being transformed as described by Fraley et al. (1983) *Proc. Natl. Acad. Sci.* (*U.S.A.*) 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

It is not intended that plant transformation and expression of polypeptides that provide disease resistance, as provided by the present invention, be limited to soybean species. Indeed, it is contemplated that the polypeptides that provide disease tolerance in soybean can also provide disease resistance when transformed and expressed in other agronomically and horticulturally important species. Such species include primarily dicots, e.g., of the families: Leguminosae (including pea, beans, lentil, peanut, yam bean, cowpeas, velvet beans, soybean, clover, alfalfa, lupine, vetch, lotus, sweet clover, wisteria, and sweetpea); and, Compositae (the largest family of vascular plants, including at least 1,000 genera, including important commercial crops such as sunflower).

Additionally, preferred targets for modification with the nucleic acids of the invention, as well as those specified above, plants from the genera: *Allium, Apium, Arachis, Brassica, Capsicum, Cicer, Cucumis, Curcubita, Daucus, Fagopyrum, Glycine, Helianthus, Lactuca, Lens, Lycopersicon, Medicago, Pisum, Phaseolus, Solanum, Trifolium, Vigna*, and many others.

Common crop plants which are targets of the present invention include soybean, sunflower, canola, peas, beans, lentils, peanuts, yam beans, cowpeas, velvet beans, clover, alfalfa, lupine, vetch, sweet clover, sweetpea, field pea, fava bean, broccoli, brussel sprouts, cabbage, cauliflower, kale, kohlrabi, celery, lettuce, carrot, onion, pepper, potato, eggplant and tomato.

In construction of recombinant expression cassettes of the invention, which include, for example, helper plasmids comprising virulence functions, and plasmids or viruses comprising exogenous DNA sequences such as structural genes, a plant promoter fragment is optionally employed which directs expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds or flowers.

Any of a number of promoters which direct transcription in plant cells can be suitable. The promoter can be either constitutive or inducible. In addition to the promoters noted above, promoters of bacterial origin that operate in plants include the octopine synthase promoter, the nopaline synthase promoter and other promoters derived from native Ti plasmids. See, Herrara-Estrella et al. (1983), *Nature,* 303: 209. Viral promoters include the 35S and 19S RNA promoters of cauliflower mosaic virus. See, Odell et al. (1985) *Nature,* 313:810. Other plant promoters include Kunitz trypsin inhibitor promoter (KTI), SCP1, SUP, UCD3, the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) *EMBO J.* 7:3315. Many other promoters are in current use and can be coupled to an exogenous DNA sequence to direct expression of the nucleic acid.

If expression of a polypeptide from a cDNA is desired, a polyadenylation region at the 3'-end of the coding region is typically included. The polyadenylation region can be derived from the natural gene, from a variety of other plant genes, or from, e.g., T-DNA.

The vector comprising the sequences (e.g., promoters or coding regions) from genes encoding expression products and transgenes of the invention will typically include a nucleic acid subsequence, a marker gene which confers a selectable, or alternatively, a screenable, phenotype on plant cells. For example, the marker can encode biocide tolerance, particularly antibiotic tolerance, such as tolerance to kanamycin, G418, bleomycin, hygromycin, or herbicide tolerance, such as tolerance to chlorosluforon, or phosphinothricin (the active ingredient in the herbicides bialaphos or Basta). See, e.g., Padgette et al. (1996) In: *Herbicide-Resistant Crops* (Duke, ed.), pp 53-84, CRC Lewis Publishers, Boca Raton ("Padgette, 1996"). For example, crop selectivity to specific herbicides can be conferred by engineering genes into crops that encode appropriate herbicide metabolizing enzymes from other organisms, such as microbes. See, Vasil (1996) In: *Herbicide-Resistant Crops* (Duke, ed.), pp 85-91, CRC Lewis Publishers, Boca Raton) ("Vasil", 1996).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic or introgressed plants expressing a polynucleotide of the present invention can be screened for transmission of the nucleic acid of the present invention by, for example, standard nucleic acid detection methods or by immunoblot protocols. Expression at the RNA level can be determined to identify and quantitate expression-positive plants. Standard techniques for RNA analysis can be employed and include RT-PCR amplification assays using oligonucleotide primers designed to amplify only heterologous or introgressed RNA templates and solution hybridization assays using marker or linked QTL specific probes. Plants can also be analyzed for protein expression, e.g., by Western immunoblot analysis using antibodies that recognize the encoded polypeptides. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment of the invention is a transgenic plant that is homozygous for the added heterologous nucleic acid; e.g., a transgenic plant that contains two added nucleic acid sequence copies, e.g., a gene at the same locus on each chromosome of a homologous chromosome pair. A homozygous transgenic plant can be obtained by sexually mating (self-fertilizing) a heterozygous transgenic plant that contains a single added heterologous nucleic acid, germinating some of the seed produced and analyzing the resulting plants produced for altered expression of a polynucleotide of the present invention relative to a control plant (e.g., a native, non-transgenic plant). Back-crossing to a parental plant and out-crossing with a non-transgenic plant can be used to introgress the heterologous nucleic acid into a selected background (e.g., an elite or exotic soybean line).

Methods for Identifying *Sclerotinia*-Tolerant Soybean Plants

Experienced plant breeders can recognize tolerant soybean plants in the field, and can select the tolerant individuals or populations for breeding purposes or for propagation. In this context, the plant breeder recognizes "tolerant" and "non-tolerant," or "susceptible" soybean plants.

Such plant breeding practitioners will appreciate that plant tolerance is a phenotypic spectrum consisting of extremes in tolerance, susceptibility and a continuum of intermediate tolerance phenotypes. Tolerance also varies due to environmental effects and the severity of pathogen infection. Evaluation of phenotypes using reproducible assays and tolerance scoring methods are of value to scientists who seek to identify genetic loci that impart tolerance, conduct marker assisted selection for tolerant population, and for introgression techniques to breed a tolerance trait into an elite soybean line, for example.

In contrast to fortuitous field observations that classify plants as either "tolerant" or "susceptible," various systems are known for scoring the degree of plant tolerance or susceptibility. These techniques can be applied to different fields at different times, and provide approximate tolerance scores that can be used to characterize a given strain regardless of growth conditions or location. Briefly, the degree of *Sclerotinia* stem rot tolerance in a particular test plant or test stand can be quantitated by using a system to score the severity of the disease in each soybean plant or stand by using a co-propagated collection of reference strains with known tolerance ratings to serve as a tolerance scoring guide.

The rating system used to obtain a *Sclerotinia sclerotiorum* tolerance score for a soybean line reflects the unpredictability of this disease's occurrence and fluctuations in severity in soybean production fields. To date, no soybean line having complete immunity to *Sclerotinia sclerotiorum* infection under all environmental conditions has been identified. However, experience has shown that, when the disease occurs, some soybean lines are repeatedly (heritably) more tolerant than others. Therefore, the key to an effective field screening system is establishing a series of susceptible and tolerant check reference lines that span the known spectrum of pathological response to *Sclerotinia* stem rot infection (i.e., most susceptible to most tolerant), and assigning each of the reference strains a numerical score. A disease tolerance score of a test plant or test check is assigned by comparing the pathology of the test check with the pathologies of the reference checks with known tolerance scores to find a closest match.

Generally, a score of two (2) indicates the most susceptible strains, and a score of seven (7) is assigned to the most tolerant lines. Although score of one (1) is given occasionally, soybean strains with such extremely high susceptibility are generally not used or maintained in future tests. Tolerance scores of eight (8) and nine (9) are generally not observed, and are reserved for even higher tolerance plants that may be identified in the future. Soybean lines that can be used as reference checks to define *Sclerotinia* stem rot tolerance phenotypes are provided in the table below. These lines display the phenotypic range of *Sclerotinia* stem rot phenotypes, and these varieties maintain their relative degrees of tolerance in multiple field tests. In any given field test, all or some (e.g., one from each tolerance score group) of the reference lines are planted in fields adjacent to soybean lines that are being evaluated. It is not intended that the list of possible reference lines that find use with the invention be limited to those lines listed in the table below. Any suitable variety that has been previously scored for *Sclerotinia* stem rot tolerance and maintains its relative tolerance compared to other reference lines in multiple field tests can be used as a reference line. See, for example, the lines listed below that can be used as reference lines:

| Pioneer ® Hi-Bred International Commercial Soybean Varieties | *Sclerotinia* stem rot tolerance score |
|---|---|
| 91M11 | 2 |
| 92B95 | 2 |
| 93M60 | 2 |
| 90B11 | 3 |
| 92B05 | 3 |
| 92M32 | 3 |
| 93B36 | 3 |
| 90M60 | 4 |
| 91M40 | 4 |
| 92M70 | 4 |
| 90B74 | 5 |
| 91M50 | 5 |
| 92M71 | 5 |
| 93B68 | 5 |
| 91M51 | 6 |
| 92M30 | 6 |
| 92M80 | 6 |
| 93M11 | 6 |
| 90B73 | 7 |
| S1990** | 7 |

**a Northrup King (NK ®) culitvar

Typically, scores for the reference varieties such as those listed above are obtained from a combination of specific tests in fields known to have a history of poor yield due to recurring *Sclerotinia sclerotiorum* infection ("field screens") and fortuitous natural incidence of *Sclerotinia sclerotiorum* in other field tests. At the end of each year, a team of breeders reviews the tolerance data and assigns or adjusts the tolerance score of each soybean variety based on the available data from the current season's and previous seasons' tests, typically averaged from many locations of crop plantings.

When plants are studied in a fortuitous natural field setting, if there is no *Sclerotinia* stem rot disease present, the rating system above can not be used, because the existence of *Sclerotinia sclerotiorum* infection can not be ascertained. However, if some number of plants demonstrate *Sclerotinia* stem rot symptoms, the field can be assumed to contain *Sclerotinia sclerotiorum*, and the entire stand can be scored as described above.

The *Sclerotinia* stem rot scoring of soybean stands can occur at any time during the growth season after the R2 developmental stage. For example, plots can be scored in mid July (depending on geographic latitude), so that the results can be used in making crossing decisions. Alternatively, soybean plots can be scored in the late season, which generally yields more precise data.

It will be appreciated that any tolerance scoring system has a subjective component, and furthermore, there may be variability between practitioners as to how the individual plants and the entire stand as a whole are scored. However, while there can be a certain amount of subjectivity to classifying the severity of infection symptoms, the comparisons between experimental and reference stands or assignment of a particular tolerance score as noted above is well within the skill level of a practitioner of average skill in the art. Measurements can also be averaged across multiple scorers, multiple planting dates and multiple planting locations in order to reduce variation in the tolerance scoring.

In addition to the field tests described above, methods are known in the art for assaying the tolerance of a soybean plant to *Sclerotinia* stem rot using controlled artificial infections (e.g., using artificial *Sclerotinia sclerotiorum* infections in a nursery or greenhouse; see, for example, the methods provided in EXAMPLES 4 and 5). When the assay is conducted in controlled conditions, tested plants can be inoculated with a suitable strain of *Sclerotinia sclerotiorum* that is known to produce disease. The plants can be scored for *Sclerotinia* stem rot severity at any stage of maturity, including any time before plant maturity; in one example, when an artificial stem lesion assay is used (see, EXAMPLE 4), plants are inoculated between the V3 and V4 stages, and are scored for infection severity 6-8 days following fungal inoculation. When an artificial system is used to assay soybean plant tolerance to *Sclerotinia* stem rot (such as the stem lesion assay described in EXAMPLE 4), a tolerance score can be assigned to a test plant or test strain by comparing the severity of infection in the test strain to the infections in a collection of reference strains (e.g., the reference strains taught herein) that are cultured and analyzed in parallel to the experimental strain. Alternatively, the plants in the stem lesion assay can be scored on an absolute scale where a score of nine (9) indicates complete tolerance and immunity (absolute tolerance) with no signs of infection, and one (1) where the plant is highly susceptible to infection and the stem of the plant shows girdling and extensive lesions. Intermediate scores can be defined by the size and severity of stem lesioning.

In assessing linkage of markers to tolerance, either quantitative or qualitative approaches can be used. For example, a single tolerance score for each line (e.g., a tolerance score from 1 to 9) can be assessed for linkage. This approach is quantitative and uses the scores from lines that have both marker data and *Sclerotinia* stem rot tolerance scores. In an alternative approach, an "intergroup" comparison of tolerant versus susceptible lines is used. In this approach, those soybean lines that are considered to be representative of either the tolerant or susceptible classes are used for assessing linkage. A list of tolerant lines is constructed, e.g., strains having a tolerance score of 6 or greater are considered "tolerant." Similarly, soybean lines with scores of four or less are considered susceptible. Only lines that can be reliably placed into the two groups are used. Once a line is included in the "tolerant" or "susceptible" group, it is treated as an equal in that group, i.e., the actual quantitative ratings are not used.

The method described above can also easily be adapted to test whether plant tolerance is race-specific or non-race specific. For example, a candidate soybean strain can be tested for tolerance to a variety of previously identified *Sclerotinia* races, where the virulent races have been shown to infect formerly resistant soybean plants. In this case, a plurality of *Sclerotinia* races are used to inoculate the plant cultivars assessed in the assay. If the soybean plants are tolerant to all the *Sclerotinia* races tested, or to a subset of the races tested, the soybean strain can be considered to have non-race specific tolerance, or partially non-race specific tolerance.

Automated Detection/Correlation Systems of the Invention

In some embodiments, the present invention includes an automated system for detecting markers of the invention and/or correlating the markers with a desired phenotype (e.g., tolerance). Thus, a typical system can include a set of marker probes or primers configured to detect at least one favorable allele of one or more marker locus associated with tolerance or improved tolerance to *Sclerotinia* infection. These probes or primers are configured to detect the marker alleles noted in the tables and examples herein, e.g., using any available allele detection format, e.g., solid or liquid phase array based detection, microfluidic-based sample detection, etc.

For example, in one embodiment, the marker locus is SAG1032, SATT597, SCT_026, SATT391, S60817-TB, S60239-TB, P10646A-1, P7659A-2, SATT570, SATT356, S60222-TB, SATT166, SATT448 and SAG1048, or any combination thereof, as well as any of the chromosome intervals:

(i) SAG1032 and SCT_026 (LG-B1);
(ii) S60239-TB and SATT356 (LG-G);
(iii) SATT166 and SATT448 (LG-L); and
(iv) SATT463 and SATT175 (LG-M), and the probe set is configured to detect the locus.

The typical system includes a detector that is configured to detect one or more signal outputs from the set of marker probes or primers, or amplicon thereof, thereby identifying the presence or absence of the allele. A wide variety of signal detection apparatus are available, including photo multiplier tubes, spectrophotometers, CCD arrays, arrays and array scanners, scanning detectors, phototubes and photodiodes, microscope stations, galvo-scanns, microfluidic nucleic acid amplification detection appliances and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector embodiments include light (e.g., fluorescence) detectors or radioactivity detectors. For example, detection of a light emission (e.g., a fluorescence emission) or other probe label is indicative of the presence or absence of a marker allele. Fluorescent detection is especially preferred and is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele.

The detector(s) optionally monitors one or a plurality of signals from an amplification reaction. For example, the detector can monitor optical signals which correspond to "real time" amplification assay results.

System instructions that correlate the presence or absence of the favorable allele with the predicted tolerance are also a feature of the invention. For example, the instructions can include at least one look-up table that includes a correlation between the presence or absence of the favorable alleles and the predicted tolerance or improved tolerance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical embodiment, the system instructions include at least one look-up table that includes a correlation between the presence or absence of the favorable alleles and predicted tolerance or improved tolerance. The instructions also typically include instructions providing a user interface with the system, e.g., to permit a user to view results of a sample analysis and to input parameters into the system.

The system typically includes components for storing or transmitting computer readable data representing or designating the alleles detected by the methods of the present invention, e.g., in an automated system. The computer readable media can include cache, main, and storage memory and/or other electronic data storage components (hard drives, floppy drives, storage drives, etc.) for storage of computer code. Data representing alleles detected by the method of the present invention can also be electronically, optically, magnetically o transmitted in a computer data signal embodied in a transmission medium over a network such as an intranet or internet or combinations thereof. The system can also or alternatively transmit data via wireless, IR, or other available transmission alternatives.

During operation, the system typically comprises a sample that is to be analyzed, such as a plant tissue, or material isolated from the tissue such as genomic DNA, amplified genomic DNA, cDNA, amplified cDNA, RNA, amplified RNA, or the like.

The phrase "allele detection/correlation system" in the context of this invention refers to a system in which data entering a computer corresponds to physical objects or processes external to the computer, e.g., a marker allele, and a process that, within a computer, causes a physical transformation of the input signals to different output signals. In other words, the input data, e.g., amplification of a particular marker allele is transformed to output data, e.g., the identification of the allelic form of a chromosome segment. The process within the computer is a set of instructions, or "program," by which positive amplification or hybridization signals are recognized by the integrated system and attributed to individual samples as a genotype. Additional programs correlate the identity of individual samples with phenotypic values or marker alleles, e.g., statistical methods. In addition there are numerous e.g., C/C++ programs for computing, Delphi and/or Java programs for GUI interfaces, and productivity tools (e.g., Microsoft Excel and/or SigmaPlot) for charting or creating look up tables of relevant allele-trait correlations. Other useful software tools in the context of the integrated systems of the invention include statistical packages such as SAS, Genstat, Matlab, Mathematica, and S-Plus and genetic modeling packages such as QU-GENE. Furthermore, additional programming languages such as visual basic are also suitably employed in the integrated systems of the invention.

For example, tolerance marker allele values assigned to a population of progeny descending from crosses between elite lines are recorded in a computer readable medium, thereby establishing a database corresponding tolerance alleles with unique identifiers for members of the population of progeny. Any file or folder, whether custom-made or commercially available (e.g., from Oracle or Sybase) suitable for recording data in a computer readable medium is acceptable as a database in the context of the present invention. Data regarding genotype for one or more molecular markers, e.g., ASH, SSR, RFLP, RAPD, AFLP, SNP, isozyme markers or other markers as described herein, are similarly recorded in a computer accessible database. Optionally, marker data is obtained using an integrated system that automates one or more aspects of the assay (or assays) used to determine marker(s) genotype. In such a system, input data corresponding to genotypes for molecular markers are relayed from a detector, e.g., an array, a scanner, a CCD, or other detection device directly to files in a computer readable medium accessible to the central processing unit. A set of system instructions (typically embodied in one or more programs) encoding the correlations between tolerance and the alleles of the invention is then executed by the computational device to identify correlations between marker alleles and predicted trait phenotypes.

Typically, the system also includes a user input device, such as a keyboard, a mouse, a touchscreen, or the like, for, e.g., selecting files, retrieving data, reviewing tables of marker information, etc., and an output device (e.g., a monitor, a printer, etc.) for viewing or recovering the product of the statistical analysis.

Thus, in one aspect, the invention provides an integrated system comprising a computer or computer readable medium comprising set of files and/or a database with at least one data set that corresponds to the marker alleles herein. The system also includes a user interface allowing a user to selectively view one or more of these databases. In addition, standard text manipulation software such as word processing software (e.g., Microsoft Word™ or Corel WordPerfect™) and database or spreadsheet software (e.g., spreadsheet software such as Microsoft Excel™, Corel Quattro Pro™, or database programs such as Microsoft Access™ or Paradox™) can be used in conjunction with a user interface (e.g., a GUI in a standard operating system such as a Windows, Macintosh, Unix or Linux system) to manipulate strings of characters corresponding to the alleles or other features of the database.

The systems optionally include components for sample manipulation, e.g., incorporating robotic devices. For example, a robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system. Many such automated robotic fluid handling systems are commercially available. For example, a variety of automated systems are available from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). As an alternative to conventional robotics, microfluidic systems for performing fluid handling and detection are now widely available, e.g., from Caliper Technologies Corp. (Hopkinton, Mass.) and Agilent technologies (Palo Alto, Calif.).

Systems for molecular marker analysis of the present invention can, thus, include a digital computer with one or more of high-throughput liquid control software, image analysis software for analyzing data from marker labels, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to markers on a solid support operably linked to the digital computer. The image scanner interfaces with the image analysis software to provide a measurement of, e.g., nucleic acid probe label intensity upon hybridization to an arrayed sample nucleic acid population (e.g., comprising one or more markers), where the probe label intensity measurement is interpreted by the data interpretation software to show whether, and to what degree, the labeled probe hybridizes to a marker nucleic acid (e.g., an amplified marker allele). The data so derived is then correlated with sample identity, to determine the identity of a plant with a particular genotype(s) for particular markers or alleles, e.g., to facilitate marker assisted selection of soybean plants with favorable allelic forms of chromosome segments involved in agronomic performance (e.g., tolerance or improved tolerance).

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image, e.g., using PC (Intel x86 or pentium chip-compatible DOS™, OS2™ WINDOWS™, WINDOWS NT™ or WINDOWS95™ based machines), MACINTOSH™, LINUX, or UNIX based (e.g., SUN™ work station) computers.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Example 1

Intergroup Allele Frequency Distribution Analysis

Two independent allele frequency distribution analyses were undertaken to identify soybean genetic marker loci associated with tolerance to Sclerotinia infection. By identifying such genetic markers, marker assisted selection (MAS) can be used to improve the efficiency of breeding for improved tolerance of soybean to Sclerotinia infection.

Soybean Lines and Tolerance Scoring

The plant varieties used in the analysis were from diverse sources, including elite germplasm, commercially released cultivars and other public lines representing a broad range of germplasm. The lines used in the study had a broad maturity range varying from group 0 to group 6.

Two groups of soybean lines were assembled for each analysis based on their phenotypic extremes in tolerance to Sclerotinia white mold infestation, where the plants were sorted into either highly susceptible or highly tolerant varieties. The classifications of tolerant and susceptible were based solely on observations of fortuitous, naturally occurring disease incidence in field tests over several years and greenhouse observations. The degree of plant tolerance to Sclerotinia infection varied widely, as measured using a scale from one (highly susceptible) to nine (highly tolerant). Generally, a score of two (2) indicated the most susceptible strains, and a score of seven (7) was assigned to the most tolerant lines. A score of one (1) was generally not used, as soybean strains with such extremely high susceptibility were not typically propagated. Tolerance scores of eight (8) and nine (9) were reserved for tolerance levels that are very rare and generally not observed in existing germplasm. If no disease was present in a field, no tolerance scoring was done. However, if a disease did occur in a specific field location, all of the lines in that location were scored. Scores for test strains accumulated over multiple locations and multiple years, and an averaged (e.g., consensus) score was ultimately assigned to each line.

Individual fields showing *Sclerotinia* stem rot were monitored for disease symptoms during the vegetative stages but typically appear in the early to late reproductive stages. Data collection was typically done in three or four successive scorings about seven days apart. Scorings continued until worsening symptoms can no longer be quantified or until the symptoms are confounded by other factors such as other diseases, insect pressure, severe weather, or advancing maturity.

In assessing association of markers to tolerance, a qualitative "intergroup allele frequency distribution" comparison approach was used. Using this approach, those soybean lines that were considered to be representative of either the tolerant or susceptible classes were used for assessing association. A list of tolerant lines was constructed, where strains having a tolerance score of 6 or greater were considered "tolerant." Similarly, soybean lines with scores of four or less were collectively considered susceptible. Only lines that could be reliably placed into the two groups were used. Once a line is included in the "tolerant" or "susceptible" group, it was treated as an equal in that group, i.e., the actual quantitative ratings were not used.

In the study, 39 soybean lines were identified that were considered tolerant in the phenotypic spectrum; these plants formed the "TOLERANT" group. Also, 33 soybean lines were identified that were judged to be susceptible to *Sclerotinia* stem rot; these strains formed the "SUSCEPTIBLE" group.

Soybean Genotyping

Each of the tolerant and susceptible lines was genotyped with SSR and SNP markers that span the soybean genome using techniques well known in the art. The genotyping protocol consisted of collecting young leaf tissue from eight individuals from each tolerant and resistant soybean strain, pooling (i.e., bulking) the leaf tissue from the eight individuals, and isolating genomic DNA from the pooled tissue. The soybean genomic DNA was extracted by the CTAB method, as described in Maroof et al., (1984) Proc. Natl. Acad. Sci. (USA) 81:8014-8018.

The isolated genomic DNA was then used in PCR reactions using amplification primers specific for a large number of markers that covered all chromosomes in the soybean genome. The length of the PCR amplicon or amplicons from each PCR reaction were characterized. The length of the amplicons generated in the PCR reactions were compared to known allele definitions for the various markers (see, e.g., FIG. 4), and allele designations were assigned. SNP-type markers were genotyped using an ASH protocol.

Intergroup Allele Frequency Analysis

An "Intergroup Allele Frequency Distribution" analysis was conducted using GeneFlow™ version 7.0 software. An intergroup allele frequency distribution analysis provides a method for finding non-random distributions of alleles between two phenotypic groups.

During processing, a contingency table of allele frequencies is constructed and from this a G-statistic and probability are calculated (the G statistic is adjusted by using the William's correction factor). The probability value is adjusted to take into account the fact that multiple tests are being done (thus, there is some expected rate of false positives). The adjusted probability is proportional to the probability that the observed allele distribution differences between the two classes would occur by chance alone. The lower that probability value, the greater the likelihood that the *Sclerotinia* infection phenotype and the marker will co-segregate. A more complete discussion of the derivation of the probability values can be found in the GeneFlow™ version 7.0 software documentation. See, also, Sokal and Rolf (1981), *Biometry:*

*The Principles and Practices of Statistics in Biological Research,* 2nd ed., San Francisco, W. H. Freeman and Co.

The underlying logic is that markers with significantly different allele distributions between the tolerant and susceptible groups (i.e., non random distributions) might be associated with the trait and can be used to separate them for purposes of marker assisted selection of soybean lines with previously uncharacterized tolerance or susceptibility to *Sclerotinia* stem rot. The present analysis examined one marker locus at a time and determined if the allele distribution within the tolerant group is significantly different from the allele distribution within the susceptible group. A statistically different allele distribution is an indication that the marker is linked to a locus that is associated with reaction to *Sclerotinia* stem rot. In this analysis, unadjusted probabilities less than one are considered significant (the marker and the phenotype show linkage disequilibrium), and adjusted probabilities less than approximately 0.05 are considered highly significant. Allele classes represented by less than 5 observations across both groups were not included in the statistical analysis. In this analysis, 385 marker loci had enough observations for analysis.

This analysis compares the plants' phenotypic score with the genotypes at the various loci. This type of intergroup analysis neither generates nor requires any map data. Subsequently, map data (for example, a composite soybean genetic map) is relevant in that multiple significant markers that are also genetically linked can be considered as collaborating evidence that a given chromosomal region is associated with the trait of interest.

Results

FIG. 1 provides a table listing the soybean markers that demonstrated linkage disequilibrium with the *Sclerotinia* tolerance/susceptibility phenotype. Also indicated in that figure are the chromosomes on which the markers are located and their approximate map position relative to other known markers, given in cM, with position zero being the first (most distal) marker known at the beginning of the chromosome. These map positions are not absolute, and represent an estimate of map position. The statistical probabilities that the marker allele and tolerance phenotype are segregating independently are reflected in the adjusted probability values.

FIG. 2 provides the PCR primer sequences that were used to genotype these marker loci. FIG. 2 also provides the pigtail sequence used on the 5' end of the right SSR-marker primers and the number of nucleotides in the repeating element in the SSR. The observed alleles that are known to occur for these marker loci are provided in the allele dictionary in FIG. 4.

Out of 385 loci studied, simple sequence repeat (SSR) or single nucleotide polymorphism (SNP) loci having adjusted probability values for independent assortment with *Sclerotinia* stem rot tolerance of less than approximately 0.05 were identified (see, FIG. 1). The statistical probabilities that the marker allele and tolerance phenotype are segregating independently are reflected in the Adjusted Probability values.

In addition, the marker SAG1048 showed a pattern of non-random allele distribution when viewing the genotypes of tolerant and susceptible lines (see, FIG. 5). For example, this marker generally showed allele 3 in the disease tolerant plants, while the presence of allele 2 generally correlated with disease susceptible plants for that same marker.

The non-random distribution of alleles between the tolerant and susceptible plant groups at the various marker loci in FIG. 1 is good evidence that a QTL influencing *Sclerotinia* stem rot tolerance is linked to these marker loci.

Flower Color Determination and Disease Tolerance

An intergroup analysis for flower color determination was also undertaken using a similar protocol and using Gene-Flow™ software. Observing several hundred soybean lines from diverse germplasm, this analysis identified the EST-SSR marker S60817-TB on linkage group F as a determinant for flower color. Alleles 2 and 4 at this maker locus result in purple flower color, while allele 3 gives white flower color.

Interestingly, it was observed that purple flower lines often have greater defense to *Sclerotinia* white mold; there is often a correlation between the most disease-tolerant lines across time and purple flower. Genotyping revealed that these most tolerant purple flower lines most frequently carry allele 2 of the S60817-TB marker. It was also determined that the most disease-susceptible lines over time almost exclusively carry allele 4 (for purple flower color) or allele 3 (for white flower color).

White mold tolerance is controlled from many different physiological and architectural mechanisms. However, an understanding of the molecular or physiological mechanisms involved in *Sclerotinia* white mold tolerance is not required to make or use the invention. It is possible that purple flower color is a result of anthocyanin production in the flower. Anthocyanins are also known to be involved in the disease tolerance mechanisms. It was also observed that purple flowers stay viable longer in the field. Given that the *Sclerotinia* ascospores from white mold infect the plant through dead and dying flower tissue, any type of factor that increases flower health and defense may reduce infection.

The S60817-TB marker was also identified as a marker correlating with white mold tolerance using marker regression analysis with the 9163/92B05 white mold tolerance mapping population from field white mold scoring (see Example 3). This marker (i.e., the QTL represented by this marker) was not detected in QTL interval mapping (only in the single marker regression). Both lines 9163 and 92B05 are purple flower color. Line 9163 carries allele 2, and line 92B05 carries allele 4. Line 9163 has good tolerance to white mold, while 92B05 is very susceptible to white mold. RIL's with better white mold tolerance carried allele 2 at S60817-TB.

Discussion

There are a number of ways to use the information provided in this analysis for the development of improved soybean varieties. One application is to use the associated markers (or more based on a higher probability cutoff value) as candidates for mapping QTL in specific populations that are segregating for plants having tolerance to *Sclerotinia* infection. In this application, one proceeds with conventional QTL mapping in a segregating population, but focusing on the markers that are associated with *Sclerotinia* infection tolerance, instead of using markers that span the entire genome. This makes mapping efforts more cost-effective by dramatically reducing lab resources committed to the project. For example, instead of screening segregating populations with a large set of markers that spans the entire genome, one would screen with only those few markers that met some statistical cutoff in the intergroup allele association study. This will not only reduce the cost of mapping but will also eliminate false leads that will undoubtedly occur with a large set of markers. In any given cross, it is likely that only a small subset of the associated markers will actually be correlated with tolerance to *Sclerotinia* infection. Once the few relevant markers are identified in any tolerant parent, future marker assisted selection (MAS) efforts can focus on only those markers that are important for that source of tolerance. By pre-selecting lines that have the allele associated with tolerance via MAS, one can eliminate the undesirable susceptible lines and concentrate the expensive field testing resources on lines that have a higher probability of being tolerant to *Sclerotinia* infection.

Example 2

Association Mapping Analysis

An association mapping strategy was undertaken to identify soybean genetic markers associated with tolerance to *Sclerotinia* infection, which is the causative agent of soybean white mold (also termed stem rot). The study was completed twice, generating two independent data sets. By identifying such genetic markers, marker assisted selection (MAS) can be used to improve the efficiency of breeding for improved tolerance of soybean to *Sclerotinia* infection. Association mapping is known in the art, and is described in various sources, e.g., Jorde (2000), Genome Res., 10:1435-1444; Remington et al. (2001), "Structure of linkage disequilibrium and phenotype associations in the maize genome," Proc Natl Acad Sci USA 98:11479-11484; and Weiss and Clark (2002), Trends in Genetics 18:19-24.

Association Mapping

Understanding the extent and patterns of linkage disequilibrium (LD) in the genome is a prerequisite for developing efficient association approaches to identify and map quantitative trait loci (QTL). Linkage disequilibrium (LD) refers to the non-random association of alleles in a collection of individuals. When LD is observed among alleles at linked loci, it is measured as LD decay across a specific region of a chromosome. The extent of the LD is a reflection of the recombinational history of that region. The average rate of LD decay in a genome can help predict the number and density of markers that are required to undertake a genome-wide association study and provides an estimate of the resolution that can be expected.

Association or LD mapping aims to identify significant genotype-phenotype associations. It has been exploited as a powerful tool for fine mapping in outcrossing species such as humans (Corder et al. (1994) "Protective effect of apolipoprotein-E type-2 allele for late-onset Alzheimer-disease," Nat Genet 7:180-184; Hastbacka et al., (1992) "Linkage disequilibrium mapping in isolated founder populations: diastrophic dysplasia in Finland," Nat Genet 2:204-211; Kerem et al., (1989) "Identification of the cystic fibrosis gene: genetic analysis," Science 245:1073-1080) and maize (Remington et al., (2001) "Structure of linkage disequilibrium and phenotype associations in the maize genome," Proc Natl Acad Sci USA 98:11479-11484; Thornsberry et al. (2001) "Dwarf8 polymorphisms associate with variation in flowering time," Nat Genet 28:286-289; reviewed by Flint-Garcia et al. (2003) "Structure of linkage disequilibrium in plants," Annu Rev Plant Biol., 54:357-374), where recombination among heterozygotes is frequent and results in a rapid decay of LD. In inbreeding species where recombination among homozygous genotypes is not genetically detectable, the extent of LD is greater (i.e., larger blocks of linked markers are inherited together) and this dramatically lowers the resolution of association mapping (Wall and Pritchard (2003) "Haplotype blocks and linkage disequilibrium in the human genome," Nat Rev Genet 4:587-597).

The recombinational and mutational history of a population is a function of the mating habit, as well as the effective size and age of a population. Large population sizes offer enhanced possibilities for detecting recombination, while older populations are generally associated with higher levels of polymorphism, both of which contribute to observably accelerated rates of LD decay. On the other hand, smaller effective population sizes, i.e., those that have experienced a recent genetic bottleneck, tend to show a slower rate of LD decay, resulting in more extensive haplotype conservation (Flint-Garcia et al. (2003) "Structure of linkage disequilibrium in plants," Annu Rev Plant Biol., 54:357-374).

Elite breeding lines provide a valuable starting point for association analyses. Association analyses use quantitative phenotypic scores (e.g., disease tolerance rated from one to nine for each soybean line) in the analysis (as opposed to looking only at tolerant versus resistant allele frequency distributions in intergroup allele distribution types of analysis). The availability of detailed phenotypic performance data collected by breeding programs over multiple years and environments for a large number of elite lines provides a valuable dataset for genetic marker association mapping analyses. This paves the way for a seamless integration between research and application and takes advantage of historically accumulated data sets. However, an understanding of the relationship between polymorphism and recombination is useful in developing appropriate strategies for efficiently extracting maximum information from these resources.

This type of association analysis neither generates nor requires any map data, but rather, is independent of map position. This analysis compares the plants' phenotypic score with the genotypes at the various loci. Subsequently, any suitable soybean map (for example, a composite map) can optionally be used to help observe distribution of the identified QTL markers and/or QTL marker clustering using previously determined map locations of the markers.

Soybean Lines and Phenotypic Scoring

Soybean lines were phenotypically scored based on their degree of tolerance to *Sclerotinia* infection (in contrast to simple categorization of "tolerant" or "susceptible"). The plant varieties used in the analysis were from diverse sources, including elite germplasm, commercially released cultivars and other public varieties. The collections comprised 205 soybean lines, or alternatively, 177 lines in the two analyses. The lines used in the study had a broad maturity range varying from group 0 to group 6, but typically lines at R3 (2 years from commercial product) or above were used.

The tolerance scoring was based solely on observations in fortuitous, naturally occurring fields displaying disease incidence in multienvironmental field tests over several years. The degree of plant tolerance to *Sclerotinia* infestation varied widely, as measured using a scale from one (1; highly susceptible) to nine (9; highly tolerant). Generally, a score of two (2) indicated the most susceptible strains, and a score of seven (8) was assigned to the most tolerant lines. A score of one (1) was generally not used, as soybean strains with such extremely high susceptibility were not typically propagated. A tolerance score of nine (9) was reserved for tolerance levels that are very rare and generally not observed in existing germplasm. If no disease was present in a field, no tolerance scoring was done. However, if disease did occur in a specific field location, all of the lines in that location were scored. Tolerance scores for the reference strains accumulated over multiple locations and years, and an averaged (e.g., consensus) score was ultimately assigned to each line. Tolerance scores for the 205 variety collection or the 177 variety collection were collected over single grow seasons.

Individual fields showing *Sclerotinia* infestation were monitored for disease symptoms during the vegetative stages, but typically appear in the early or late reproductive stages. Data collection was typically done in four scorings about seven days apart. Scorings continued until worsening symptoms can no longer be quantified or until the symptoms are confounded by other factors such as other diseases, insect pressure, severe weather, or advancing maturity.

In assessing the linkage of markers to tolerance, a quantitative approach was used, where a tolerance score for each soybean line was assessed and incorporated into the association mapping statistical analysis.

Soybean Genotyping

The independent populations of either 205 or 177 soybean lines that were scored for disease tolerance were then genotyped. The 205 member population was genotyped using 287 SSR and ASH markers. The 177 member population was genotyped using 374 SSR and ASH markers. These SSR and SNP markers collectively spanned each chromosome in the plant genome. The genotyping protocol consisted of collecting young leaf tissue from eight individuals from each soybean strain, pooling (i.e., bulking) the leaf tissue from the eight individuals, and isolating genomic DNA from the pooled tissue. The soybean genomic DNA was extracted by the CTAB method, as described in Maroof et al., (1984) Proc. Natl. Acad. Sci. (USA) 81:8014-8018.

The isolated genomic DNA was then used in PCR reactions using amplification primers specific for a large number of markers that covered all chromosomes in the soybean genome. The length of the PCR amplicon or amplicons from each PCR reaction were characterized. SNP-type markers were genotyped using an ASH protocol. The length of the amplicons generated in the PCR reactions were compared to known allele definitions for the various markers (see FIG. 4), and allele designations for each tested marker were assigned.

Statistical Methods

Monomorphic loci are considered uninformative and thus are eliminated from LD analyses. The monomorphic loci are defined as those whose gene diversity (1--

$$\sum_{i=1}^{n} pi,$$

where $p_i$ is $i^{th}$ allele frequency in the population of study) is less than 0.10. Since rare alleles (frequency <0.05) tend to cause large variances for the estimates of $r^2$, they were treated as missing data and pooled together. Marker screening and partitioning are conducted using PowerMarker software (version 2.72), which was developed by Jack Liu.

The rate of LD decay with genetic distance (cM) was calculated for pairs of markers on the same chromosome and was evaluated using linear regression in which the genetic distances were transformed by taking $\log_{10}$, as described by McRae et al. (2002). Population structure was evaluated using Pritchard's model-based method (Pritchard et al. 2000) and the software, STRUCTURE (version 2.0). This version of the program controls for linked markers and correlated allelic frequencies (Falush et al. (2003) "Inference of population structure using multilocus genotype data: linked loci and correlated allele frequencies," Genetics 164: 1567-1587). It detects population structure in structured or admixed populations. This method is more appropriate than conventionally used genetic distance-based method, because Structure provides the likelihood associated with different numbers of sub-populations and the estimated percentage of shared ancestry with each sub-population for each entry.

Associations of individual SSR markers with tolerance to low-iron conditions were evaluated by logistic regression in TASSEL (Trait Analysis by aSSociation, Evolution, and Linkage) using the Structured Association analysis mode. TASSEL is provided by Edward Buckler, and information about the program can be found on the Buckler Lab web page at the Institute for Genomic Diversity at Cornell University. See, TASSEL Ver. 1.1.0 (released Jun. 23, 2005). The significance level for each association was tested using an empirical distribution that was established by running 5,000 permutations. Modifications of established procedures were made to accommodate the nature and characteristics of soybean and the soybean data set, especially with regard to those aspects that differ from rice.

Results

FIG. 1 provides a table listing the soybean markers that demonstrated linkage disequilibrium with the *Sclerotinia* tolerance phenotype using the Association Mapping method. Also indicated in that figure are the chromosomes on which the markers are located and their approximate map position relative to other known markers, given in cM, with position zero being the first (most distal) marker known at the beginning of the chromosome. These map positions are not absolute, and represent an estimate of map position. The SNP-type markers were detected by an allele specific hybridization (ASH) method, as known in the art (see, e.g., Coryell et al., (1999) "Allele specific hybridization markers for soybean," *Theor. Appl. Genet.*, 98:690-696). FIG. 2 provides the PCR primer sequences that were used to genotype these marker loci. FIG. 2 also provides the pigtail sequence used on the 5' end of the right SSR-marker primers and the number of nucleotides in the repeating element in the SSR. The alleles that are known to occur for the marker loci are provided in the SSR allele dictionary in FIG. 4. FIG. 3 provides the primer and probe sequences used to type the SNP markers.

The statistical probabilities that the marker allele and disease tolerance phenotype are segregating independently are reflected in the association mapping adjusted probability values in FIG. 1, which is a probability (P) derived from 5000 rounds of permutation analysis between genotype and phenotype. The permutations method for probability analysis is known in the art, and described in various sources, for example, Churchill and Doerge (1994), Genetics 138: 963-971; Doerge and Churchill (1996), Genetics 142: 285-294; Lynch and Walsh (1998) in *Genetics and analysis of quantitative traits*, published by Sinauer Associates, Inc. Sunderland, Mass. 01375, p. 441-442.

The lower the probability value, the more significant is the association between the marker genotype at that locus and the *Sclerotinia* infection tolerance phenotype. A more complete discussion of the derivation of the probability values can be found in the GeneFlow™ version 7.0 software documentation. See, also, Sokal and Rolf (1981), *Biometry: The Principles and Practices of Statistics in Biological Research*, 2nd ed., San Francisco, W. H. Freeman and Co.

Example 3

QTL Interval Mapping and Single Marker Regression Analysis

A QTL interval mapping and a single marker regression analysis was undertaken to identify soybean chromosome intervals and genetic markers (respectively) that are associated with tolerance and allow the plant to escape the pathology associated with *Sclerotinia* infection. QTL mapping and marker regression are widely used methods to identify genetic loci that co-segregate with a desired phenotype. By identifying such genetic loci, marker assisted selection (MAS) can be used to improve the efficiency of breeding for improved soybean strains.

Soybean Lines

A mapping population for *Sclerotinia* tolerance was created from the cross of commercially available Pioneer varieties 9163 and 92B05. The population consisted of 276 RIL progeny.

Phenotypic Scoring

Two sets of phenotypic data were collected. One set was collected from a misting nursery. The second set was collected from a non-inoculated, irrigated, naturally infested field site in St. Cloud, Minn. Known checks were planted along side the experimental plantings to verify disease pressure and uniformity. Phenotypic scoring of each of the 276 lines of progeny was based on one set of phenotypic data collected from the field. Based on that raw data, a composite score was also assigned for each line.

Soybean Genotyping

Soybean progeny were genotyped using a total of 253 polymorphic markers. Markers included genomic-SSR and EST-SSR markers. Because of heterozygosity of the parents, the LIMS has difficulty giving a score for the progeny based on the parent alleles. As a result, the data were subjected to manual editing. Following this editing, 182 markers were deemed useful. Of those 182 markers, 169 were mapped to 20 linkage groups. Another 13 are unlinked. Linkage group I had only one marker. Linkage group H had only three markers. This map covered approximately 65% of the soybean genome.

MapManager-QTXb20 (2004) was used for both the marker regression analysis and QTL interval mapping. The 1000 permutation tests were used to establish the threshold for statistical significance in the QTL interval analysis as measured by the likelihood ratio statistic (LRS). The LRS provides a measure of the linkage between variation in the phenotype and genetic differences at a particular genetic locus. LRS values can be converted to LOD scores (logarithm of the odds ratio) by dividing by 4.61. The term "likelihood of odds" is used to describe the relative probability of two or more explanations of the sources of variation in a trait. The probability of these two different explanations (models) can be computed, and most likely model chosen. If model A is 1000 times more probable than model B, then the ratio of the odds are 1000:1 and the logarithm of the odds ratio is 3.

Both the raw data and the composite score were used in QTL interval mapping. The LRS threshold for the misting nursery data and the field data at P=0.05 was 13.6 and 14.2, respectively. A confidence interval was estimated for each QTL by bootstrap resampling. After completing the interval mapping, the program will create multiple resampled datasets, perform interval mapping again with each of these sets, and record the position of the maximum LRS. The positions obtained are then plotted as a histogram overlaying the interval mapping figure.

Results

QTL Interval Mapping

The present study identified various chromosome intervals that correlate with QTL that associate with tolerance/susceptibility to *Sclerotinia* infection. The QTL were identified using the field data. One significant QTL was located on linkage group O. A second QTL was identified on linkage group L.

Single Marker Regression

Using single marker regression, there are a number of markers showing association with the tolerance phenotype at a confidence level of P=0.05 or better, as shown in FIG. 1. Some of the markers identified in the marker regression analysis show a concordance of observations with the association mapping and intergroup analysis data, where the different approaches identify the same markers. For example, the marker SATT391 is identified by both marker regression and association mapping.

Discussion/Conclusions

This present study has identified chromosome intervals and individual markers that correlate with *Sclerotinia* tolerance. Markers that lie within these intervals are useful for use in MAS, as well as other purposes.

Example 4

*Sclerotinia* Stem Rot Resistance Stem Lesion Phenotypic Assay

Various artificial methods are known in the art for assessing soybean susceptibility or tolerance to *Sclerotinia* stem rot. These methods can be favorably employed in controlled conditions (e.g., in nursery or greenhouse conditions) to test and quantitate plant tolerance. For example, as outlined in the EXAMPLE below, a stem lesion assay can be used.

Inoculum Source

Sclerotia from infected greenhouse plants are stored in culture tubes in a 45° C. refrigerator. Six days before plant inoculation, sclerotia are plated on potato dextrose agar (PDA) media and placed in a 25-27° C. incubator. After 4 days, a single plate with uniform mycelial growth extending to at least 1.5 inches in diameter is used. Plugs are cut in 4 mm squares from the edge of the mycelia and are plated in the center of PDA plates. Plates are then incubated at 25-27° C. for 24 hrs.

Carrot Preparation

Large fresh carrots are rinsed in distilled water and peeled. Carrots are cut into 5-10 cm sections and then pushed lengthwise through a Zyliss brand French frier. The resulting 8 mm square lengths are cut into approximately 2 mm thick pieces. Carrot pieces are placed in an autoclave bag and autoclaved for 1½ to 2 minutes.

Carrot Inoculation

Autoclaved carrot pieces are placed on the edge of the growing mycelia that was incubated for 24 hrs. Eight to twelve pieces are placed on each plate, depending on the mycelial diameter. Each carrot piece is placed with its outer edge positioned on the growing edge of the mycelia. Plates are incubated for an additional 22-24 hours.

Stem Inoculation

Plants are inoculated between the V3 and V4 stages. Each inoculated carrot piece is placed on a 2 inch square parafilm just at the tip of the center slit. The carrot piece on the parafilm is positioned on the stem internode just above the petiole immediately below the last fully developed leaf. The parafilm is wrapped around the stem with the center cut positioned downward. The carrot piece is pulled into contact with the stem while wrapping the parafilm.

Plant Incubation and Removal of Inoculum

Inoculated plants are placed on a shaded bench where a humidifier runs continually. The humidity in the room is set at 70%. Plants stay in this humidity chamber for 48 hrs. Inoculum is removed from stem-inoculated plants by taking off parafilm and pulling carrot pieces off. Paper tissues are used to wipe the plant stem of remaining inoculum.

Disease Scoring

Plants are typically scored for disease severity 6-8 days after inoculation. When the stem lesion assay is used to assay soybean plant tolerance to *Sclerotinia* stem rot, a tolerance score can be assigned to a test plant or test strain by comparing the severity of stem lesions in the test strain to the severity of stem lesions in a collection of reference strains (e.g., the reference strains taught herein) that are similarly cultured and analyzed in parallel to the experimental strain.

Alternatively, the test plants in the stem lesion assay can be scored on an absolute scale where a score of nine (9) indicates complete tolerance and immunity (absolute tolerance) with no signs of infection, and one (1) where the plant is highly susceptible to infection and the stem of the plant shows girdling and extensive lesions. Intermediate scores can be defined by the size and severity of stem lesioning.

Example 5

*Sclerotinia* Stem Rot Resistance Detached Leaf Phenotypic Assay

The present example provides a second artificial method for the assessment of soybean susceptibility or tolerance to *Sclerotinia* stem rot. This method, termed the detached leaf assay, is known in the art, and is described in various sources (see, e.g., Arahana et al., (2001) Crop Sci., 41:180-188). The assay is outlined below.

The detached leaf assay measures the size of a lesion produced by placing a mycelial plug on the trifoliolate soybean leaf. In contrast to the stem lesion assay described in EXAMPLE 2, this method presumably measures physiological tolerance. This method is developed for use on soybean, is nondestructive, allows multiple assays per year, and has consistent environmental control. In a comparison of the field evaluation, detached leaf assay, and other nonfield screening techniques, the detached leaf assay showed a significant correlation with field results (Kim et al., (2000) Crop Sci., 40:665-669; Steadman et al. (1997) Ann. Rep. Bean Improv. Coop., 40:140-141; Leone and Tonneijck (1990) Euphytica 48:87-90).

Plants are grown in a greenhouse, typically between December and May in 29.5 cm pots. To ultimately make four measurements of lesion size in *Sclerotinia* stem rot infected plants, six seeds per pot are planted and later thinned to four plants. Plants are grown to the V4 stage (Fehr and Caviness (1977) Stages of Soybean Development. Special Report (Iowa Agriculture and Home Economics Experiment Station) 80, Iowa State University, Ames, Iowa), the most recently developed fully expanded trifoliolate leaf of each plant is detached and wrapped in a wet paper towel for transfer to the laboratory.

Aluminum roasting pans are lined on the bottom with paper towels, and four petri plates are inverted and placed on the bottom of each pan. The detached leaves are placed over the inverted petri dishes, and each petiole is inserted in rubber stoppered orchid tubes containing distilled water. Experimental design for each population is typically an alpha lattice. In each replication, the lines are randomized in 26 pans, four leaves per pan. One replicate consists of one leaf. Plants sampled for one replication are tagged so they were not sampled again. Four replications are tested for each population.

A potato dextrose agar (PDA) plug from a culture of *S. sclerotiorum* isolate 143 (or any other suitable isolate) from soybean is placed near the center but not directly on the midvein of the middle leaflet. The 8-mm plug is taken from the advancing edge of the mycelium. After adding 300 mL of water to the bottom of each pan, a plastic film wrap is used to cover each pan to provide a humid environment. After 48 hours of incubation at a constant temperature of 22±1° C., the length and width of each lesion is measured with a ruler and the lesion area is determined by calculating the area of an elliptical circle encompassing the lesion. The smaller the elliptical area, the greater the plant tolerance to the *S. sclerotiorum* infection.

When the detached leaf assay is used to assay soybean plant tolerance to *Sclerotinia* stem rot, a tolerance score can be assigned to a test plant or test strain by comparing the area of the leaf lesion in the test strain to the area of the leaf lesions in a collection of reference strains (e.g., the reference strains taught herein) that are similarly cultured and analyzed in parallel to the experimental strain.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of identifying a first soybean plant or germplasm that displays tolerance, or improved tolerance to *Sclerotinia* sp. infection, the method comprising detecting in the first soybean plant or germplasm an allele of a marker locus that is associated with the tolerance, or improved tolerance, wherein the marker locus comprises the marker locus (a) S60817-TB and/or (b) a marker locus on linkage group F with a genetic recombination frequency of less than 20% with S60817-TB.

2. The method of claim 1, wherein the marker locus is selected from the group consisting of S60817-TB, BLT010_1, Satt423, AW186493, BE806387, Sat240, Satt659, Satt206, Sat_039, WI, BLT057_1, DUBC767, Sat_298, and Satt160.

3. The method of claim 1, wherein the marker locus associated with tolerance, or improved tolerance is marker locus S60817-TB.

4. The method of claim 1, wherein the germplasm is a soybean line or soybean variety.

5. The method of claim 1, wherein the tolerance, or improved tolerance to *Sclerotinia* stem rot is assayed in a field location previously known to produce soybean plants that demonstrate *Sclerotinia* stem rot, by a stem lesion assay or by a detached leaf assay.

6. The method of claim 1, wherein the *Sclerotinia* sp. is *Sclerotinia sclerotiotum* (Lib.) de Bary.

7. The method of claim 1, wherein the tolerance or improved tolerance is a non-race specific tolerance or a non-race specific improved tolerance.

8. The method of claim 1, wherein the detecting comprises detecting at least one allelic form of a polymorphic simple sequence repeat (SSR) or a single nucleotide polymorphism (SNP).

9. The method of claim 1, wherein the detecting comprises amplifying the marker locus or a portion of the marker locus and detecting the resulting amplified marker amplicon.

10. The method of claim 9, wherein the amplifying comprises:

a) admixing an amplification primer or amplification primer pair with a nucleic acid isolated from the first soybean plant or germplasm, wherein the primer or primer pair is complementary or partially complementary to at least a portion of the marker locus, and is capable of initiating DNA polymerization by a DNA polymerase using the soybean nucleic acid as a template; and, b) extending the primer or primer pair in a DNA polymerization reaction comprising a DNA polymerase and a template nucleic acid to generate at least one amplicon.

11. The method of claim 10, wherein the nucleic acid is selected from DNA and RNA.

12. The method of claim 9, wherein the at least one allele is an SNP allele, the method comprising detecting the SNP using allele specific hybridization (ASH) analysis.

13. The method of claim 9, wherein the amplifying comprises employing a polymerase chain reaction (PCR) or ligase chain reaction (LCR) using a nucleic acid isolated from the first soybean plant or germplasm as a template in the PCR or LCR.

14. The method of claim 1, wherein the at least one allele comprises S60817-TB:allele-2.

15. The method of claim 1, wherein the at least one allele is a favorable allele that positively correlates with tolerance or improved tolerance.

16. The method of claim 1, wherein the marker locus is determined using the mapping population 9163/92B05.

17. The method of claim 16, wherein the linked marker locus is determined using software selected from TASSEL, GeneFlow and MapManager-QTX.

18. The method of claim 1, comprising selecting the first soybean plant or germplasm, or selecting a progeny of the first soybean plant or germplasm.

19. The method of claim 18, comprising crossing the selected first soybean plant or germplasm with a second soybean plant or germplasm.

20. The method of claim 19, wherein the second soybean plant or germplasm comprises an exotic soybean strain or an elite soybean strain.

21. A method of identifying a first soybean plant or germplasm that displays tolerance, or improved tolerance to *Sclerotinia* sp. infection, the method comprising detecting in the first soybean plant or germplasm an allele of a marker locus that is associated with the tolerance, or improved tolerance, wherein the marker locus is defined by marker S60817-TB and/or a marker locus on linkage group F with a genetic recombination frequency of less than 20% with S60817-TB; and additionally detecting in the first soybean plant or germplasm at least one allele of the marker locus SATT243.

22. The method of claim 21, wherein the at least one allele of each selected marker locus is correlated with tolerance or improved tolerance to *Sclerotinia* sp. infection, the method further comprising introgressing the allele in the first soybean plant or germplasm into a second soybean plant or germplasm to produce an introgressed soybean plant or germplasm.

* * * * *

UNITED STATES PATENT AND TRADEMARK OFFICE
CERTIFICATE OF CORRECTION

PATENT NO. : 7,595,432 B2  Page 1 of 1
APPLICATION NO. : 11/282969
DATED : September 29, 2009
INVENTOR(S) : Sebastian et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 331 days.

Signed and Sealed this

Fourteenth Day of December, 2010

David J. Kappos
*Director of the United States Patent and Trademark Office*